US011850248B2

(12) United States Patent
Kang et al.

(10) Patent No.: US 11,850,248 B2
(45) Date of Patent: Dec. 26, 2023

(54) THERAPIES WITH 3RD GENERATION EGFR TYROSINE KINASE INHIBITORS

(71) Applicants: Janssen Biotech, Inc., Horsham, PA (US); Yuhan Corporation, Seoul (KR)

(72) Inventors: Seonmi Kang, Seoul (KR); Sewoong Oh, Suwon-si (KR)

(73) Assignee: Yuhan Corporation, Seoul (KR)

( * ) Notice: Subject to any disclaimer, the term of this patent is extended or adjusted under 35 U.S.C. 154(b) by 444 days.

(21) Appl. No.: 15/931,626

(22) Filed: May 14, 2020

(65) Prior Publication Data

US 2020/0360394 A1    Nov. 19, 2020

Related U.S. Application Data

(60) Provisional application No. 62/847,563, filed on May 14, 2019.

(51) Int. Cl.
| | | |
|---|---|---|
| *A61K 31/5377* | (2006.01) | |
| *A61P 35/00* | (2006.01) | |
| *A61P 35/04* | (2006.01) | |

(52) U.S. Cl.
CPC .......... *A61K 31/5377* (2013.01); *A61P 35/00* (2018.01); *A61P 35/04* (2018.01)

(58) Field of Classification Search
CPC ................................................ A61K 31/5377
See application file for complete search history.

(56) References Cited

U.S. PATENT DOCUMENTS

| | | |
|---|---|---|
| 9,593,098 B2 | 3/2017 | Suh et al. |
| 9,593,164 B2 | 3/2017 | Chiu et al. |
| 2005/0272083 A1 | 12/2005 | Seshagiri |
| 2020/0270351 A1 * | 8/2020 | Moores ............... C07K 16/2863 |

FOREIGN PATENT DOCUMENTS

| | | | |
|---|---|---|---|
| WO | WO 1992/01047 A1 | 1/1992 | |
| WO | WO 1994/13804 A2 | 6/1994 | |
| WO | WO 1988/01649 A1 | 3/1998 | |
| WO | WO 1998/44001 A1 | 10/1998 | |
| WO | WO 2008/077546 A1 | 7/2008 | |
| WO | WO 2009/085462 A1 | 7/2009 | |
| WO | 2016/060443 A2 | 4/2016 | |
| WO | WO2016/060443 * | 4/2016 | ........... C07D 403/04 |
| WO | WO 2018/094225 A1 | 5/2018 | |
| WO | 2018/194356 A1 | 10/2018 | |
| WO | WO2018/194356 * | 10/2018 | ........... C07D 413/14 |
| WO | 2019/022485 A1 | 1/2019 | |
| WO | 2019/022486 A1 | 1/2019 | |
| WO | 2019/022487 A1 | 1/2019 | |
| WO | WO2019/022485 * | 1/2019 | ........... C07D 413/14 |
| WO | 2020/079637 A1 | 4/2020 | |

OTHER PUBLICATIONS

Cho et al. Abstracts, vol. 13, Is. 10 (2018).*
Hong et al. J'nal of Thoracic Onc. vol. 12, (15) pp. S1265-S1266 (2017).*
Hynes et al. Nature Review Cancer, 2005, vol. 5, pp. 341-354.*
Cho, B.C., et al., "Lazertinib, a Third Generation EGFR-TKI, in Patients with EGFR-TKI-Resistant NSCLC: Updated Results of a Phase I/II Study," Abstracts, vol. 13, Issue 10, Oct. 2018, pp. S453.
Hong, M.H., et al., "YH25448, a Highly Selective 3rd Generation EGFR TKI, Exhibits Superior Survival over Osimertinib in Animal Model with Brain Metastases from NSCLC," Journal of Thoracic Oncology, vol. 12, No. 15, Jan. 2017, pp. S1265-S1266.
Bean et al., "MET amplification occurs with or without T790M mutations in EGFR mutant lung tumors with acquired resistance to gefitinib or erlotinib.", Proc Natl Acad Sci, USA, 2007, pp. 20932-20937, vol. 104(52).
Cappuzzo et al., "Epidermal Growth Factor Receptor Gene and Protein Gefitinib Sensitivity in Non-Small-Cell Lung Cancer.", J Natl Cancer Inst, May 4, 2005, pp. 643-655, vol. 97(9).
Chen et al., "Clinicopathologic and Molecular Features of Epidermal Growth Factor Receptor T790M Mutation and c-MET Amplification in Tyrosine Kinase Inhibitor-resistant Chinese Non-small Cell Lung Cancer.", Pathol Oncol Res, 2009, pp. 651-658, vol. 15.
Chothia et al., "Canocical Structures for the Hypervariable Regions of Immunoglobulins.", J Mol Biol, 1997, vol. 901-917, vol. 196.
Eisenhauer et al., "New response evaluation criteria in solid tumours: Revised RECIST guideline (version 1.1).", Eur J Cancer, 2009, pp. 228-247, vol. 45(2).
Engelman et al., "MET Amplification Leads to Gefitinib Resistance in Lung Cancer by Activating ERBB3 Signaling.", Science, May 18, 2007, pp. 1039-1043, vol. 316.
Ferrara et al., "Modulation of Therapeutic Antibody Effector Functions by Glycosylation Engineering: Influence of Golgi Enzyme Localization Domain and Co-Expression of Heterologous b1, 4-N-acetylglucosaminyltransferase III and Golgi a-mannosidase II.", Biotechnol Bioeng, 2006, pp. 851-861, vol. 93.
Honegger and Pluckthun, "Yet Another Numbering Scheme for Immunoglobulin Variable Domains: An Automatic Modeling and Analysis Tool.", J Mol Biol, 2001, pp. 657-670, vol. 309.
Janne and Johnson, "Effectof Epidermal Growth Factor Receptor Tyrosine Kinase Domain Mutations on the Outcome of Patient swith Non-Small Cell Lung Cancer Treated with Epidermal Growth Factor Receptor Tyrosine Kinase Inhibitors.", Clin Cancer, Jul. 15, 2006, pp. 4116s-4420s, vol. 12(14 Suppl).
Jeffers et al., "Hepatocyte growth factor/scatter factor—Met signaling in tumorigenicity and invasion/metastasis.", J Mol Med, 1996, pp. 505-513, vol. 74(9).
Knappik et al., "Fully Synthetic Human Combinatorial Antibody Libraries (HuCAL) Based on Modular Consensus Frameworks and CDRs Randomized with Trinucleotides.", J Mol Biol, 2000, pp. 57-86, vol. 296.

(Continued)

*Primary Examiner* — Paul V Ward
(74) *Attorney, Agent, or Firm* — BakerHostetler

(57) ABSTRACT

The present invention relates to therapies with 3rd generation EGFR tyrosine kinase inhibitors. Embodiments of the invention relate to the administration of lazertinib to patients diagnosed with non-small cell lung cancer (NSCLC).

7 Claims, 6 Drawing Sheets

Specification includes a Sequence Listing.

(56) References Cited

OTHER PUBLICATIONS

Kobayashi et al., "EGFR Mutation and Resistance of Non-Small-Cell Lung Cancer to Gefitinib.", New Engl J Med, Feb. 24, 2005, pp. 786-792, vol. 352(8).
Konno et al., "Fucose content of monoclonal antibodies can be controlled by culture medium osmolality for high antibody-dependent cellular cytotoxicity.", Cytotechnology, 2012, pp. 249-265, vol. 64.
Lefranc et al., "IMGT unique numbering for immunoglobulin and T cell receptor variable domains and Ig superfamily V-like domains.", Dev Comp Immunol, 2002, pp. 55-77, vol. 27.
Martin and Thornton, "Structural Families in Loops of HomologousProteins: Automatic Classification, Modelling and Application to Antibodies.", J Bmol Biol, 1996, pp. 800-815, vol. 263.
Mori et al., "Engineering Chinese Hamster Ovary Cells to Maximize Effector Function of Produced Antibodies Using FUT8 siRNA.", Biotechnol Bioeng, 2004, pp. 901-908, vol. 88.
Nakata and Gotoh, "Recent understanding of the molecular mechanisms for the efficacy and resistance of EGF receptor-specific tyrosine kinase inhibitors in non-small cell lung cancer.", Expert Opin Ther Targets, 2012, pp. 771-781, vol. 16.
Olivier et al., "EB66 cell line, a duck embryonic stem cell-derived substrate for the industrial production of therapeutic monoclonal antibodies with enhanced ADCC activity.", Mabs, Jul./Aug. 2010, pp. 405-415, vol. 2(4), Epub ahead of print; PMID:20562582.
Pao et al., "Acquired Resistance of Lung Adenocarcinomas to Gefitinib or Erlotinib Is Associated with a Second Mutation in the EGFR Kinase Domain.", PLOS Med, Mar. 2005, pp. 0225-0235, vol. 2(3):e73.
Pérez-Soler R et al., "Determinants of Tumor Response and Survival With Erlotinib in Patients With Non-Small-Cell Lung Cancer.", J Clin Oncol, Aug. 15, 2004, pp. 3238-3247, vol. 22(16).
Sequist et al., "Genotypic and Histological Evolution of Lung Cancers Acquiring Resistance to EGFR Inhibitors.", Sci Transl Med, Mar. 23, 2011, pp. 1-12, vol. 3(75):75ra26.
Shi et al., "De Novo Selection of High-Affinity Antibodies from Synthetic Fab Libraries Displayed on Phage as pIX Fusion Proteins.", J Mol Biol, 2010, pp. 385-396, vol. 397.
Shields et al., "High Resolution Mapping of the Binding Site on Human IgG1 for FcgRI, FcgRII, FcgRIII, and FcRn and Design of IgG1 Variants with Improved Binding to the FcgR.", J Biol Chem, Mar. 2, 2002, pp. 6591-6604, vol. 277(9).
Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity.", J Biol Chem, Jan. 31, 2003, pp. 3466-3473, vol. 278(5).
Turke et al., "Preexistence and Clonal Selection of MET Amplification in EGFR Mutant NSCLC.", Cancer Cell, Jan. 19, 2010, pp. 77-88, vol. 17.
Ullrich et al., "Human epidermal growth factor receptor cDNA sequence and aberrant expression of the amplified gene in A431 epidermoid carcinoma cells.", Nature, May 31, 1984, pp. 418-425, vol. 309.
Wu et al., "An analysis of the Sequences of the Variable Regions of Bence Jones Proteins and Myeloma Light Chains and Their Implications for Antibody Complementarity.", J Exp Med, 1970, pp. 211-250, vol. 132.
Zhou et al., "Development of A Simple and Rapid Method for Producing Non-Fucosylated Oligomannose Containing Antibodies With Increased Effector Function.", Biotechnol Bioeng, 2008, pp. 652-665, vol. 99.
Yano et al., "Hepatocyte Growth Factor Induces Gefitinib Resistance of Lung Adenocarcinoma with Epidermal Growth Factor Receptor-Activating Mutations.", Cancer Res, Nov. 15, 2008, pp. 9479-9487, vol. 68(22).
Yun et al., "The T790M mutation in EGFR kinase causes drug resistance by increasing the affinity for ATP.", Proc Natl Acad Sci, U.S.A., Feb. 12, 2008, pp. 2070-2075, vol. 105(6).
Yun, Jiyeon et al., "YH25448, an irreversible EGFR-TKI with Potent Intracranial Activity in EGFR mutant non-small-cell lung cancer," Clinical Cancer Research, Apr. 15, 2019, pp. 2575-2587, vol. 25(8).
Cho et al. ASCO Annual Meeting, Abstract 9033. YH25448, a 3rd generation EGFR-TKI, in patients with EGFR-TKI-resistant NSCLC: Phase I/II study results; Jun. 3, 2018.
Cho et al. ASCO Annual Meeting, Poster #356. YH25448, a 3rd generation EGFR-TKI, in patients with EGFR-TKI-resistant NSCLC: Phase I/II study results; Jun. 1-5, 2018.
ClinicalTrials.gov archive dated Apr. 14, 2017. Study NCT03046992: A Phase I/II, Open-Label, Multicenter Study to Evaluate the Safety, Tolerability, Pharmacokinetics and Anti-Tumor Activity of YH25448 in Patients With EGFR Mutation Positive Advanced Non-Small Cell Lung Cancer (NSCLC).
ClinicalTrials.gov archive dated Feb. 7, 2017. Study NCT03046992: A Phase I/II, Open-Label, Multicenter Study to Evaluate the Safety, Tolerability, Pharmacokinetics and Anti-Tumor Activity of YH25448 in Patients With EGFR Mutation Positive Advanced Non-Small Cell Lung Cancer (NSCLC).
ClinicalTrials.gov archive dated Jan. 14, 2019. Study NCT03046992: A Phase I/II, Open-Label, Multicenter Study to Evaluate the Safety, Tolerability, Pharmacokinetics and Anti-Tumor Activity of YH25448 in Patients With EGFR Mutation Positive Advanced Non-Small Cell Lung Cancer (NSCLC).
ClinicalTrials.gov archive dated Jul. 1, 2017. Study NCT03046992: A Phase I/II, Open-Label, Multicenter Study to Evaluate the Safety, Tolerability, Pharmacokinetics and Anti-Tumor Activity of YH25448 in Patients With EGFR Mutation Positive Advanced Non-Small Cell Lung Cancer (NSCLC).
ClinicalTrials.gov archive dated May 29, 2018. Study NCT03046992: A Phase I/II, Open-Label, Multicenter Study to Evaluate the Safety, Tolerability, Pharmacokinetics and Anti-Tumor Activity of YH25448 in Patients With EGFR Mutation Positive Advanced Non-Small Cell Lung Cancer (NSCLC).
Genosco/Yuhan. ASCO 2018: Genosco/Yuhan Announce Results from Phase 1/2 Study of Lazertinib (YH25448, GNS-1480), a 3rd-Generation EGFR-TKI, in Advanced NSCLC; Jun. 3, 2018.
Hynes et al., "ERBB receptors and cancer: The Complexity of Targeted Inhibitors", Nature Review Cancer, 2005, vol. 5, pp. 341-354.
Shields et al., "Lack of Fucose on Human IgG1 N-Linked Oligosaccharide Improves Binding to Human FcyRIII and Antibody dependent Cellular Toxicity", The Journal of Biological Chemistry, 2002, vol. 277, pp. 26733-26740.

* cited by examiner

THERAPIES WITH 3RD GENERATION EGFR TYROSINE KINASE INHIBITORS

CROSS REFERENCE TO RELATED APPLICATIONS

This application claims the benefit of priority of U.S. Provisional Application No. 62/847,563, filed on May 14, 2019, which is incorporated by reference herein, in its entirety and for all purposes.

REFERENCE TO SEQUENCE LISTING SUBMITTED ELECTRONICALLY

This application contains a sequence listing, which is submitted electronically via EFS-Web as an ASCII formatted sequence listing with a file name "JBI6094USNP1SEQLIST.TXT" and a creation date of Apr. 30, 2020, and having a size of 22 kb. The sequence listing submitted via EFS-Web is part of the specification and is herein incorporated by reference in its entirety.

FIELD OF THE INVENTION

The present invention relates to therapies involving $3^{rd}$ generation EGFR tyrosine kinase inhibitors; including combination therapies with bispecific anti-EGFR/c-Met antibodies and $3^{rd}$ generation EGFR tyrosine kinase inhibitors.

BACKGROUND OF THE INVENTION

Lazertinib or its pharmaceutically acceptable salt has activity of selectively inhibiting protein kinase, particularly, protein kinase for a mutant epidermal growth factor receptor, and may provide, for example, an effective and safe treatment method for non-small cell lung cancer. Lazertinib or its pharmaceutically acceptable salt has been known as an irreversible EGFR TKI which has a less effect on wild-type EGFR, strong inhibitory activity on T790M single active mutation (EGFRm) and double mutation, and excellent selectivity.

The individual roles of both EGFR and c-Met receptors in cancer is well established, making these targets attractive for combination therapy. Both receptors signal through the same ERK and AKT survival and anti-apoptotic pathways and often are upregulated as a resistant mechanism for either single agent treatment; thus, inhibiting the pair in combination may limit the potential for compensatory pathway activation thereby acting synergistically to inhibit tumor pro-growth signaling and improving overall clinical efficacy.

Relapse or resistance to existing therapeutics is common. Hence, there is a need for improved therapeutics or combination of therapeutics and patient stratification biomarkers to develop more effective treatment of a disease, such as EGFR or c-Met positive cancer

SUMMARY OF THE INVENTION

An embodiment of the disclosure provides a method of treating a subject having an EGFR or c-Met expressing cancer, comprising administering to the subject a combination therapy, wherein the combination therapy comprises a therapeutically effective amount of an isolated bispecific anti-epidermal growth factor receptor (EGFR)/hepatocyte growth factor receptor (c-Met) antibody and a therapeutically effective amount of a compound of formula (I)

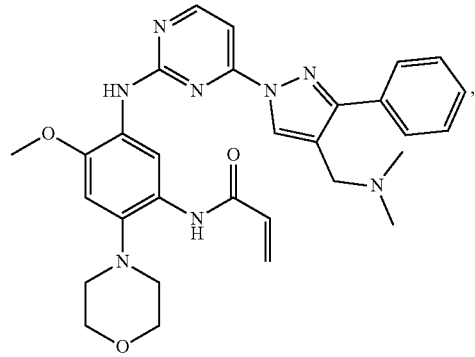

or solvate, hydrate, tautomer, or a pharmaceutically acceptable salt thereof. According to particular embodiments, the compound of formula (I) or solvate, hydrate, tautomer, or pharmaceutically acceptable salt thereof is the mesylate salt of lazertinib.

An embodiment of the disclosure provides a pharmaceutical combination comprising (1) a bispecific anti-EGFR/c-Met antibody comprising a first domain that binds EGFR comprising the HCDR1 of SEQ ID NO: 1, the HCDR2 of SEQ ID NO: 2, the HCDR3 of SEQ ID NO: 3, the LCDR1 of SEQ ID NO: 4, the LCDR2 of SEQ ID NO: 5 and the LCDR3 of SEQ ID NO: 6 and a second domain that binds c-Met comprising the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12; and (2) lazertinib or a pharmaceutically acceptable salt thereof (e.g., the mesylate salt of lazertinib).

An embodiment of the disclosure provides a method of reducing the size of a brain lesion in a human subject diagnosed with NSCLC comprising administering to the subject a therapeutically effective amount of a compound of formula (I) or a solvate, hydrate, tautomer, or a pharmaceutically acceptable salt thereof.

DETAILED DESCRIPTION OF THE INVENTION

Definitions

Figure 1:
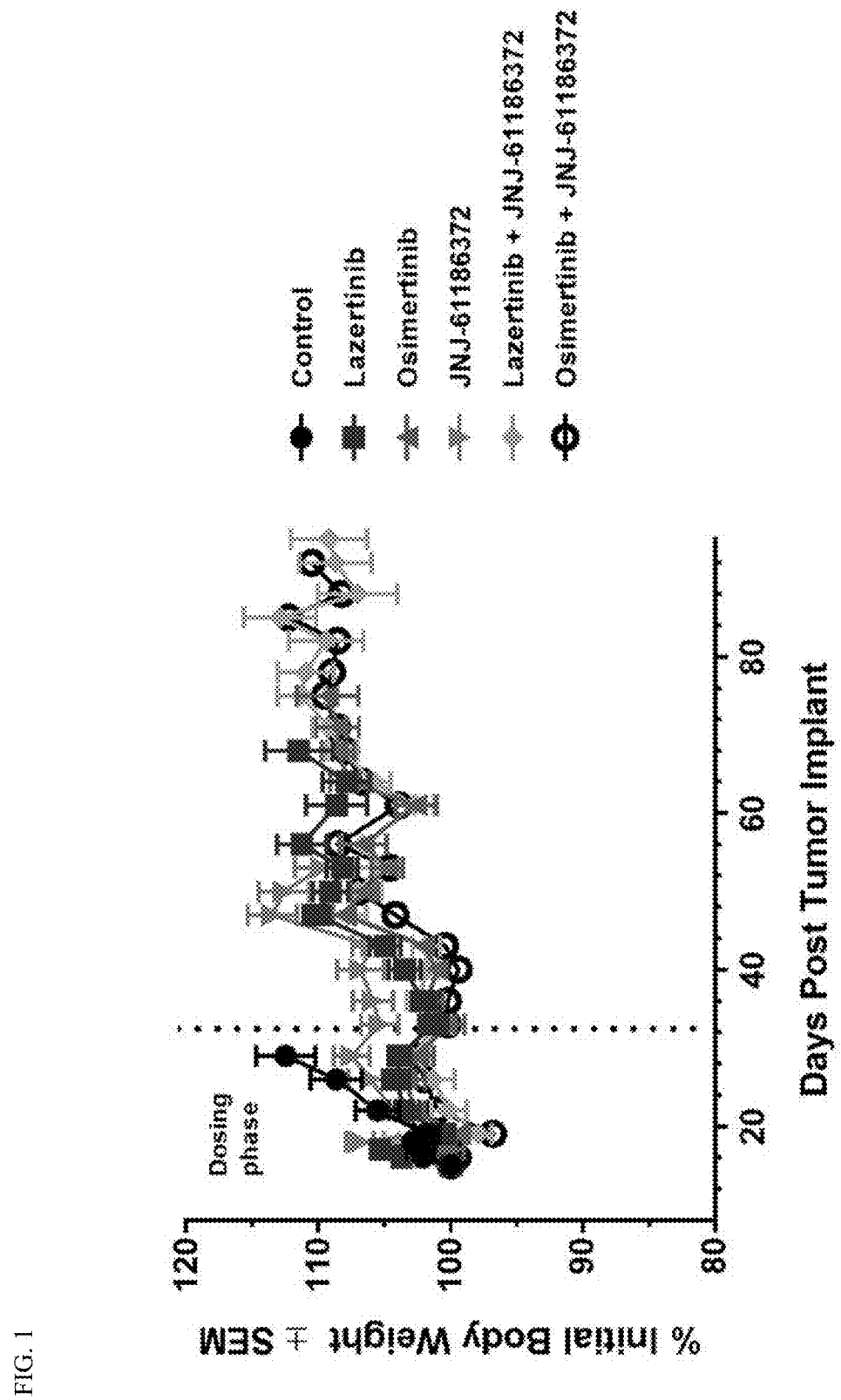
FIG. 1 shows the effect of JNJ-61186372 monotherapy or combination with lazertinib or osimertinib on body weight of nude mice bearing H1975 xenografts.

All publications, including but not limited to patents and patent applications, cited in this specification are herein incorporated by reference as though fully set forth.

It is to be understood that the terminology used herein is for describing particular embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein may be used in the practice for testing of the present invention, exemplary materials and methods are described herein. In describing and claiming the present invention, the following terminology will be used.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is larger.

"About once a week" or "weekly" refers to administration one time over about a one week period. About a one week period refers 7 days±two days, i.e., 5 days to 9 days. The dosing frequency of "about once a week" thus can be once every five days, once every six days, once every seven days, once every eight days, or once every nine days.

"About once in two weeks" refers to administration one time over about a two week period. About a two week period refers to 14 days±two days, i.e., 12 days to 16 days. The dosing frequence of "about once in two weeks" thus can be once every 12 days, once every 13 days, once every 14 days, once every 15 days or once every 16 days.

As used in this specification and the appended claims, the singular forms "a," "an," and "the" include plural referents unless the content clearly dictates otherwise. Thus, for example, reference to "a cell" includes a combination of two or more cells, and the like.

The conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

"Antagonist" or "inhibitor" refers to a molecule that, when bound to a cellular protein, suppresses at least one reaction or activity that is induced by a natural ligand of the protein. A molecule is an antagonist when the at least one reaction or activity is suppressed by at least about 20%, 30%, 40%, 45%, 50%, 55%, 60%, 65%, 70%, 75%, 80%, 85%, 90%, 95%, or 100% more than the at least one reaction or activity suppressed in the absence of the antagonist (e.g., negative control), or when the suppression is statistically significant when compared to the suppression in the absence of the antagonist.

"Antibodies" is meant in a broad sense and includes immunoglobulin molecules including monoclonal antibodies including murine, human, humanized and chimeric monoclonal antibodies, antigen binding fragments, multispecific antibodies, such as bispecific, trispecific, tetraspecific etc., dimeric, tetrameric or multimeric antibodies, single chain antibodies, domain antibodies and any other modified configuration of the immunoglobulin molecule that comprises an antigen binding site of the required specificity. "Full length antibodies" are comprised of two heavy chains (HC) and two light chains (LC) inter-connected by disulfide bonds as well as multimers thereof (e.g. IgM). Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL regions may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4. Immunoglobulins may be assigned to five major classes, IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species may be assigned to one of two clearly distinct types, namely kappa (κ) and lambda (λ), based on the amino acid sequences of their constant domains.

"Antigen binding fragment" refers to a portion of an immunoglobulin molecule that binds an antigen. Antigen binding fragments may be synthetic, enzymatically obtainable or genetically engineered polypeptides and include the VH, the VL, the VH and the VL, Fab, F(ab')2, Fd and Fv fragments, domain antibodies (dAb) consisting of one VH domain or one VL domain, shark variable IgNAR domains, camelized VH domains, minimal recognition units consisting of the amino acid residues that mimic the CDRs of an antibody, such as FR3-CDR3-FR4 portions, the HCDR1, the HCDR2 and/or the HCDR3 and the LCDR1, the LCDR2 and/or the LCDR3. VH and VL domains may be linked together via a synthetic linker to form various types of single chain antibody designs where the VH/VL domains may pair intramolecularly, or intermolecularly in those cases when the VH and VL domains are expressed by separate single chain antibody constructs, to form a monovalent antigen binding site, such as single chain Fv (scFv) or diabody; described for example in Int. Patent Publ. Nos. WO1998/44001, WO1988/01649, WO1994/13804 and WO1992/01047.

"Bispecific" refers to an antibody that specifically binds two distinct antigens or two distinct epitopes within the same antigen. The bispecific antibody may have cross-reactivity to other related antigens, for example to the same antigen from other species (homologs), such as human or monkey, for example *Macaca* cynomolgus (cynomolgus, cyno) or Pan troglodytes, or may bind an epitope that is shared between two or more distinct antigens.

"Bispecific anti-EGFR/c-Met antibody" or "bispecific EGFR/c-Met antibody" refers to a bispecific antibody having a first domain that specifically binds EGFR and a second domain that specifically binds c-Met. The domains specifically binding EGFR and c-Met are typically VH/VL pairs. The bispecific antibody may be, depending on the structure, monovalent, bivalent or multivalent in terms of binding to EGFR and c-Met; i.e., can have one or more domains that bind EGFR and one or more domains that bind c-Met.

"Biological sample" refers to a collection of similar fluids, cells, or tissues isolated from a subject, as well as fluids, cells, or tissues present within a subject. Exemplary samples are biological fluids such as blood, serum and serosal fluids, plasma, lymph, urine, saliva, cystic fluid, tear drops, feces, sputum, mucosal secretions of the secretory tissues and organs, vaginal secretions, ascites fluids, fluids of the pleural, pericardial, peritoneal, abdominal and other body cavities, fluids collected by bronchial lavage, synovial fluid, liquid solutions contacted with a subject or biological source, for example, cell and organ culture medium including cell or organ conditioned medium, lavage fluids and the like, tissue biopsies, tumor tissue biopsies, tumor tissue samples, fine needle aspirations, surgically resected tissue, organ cultures or cell cultures.

"Complementarity determining regions" (CDR) are antibody regions that bind an antigen. CDRs may be defined using various delineations such as Kabat (Wu et al. (1970) *J Exp Med* 132: 211-50) (Kabat et al., Sequences of Proteins of Immunological Interest, 5th Ed. Public Health Service, National Institutes of Health, Bethesda, Md., 1991), Chothia (Chothia et al. (1987) *J Mol Biol* 196: 901-17), IMGT (Lefranc et al. (2003) *Dev Comp Immunol* 27: 55-77) and AbM (Martin and Thornton (1996) *J Bmol Biol* 263: 800-15). The correspondence between the various delineations and variable region numbering are described (see e.g. Lefranc et al. (2003) *Dev Comp Immunol* 27: 55-77; Honegger and Pluckthun, (2001) *J Mol Biol* 309:657-70; International ImMunoGeneTics (IMGT) database; Web resources, http://www_imgt_org). Available programs such as abYsis by UCL Business PLC may be used to delineate CDRs. The term "CDR", "HCDR1", "HCDR2", "HCDR3", "LCDR1", "LCDR2" and "LCDR3" as used herein includes CDRs defined by any of the methods described supra, Kabat, Chothia, IMGT or AbM, unless otherwise explicitly stated in the specification The transitional terms "comprising," "consisting essentially of," and "consisting of" are intended to connote their generally accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents) also provide as embodiments those independently described in terms of "consisting of" and "consisting essentially of".

"Cancer" refers to an abnormal growth of cells which tend to proliferate in an uncontrolled way and, in some cases, to metastasize (spread) to other areas of a patient's body.

"Co-administration," "administration with," "administration in combination with", "in combination with", "combination therapy" or the like, encompass administration of two or more therapeutics to a single patient, and are intended to include treatment regimens in which the therapeutics are administered by the same or different route of administration or at the same or different time.

"Diagnosing" or "diagnosis" refers to methods to determine if a subject is suffering from a given disease or condition or may develop a given disease or condition in the future or is likely to respond to treatment for a prior diagnosed disease or condition, i.e., stratifying a patient population on likelihood to respond to treatment. Diagnosis is typically performed by a physician based on the general guidelines for the disease to be diagnosed or other criteria that indicate a subject is likely to respond to a particular treatment.

"Dosage" refers to the information of the amount of the therapeutic or the drug to be taken by the subject and the frequency of the number of times the therapeutic is to be taken by the subject.

"Dose" refers to the amount or quantity of the therapeutic or the drug to be taken each time.

"EGFR or c-Met expressing cancer" refers to cancer that has detectable expression of EGFR or c-Met or has EGFR or c-Met mutation or amplification. EGFR or c-Met expression, amplification and mutation status can be detected using known methods, such as sequencing, fluorescent in situ hybridization, immunohistochemistry, flow cytometry or western blotting using tumor biopsies or blood samples. Expression can also be detected by sequencing from circulating tumor DNA (ctDNA).

"Epidermal growth factor receptor" or "EGFR" refers to the human EGFR (also known as HER1 or ErbB1 (Ullrich et al., *Nature* 309:418-425, 1984) having the amino acid sequence shown in GenBank accession number NP_005219, as well as naturally-occurring variants thereof.

"Fucose content" refers to the amount of the fucose monosaccharide within the sugar chain at Asn297 in an antibody preparation.

"Hepatocyte growth factor receptor" or "c-Met" as used herein refers to the human c-Met having the amino acid sequence shown in GenBank Accession No: NP_001120972 and natural variants thereof.

"Human antibody" refers to an antibody that is optimized to have minimal immune response when administered to a human subject. Variable regions of human antibody are derived from human immunoglobulin sequences. If human antibody contains a constant region or a portion of the constant region, the constant region is also derived from human immunoglobulin sequences. Human antibody comprises heavy and light chain variable regions that are "derived from" sequences of human origin if the variable regions of the human antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci. "Human antibody" typically contains amino acid differences when compared to the immunoglobulins expressed in humans due to differences between the systems used to obtain the human antibody and human immunoglobulin loci, introduction of somatic mutations or intentional introduction of substitutions into the frameworks or CDRs, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., (2000) J Mol Biol 296:57-86, or synthetic HCDR3 incorporated into human immunoglobulin gene libraries displayed on phage, for example as described in Shi et al., (2010) J Mol Biol 397:385-96, and in Int. Patent Publ. No. WO2009/085462. Antibodies in which at least one CDR is derived from a non-human species are not included in the definition of "human antibody"

"Isolated" refers to a homogenous population of molecules (such as synthetic polynucleotides, polypeptides vectors or viruses) which have been substantially separated and/or purified away from other components of the system the molecules are produced in, such as a recombinant cell, as well as a protein that has been subjected to at least one purification or isolation step. "Isolated" refers to a molecule that is substantially free of other cellular material and/or chemicals and encompasses molecules that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Low fucose" or "low fucose content" refers to antibodies with fucose content of about between 1%-15%.

"Monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation. Monoclonal antibodies typically bind one antigenic epitope. A bispecific monoclonal antibody binds two distinct antigenic epitopes. Monoclonal antibodies may have heterogeneous glycosylation within the antibody population. Monoclonal antibody may be monospecific or multispecific such as bispecific, monovalent, bivalent or multivalent.

"Newly diagnosed" refers to a subject who has been diagnosed with a cancer, such as EGFR or c-Met expressing cancer, but has not yet received treatment for the cancer.

"Normal fucose" or 'normal fucose content" refers to antibodies with fucose content of over about 50%, typically over about 80% or over about 85%.

"Pharmaceutical composition" refers to a composition comprising an active ingredient such as the bispecific EGFR/c-Met antibody and one or more pharmaceutically acceptable carriers, or such as the EGFR TK inhibitor lazertinib, or solvate, hydrate, tautomer, or a pharmaceutically acceptable salt thereof, and one or more pharmaceutically acceptable carriers.

"Pharmaceutically acceptable carrier" or "excipient" refers to an ingredient in a pharmaceutical composition, other than the active ingredient, which is nontoxic to a subject. A pharmaceutically acceptable carrier includes, but is not limited to, a buffer, stabilizer or preservative. A pharmaceutically acceptable carrier includes, but is not limited to, a diluent, disintegrant, or glidant; or a diluent, disintegrant, wetting agent, glidant or lubricant.

"Prevent", "preventing", "prevention", or "prophylaxis" of a disease or disorder means preventing that a disorder occurs in subject.

"Recombinant" refers to DNA, antibodies and other proteins that are prepared, expressed, created or isolated by recombinant means when segments from different sources are joined to produce recombinant DNA, antibodies or proteins.

"Refractory" refers to a disease that does not respond to a treatment. A refractory disease can be resistant to a treatment before or at the beginning of the treatment, or a refractory disease can become resistant during a treatment.

"Relapsed" refers to the return of a disease or the signs and symptoms of a disease after a period of improvement after prior treatment with a therapeutic.

"Responsive", "responsiveness" or "likely to respond" refers to any kind of improvement or positive response, such as alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable.

"Solvates" and "hydrates" are solvent addition forms which the compounds of the present invention are able to form, whereby the multicomponent compound contains both the host molecule (e.g., compound of Formula (I) or salt thereof) and guest molecule (water ("hydrate") or another solvent ("solvate")) incorporated in the structure.

"Specific binding" or "specifically binds" or "specifically binding" or "binds" refer to an antibody binding to an antigen or an epitope within the antigen with greater affinity than for other antigens. Typically, the antibody binds to the antigen or the epitope within the antigen with an equilibrium dissociation constant ($K_D$) of about $5\times10^{-8}$ M or less, for example about $1\times10^{-9}$ M or less, about $1\times10^{-10}$ M or less, about $1\times10^{-12}$ M or less, or about $1\times10^{-12}$ M or less, typically with the $K_D$ that is at least one hundred-fold less than its $K_D$ for binding to a non-specific antigen (e.g., BSA, casein). The dissociation constant may be measured using known protocols. Antibodies that bind to the antigen or the epitope within the antigen may, however, have cross-reactivity to other related antigens, for example to the same antigen from other species (homologs), such as human or monkey, for example *Macaca fascicularis* (cynomolgus, cyno) or Pan troglodytes (chimpanzee, chimp). While a monospecific antibody binds one antigen or one epitope, a bispecific antibody binds two distinct antigens or two distinct epitopes.

"Subject" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. The terms "subject" and "patient" are used interchangeably herein.

"Tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerisations. Valence tautomers include interconversions by reorganization of some of the bonding electrons.

"Therapeutically effective amount" refers to an amount effective, at doses and for periods of time necessary, to achieve a desired therapeutic result. A therapeutically effective amount may vary depending on factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the patient.

"Treat", "treating" or "treatment" of a disease or disorder such as cancer refers to accomplishing one or more of the following: reducing the severity and/or duration of the disorder, inhibiting worsening of symptoms characteristic of the disorder being treated, limiting or preventing recurrence of the disorder in subjects that have previously had the disorder, or limiting or preventing recurrence of symptoms in subjects that were previously symptomatic for the disorder.

"Treatment naïve" in a context of EGFR tyrosine kinase inhibitor (TKI) refers to a subject who has not received EGFR TKI treatment.

"Humanized antibody" refers to an antibody in which at least one CDR is derived from non-human species and at least one framework is derived from human immunoglobulin sequences. Humanized antibody may include substitutions in the frameworks so that the frameworks may not be exact copies of expressed human immunoglobulin or human immunoglobulin germline gene sequences.

"1$^{st}$ generation EGFR tyrosine kinase inhibitor" (1$^{st}$ generation TKI) refers to reversible EGFR inhibitors such as gefitinib and erlotinib, which are effective in first-line treatment of NSCLC harboring EGFR activating mutations such as deletions in exon 19 and exon 21 L858R mutation.

"2$^{nd}$ generation EGFR tyrosine kinase inhibitor" (2$^{nd}$ generation TKI) refers to covalent irreversible EGFR inhibitors such as afatinib and dacomitib which are effective in first-line treatment of NSCLC harboring EGFR activating mutations such as deletions in exon 19 and exon 21 L858R mutation.

"3$^{rd}$ generation EGFR tyrosine kinase inhibitor" (3$^{rd}$ generation TKI) refers to covalent irreversible EGFR inhibitors such as osimertinib and lazertinib which are selective to the EGFR activating mutations, such as deletions in exon 19 and exon 21 L858R, alone or in combination with T790M mutation and have lower inhibitory activity against wild-type EGFR.

Methods of the Disclosure

NSCLC is frequently driven by activating mutations in the kinase domain of EGFR, occurring most commonly as in-frame deletions in exon 19 or L858R mutation in exon 21. Most patients with these activating EGFR mutations initially respond to first-generation EGFR TKIs, such as gefitinib and erlotinib; however, drug resistance limits the response to a mean duration of less than 1 year (Kobayashi et al., *New Engl J Med* 2005; 352(8):786-792; Pérez-Soler R et al., *J Clin Oncol* 2004; 22(16):3238-3247). The T790M secondary mutation in EGFR has been identified in approximately 50% of EGFR-mutant NSCLC patients with resistant disease (Chen et al., *Pathol Oncol Res* 2009; 15(4):651-658; Jeffers et al., *J Mol Med* (Berl). 1996; 74(9):505-513; Pao et al., *PLoS Med* 2005; 2(3):e73; Sequist et al., *Sci Transl Med* 2011; 3(75):75ra26). This mutation results in an EGFR kinase with increased affinity for adenosine triphosphate, thus reducing the potency of reversible TKIs (Yun et al., *Proc Natl Acad Sci USA*. 2008; 105(6):2070-2075). In addition, resistant tumors may activate the c-Met pathway, through MET gene amplification, increased c-Met protein expression, and/or increased expression of the c-Met ligand, HGF (Engelman et al., *Science* 2007; 316(5827):1039-1043; Yano et al., *Cancer Res* 2008; 68(22):9479-9487). Stimulation of the c-Met pathway provides an alternative mechanism to activate the phosphatidylinositol-3 kinase/Akt signaling pathway, thus bypassing the TKI blockade of EGFR and facilitating the survival of cancer cells. These two mechanisms occur simultaneously in 5% to 33% of NSCLC patients resistant to EGFR TKIs (Bean et al., *Proc Nat Acad Sci USA* 2007; 104(52):20932-20937).

JNJ-61186372 (JNJ-372) is a bispecific anti-EGFR/c-Met antibody that inhibits both EGFR and c-Met signaling, by blocking ligand-induced activation and by inducing receptor degradation and is described in U.S. Pat. No. 9,593,164, which is incorporated by reference herein. In addition, the presence of high levels of EGFR and c-Met on the surface of tumor cells enables targeting of these cells for destruction by immune effector cells through Fc-mediated effector mechanisms, such as antibody-dependent cellular cytotoxicity (ADCC) and antibody-dependent cellular phagocytosis (ADCP). JNJ-372 is defined by the following amino acid sequences: the EGFR binding domain comprises a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6; the c-Met binding domain comprises the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12; the EGFR binding domain comprises a heavy chain variable domain (VH) of SEQ ID NO: 13 and a light chain variable domain (VL) of SEQ ID NO: 14; the c-Met binding domain comprises the VH of SEQ ID NO: 15 and the VL of SEQ ID NO: 16; the antibody comprises a first heavy chain (HC1) of SEQ ID NO: 17, a first light chain (LC1) of SEQ ID NO: 18, a second heavy chain (HC2) of SEQ ID NO: 19 and a second light chain (LC2) of SEQ ID NO: 20.

```
(HCDR1, EGFR binding arm)
                                       SEQ ID NO: 1
TYGMH (HCDR2, EGFR binding arm)
                                       SEQ ID NO: 2
VIWDDGSYKYYGDSVKG (HCDR3, EGFR binding arm)
                                       SEQ ID NO: 3
DGITMVRGVMKDYFDY (LCDR1, EGFR binding arm)
                                       SEQ ID NO: 4
RASQDISSALV (LCDR2, EGFR binding arm)
                                       SEQ ID NO: 5
DASSLES (LCDR3, EGFR binding arm)
                                       SEQ ID NO: 6
QQFNSYPLT (HCDR1, c-Met binding arm)
                                       SEQ ID NO: 7
SYGIS (HCDR2, c-Met binding arm)
                                       SEQ ID NO: 8
WISAYNGYTNYAQKLQG (HCDR3, c-Met binding arm)
                                       SEQ ID NO: 9
DLRGTNYFDY
```

-continued (LCDR1, c-Met binding arm)
SEQ ID NO: 10
RASQGISNWLA (LCDR2, c-Met binding arm)
SEQ ID NO: 11
AASSLLS (LCDR3, c-Met binding arm)
SEQ ID NO: 12
QQANSFPIT (VH, EGFR binding arm)
SEQ ID NO: 13
QVQLVESGGGVVQPGRSLRLSCAASGFTFSTYGMHWVRQAPGKGLEWVAVI

WDDGSYKYYGDSVKGRFTISRDNSKNTLYLQMNSLRAEDTAVYYCARDGIT

MVRGVMKDYFDYWGQGTLVTVSS (VL, EGFR binding arm)
SEQ ID NO: 14
AIQLTQSPSSLSASVGDRVTITCRASQDISSALVWYQQKPGKAPKLLIYDA

SSLESGVPSRFSGSESGTDFTLTISSLQPEDFATYYCQQFNSYPLTFGGGT

KVEIK (VH, c-Met binding arm)
SEQ ID NO: 15
QVQLVQSGAEVKKPGASVKVSCETSGYTFTSYGISWVRQAPGHGLEWMGWI

SAYNGYTNYAQKLQGRVTMTTDTSTSTAYMELRSLRSDDTAVYYCARDLRG

TNYFDYWGQGTLVTVSS (VL, c-Met binding arm)
SEQ ID NO: 16
DIQMTQSPSSVSASVGDRVTITCRASQGISNWLAWFQHKPGKAPKLLIYAA

SSLLSGVPSRFSGSGSGTDFTLTISSLQPEDFATYYCQQANSFPITFGQGT

RLEIK

HC1
SEQ ID NO: 17
QVQLVESGGGVVQPGRSLRLSCAASGFTFSTYGMHWVRQAPGKGLEWVAVI

WDDGSYKYYGDSVKGRFTISRDNSKNTLYLQMNSLRAEDTAVYYCARDGIT

MVRGVMKDYFDYWGQGTLVTVSSASTKGPSVFPLAPSSKSTSGGTAALGCL

VKDYFPEPVTVSWNSGALTSGVHTFPAVLQSSGLYSLSSVVTVPSSSLGTQ

TYICNVNHKPSNTKVDKRVEPKSCDKTHTCPPCPAPELLGGPSVFLFPPKP

KDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGK

LC1
SEQ ID NO: 18
AIQLTQSPSSLSASVGDRVTITCRASQDISSALVWYQQKPGKAPKLLIYDA

SSLESGVPSRFSGSESGTDFTLTISSLQPEDFATYYCQQFNSYPLTFGGGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC

HC2
SEQ ID NO: 19
QVQLVQSGAEVKKPGASVKVSCETSGYTFTSYGISWVRQAPGHGLEWMGWI

SAYNGYTNYAQKLQGRVTMTTDTSTSTAYMELRSLRSDDTAVYYCARDLRG

-continued

TNYFDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICNV

NHKPSNTKVDKRVEPKSCDKTHTCPPCPAPELLGGPSVFLFPPKPKDTLMI

SRTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFL

YSRLTVDKSRWQQGNVFSCSVMHEALHNHYTQKSLSLSPGK

LC2
SEQ ID NO: 20
DIQMTQSPSSVSASVGDRVTITCRASQGISNWLAWFQHKPGKAPKLLIYAA

SSLLSGVPSRFSGSGSGTDFTLTISSLQPEDFATYYCQQANSFPITFGQGT

RLEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC

Lazertinib is a 3$^{rd}$ generation EGFR tyrosine kinase inhibitor (TKI); the structure and synthesis of lazertinib is described in U.S. Pat. No. 9,593,098, which is incorporated by reference herein. The chemical name of the lazertinib free base, which is represented by formula (I) herein, is N-(5-(4-(4-((dimethylamino)methyl)-3-phenyl-1H-pyrazol-1-yl)pyrimidin-2-ylamino)-4-methoxy-2-morpholinophenyl)acrylamide (referred to herein as lazertinib). The mesylate salt of lazertinib may be represented by formula II:

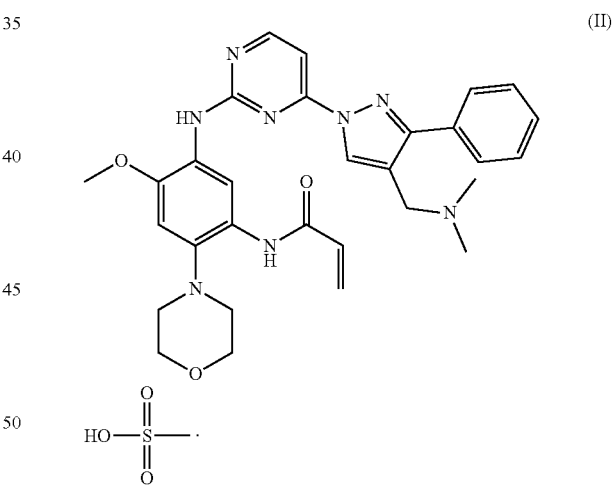

(II)

Embodiments of lazertinib (e.g., salts and crystalline forms) are described in PCT/KR2018/004473, which is also incorporated by reference herein.

According to particular embodiments, lazertinib in the form of a free base has little to no effect on wild-type EGFR, and is a highly selective and irreversible EGFR TKI with strong inhibitory activity against the single mutation of T790M and dual mutations; e.g., it targets the activating EGFR mutations del19 and L858R, as well as the T790M mutation. In one aspect of the invention, the mutation may be delE746-A750, L858R, or T790M, and it may be dual mutations selected from delE746-A750/T790M or L858R/T790M.

An embodiment of the disclosure provides a method of treating a subject having a cancer, comprising administering to the subject a combination therapy, wherein the combination therapy comprises a therapeutically effective amount of an isolated bispecific anti-epidermal growth factor receptor (EGFR)/hepatocyte growth factor receptor (c-Met) antibody and a therapeutically effective amount of a compound of formula (I)

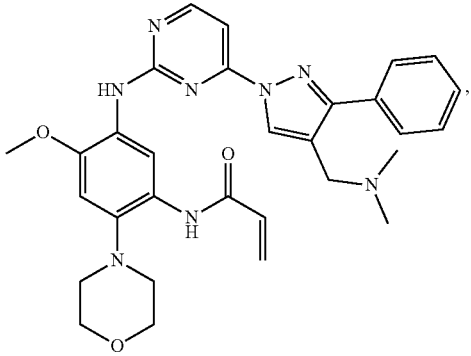

or solvate, hydrate, tautomer, or a pharmaceutically acceptable salt thereof.

An embodiment of the disclosure also provides a method of treating a subject having EGFR or c-Met expressing cancer, comprising administering to the subject a combination therapy, wherein the combination therapy comprises a therapeutically effective amount of an isolated bispecific anti-EGFR/c-Met antibody and a therapeutically effective amount of a compound of formula (I)

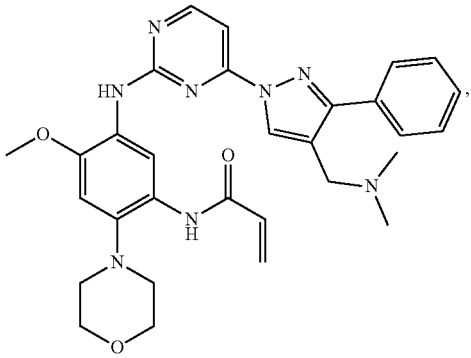

or solvate, hydrate, tautomer, or a pharmaceutically acceptable salt thereof.

An embodiment of the disclosure provides a pharmaceutical combination comprising a therapeutically effective amount of an isolated bispecific anti-epidermal growth factor receptor (EGFR)/hepatocyte growth factor receptor (c-Met) antibody and a therapeutically effective amount of a compound of formula (I)

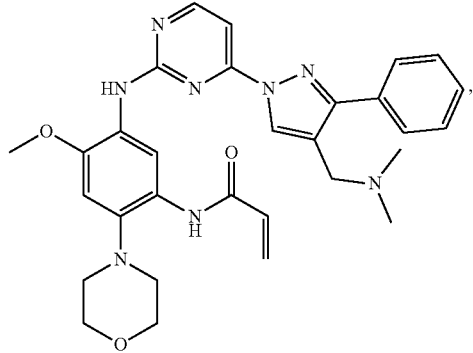

or solvate, hydrate, tautomer, or a pharmaceutically acceptable salt thereof, for use as a medicament, in particular for use as a medicament in a subject.

An embodiment of the disclosure provides a pharmaceutical combination comprising a therapeutically effective amount of an isolated bispecific anti-epidermal growth factor receptor (EGFR)/hepatocyte growth factor receptor (c-Met) antibody and a therapeutically effective amount of a compound of formula (I)

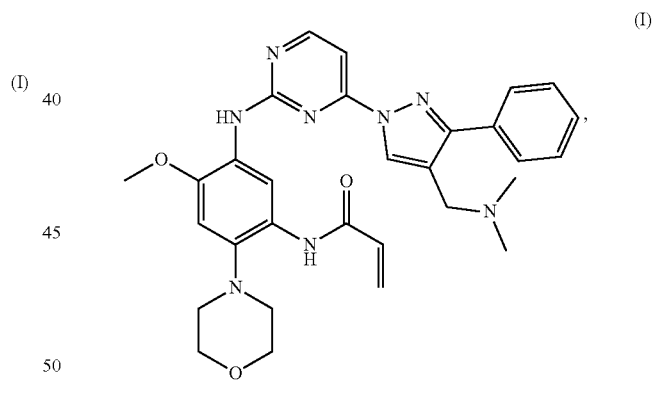

or solvate, hydrate, tautomer, or a pharmaceutically acceptable salt thereof, for use in the treatment of cancer, in particular for use in the treatment of cancer in a subject.

An embodiment of the disclosure provides a pharmaceutical combination comprising a therapeutically effective amount of an isolated bispecific anti-epidermal growth factor receptor (EGFR)/hepatocyte growth factor receptor (c-Met) antibody and a therapeutically effective amount of a compound of formula (I)

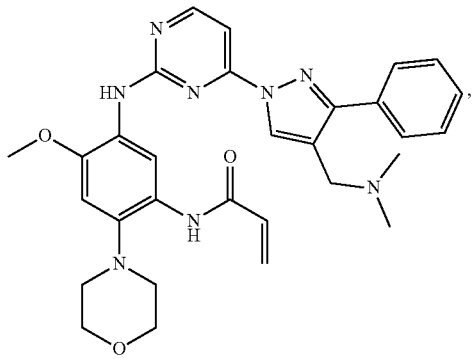

or solvate, hydrate, tautomer, or a pharmaceutically acceptable salt thereof, for use in the treatment of EGFR or c-Met expressing cancer, in particular for use in the treatment of EGFR or c-Met expressing cancer in a subject.

An embodiment of the disclosure provides use of a combination comprising a therapeutically effective amount of an isolated bispecific anti-epidermal growth factor receptor (EGFR)/hepatocyte growth factor receptor (c-Met) antibody and a therapeutically effective amount of a compound of formula (I)

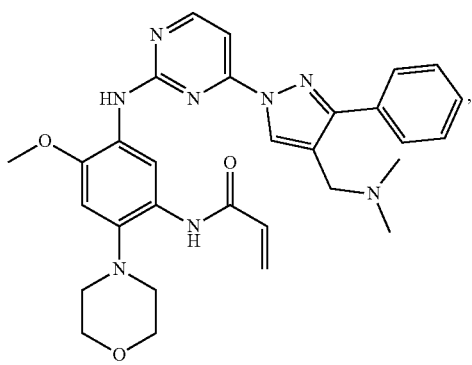

or solvate, hydrate, tautomer, or a pharmaceutically acceptable salt thereof, for the manufacture of a medicament for the treatment of cancer, in particular for the treatment of cancer in a subject.

An embodiment of the disclosure provides use of a combination comprising a therapeutically effective amount of an isolated bispecific anti-epidermal growth factor receptor (EGFR)/hepatocyte growth factor receptor (c-Met) antibody and a therapeutically effective amount of a compound of formula (I)

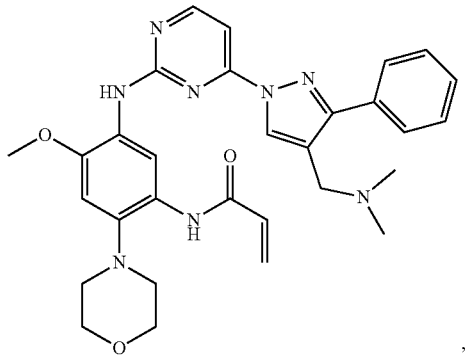

or solvate, hydrate, tautomer, or a pharmaceutically acceptable salt thereof, for the manufacture of a medicant for the treatment of EGFR or c-Met expressing cancer, in particular for the treatment of EGFR or c-Met expressing cancer in a subject.

An embodiment of the disclosure provides a pharmaceutical combination comprising a therapeutically effective amount of an isolated bispecific anti-epidermal growth factor receptor (EGFR)/hepatocyte growth factor receptor (c-Met) antibody and a therapeutically effective amount of a compound of formula (I)

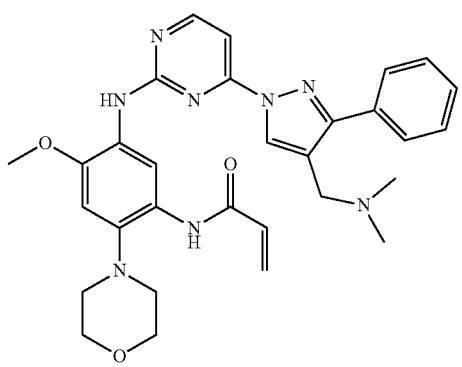

or solvate, hydrate, tautomer, or a pharmaceutically acceptable salt thereof.

An embodiment of the disclosure provides a product containing a therapeutically effective amount of an isolated bispecific anti-epidermal growth factor receptor (EGFR)/hepatocyte growth factor receptor (c-Met) antibody and a therapeutically effective amount of a compound of formula (I)

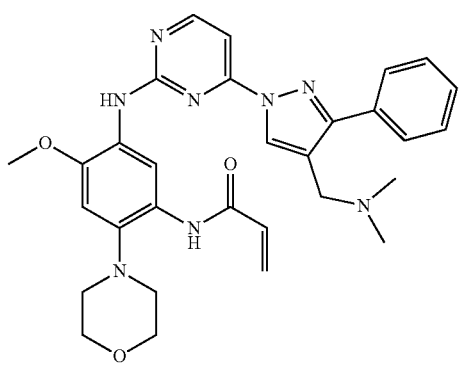

or solvate, hydrate, tautomer, or a pharmaceutically acceptable salt thereof, as a combined preparation for simultaneous, separate or sequential use in the treatment of cancer, in particular in the treatment of cancer in a subject.

An embodiment of the disclosure provides a product containing a therapeutically effective amount of an isolated bispecific anti-epidermal growth factor receptor (EGFR)/ hepatocyte growth factor receptor (c-Met) antibody and a therapeutically effective amount of a compound of formula (I)

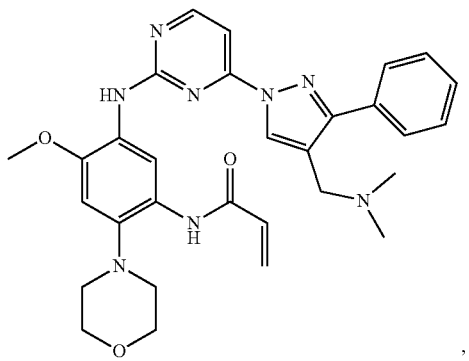

(I)

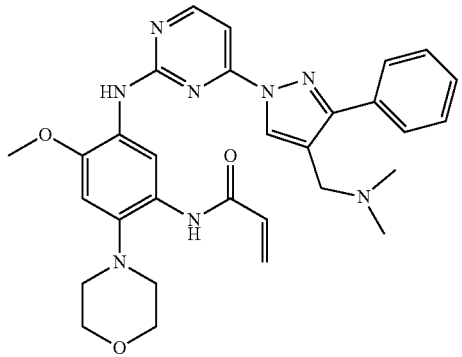

(I)

or solvate, hydrate, tautomer, or a pharmaceutically acceptable salt thereof, as a combined preparation for simultaneous, separate or sequential use in the treatment of EGFR or c-Met expressing cancer, in particular in the treatment of EGFR or c-Met expressing cancer in a subject.

An embodiment of the disclosure provides an isolated bispecific anti-epidermal growth factor receptor (EGFR)/hepatocyte growth factor receptor (c-Met) antibody, in particular a therapeutically effective amount of an isolated bispecific anti-epidermal growth factor receptor (EGFR)/hepatocyte growth factor receptor (c-Met) antibody, for use in combination with a compound of formula (I), in particular a therapeutically effective amount of a compound of formula (I),

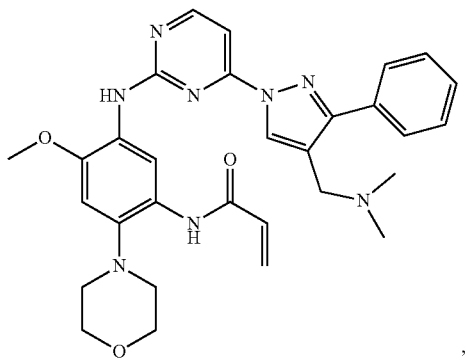

(I)

or solvate, hydrate, tautomer, or a pharmaceutically acceptable salt thereof, in the treatment of cancer, in particular in the treatment of cancer in a subject.

An embodiment of the disclosure provides an isolated bispecific anti-epidermal growth factor receptor (EGFR)/hepatocyte growth factor receptor (c-Met) antibody, in particular a therapeutically effective amount of an isolated bispecific anti-epidermal growth factor receptor (EGFR)/hepatocyte growth factor receptor (c-Met) antibody, for use in combination with a compound of formula (I), in particular a therapeutically effective amount of a compound of formula (I), or solvate, hydrate, tautomer, or a pharmaceutically acceptable salt thereof, in the treatment of EGFR or c-Met expressing cancer, in particular in the treatment of EGFR or c-Met expressing cancer in a subject.

In each embodiment, the bispecific anti-EGFR/c-Met antibody and the lazertinib compound, or solvate, hydrate, tautomer, or a pharmaceutically acceptable salt thereof, may be administered at the same time (e.g., as part of the same pharmaceutical composition, or in separate pharmaceutical compositions) or at different times, as described herein.

Pharmaceutically acceptable salt forms include pharmaceutically acceptable acidic/anionic or basic/cationic salts. Pharmaceutically acceptable acidic/anionic salts include acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, polygalacturonate, salicylate, stearate, subacetate, succinate, sulfate, hydrogensulfate, tannate, tartrate, teoclate, tosylate, and triethiodide salts. Pharmaceutically acceptable basic/cationic salts include, the sodium, potassium, calcium, magnesium, diethanolamine, N-methyl-D-glucamine, L-lysine, L-arginine, ammonium, ethanolamine, piperazine and triethanolamine salts.

A pharmaceutically acceptable acid salt is formed by reaction of the free base form of a compound of Formula (I) with a suitable inorganic or organic acid including, but not limited to, hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid. A pharmaceutically acceptable acid addition salt of a compound of Formula (I) can comprise or be, for example, a hydrobromide, hydrochloride, sulfate, nitrate, phosphate, succinate, maleate, formarate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g., 2-naphthalenesulfonate) or hexanoate salt.

The free acid or free base forms of the compound of formula (I) may be prepared from the corresponding base addition salt or acid addition salt form, respectively. For example a compound of the invention in an acid addition salt form may be converted to the corresponding free base form by treating with a suitable base (e.g., ammonium hydroxide solution, sodium hydroxide, and the like). A compound of the invention in a base addition salt form may be converted to the corresponding free acid by treating with a suitable acid (e.g., hydrochloric acid, etc.).

In some embodiments, the bispecific anti-EGFR/c-Met antibody comprises a first domain that binds EGFR comprising a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6 and a second domain that binds c-Met comprising the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12.

In some embodiments, the first domain that binds EGFR comprises a heavy chain variable region (VH) of SEQ ID NO: 13 and a light chain variable region (VL) of SEQ ID NO: 14 and the second domain that binds c-Met comprises the VH of SEQ ID NO: 15 and the VL of SEQ ID NO: 16.

In some embodiments, the bispecific anti-EGFR/c-Met antibody is an IgG1 isotype. Some variation exists within the IgG1 constant domain (e.g. well-known allotypes), with variation at positions 214, 356, 358, 422, 431, 435 o 436 (residue numbering according to the EU numbering) (see e.g. IMGT Web resources; IMGT Repertoire (IG and TR); Proteins and alleles; allotypes). The bispecific anti-EGFR/c-Met antibody may be any IgG1 allotype, such as G1m17, G1m3, G1m1, G1m2, G1m27 or G1m28. The amino acid sequence of an exemplary IgG1 constant domain is shown in SEQ ID NO: 21.

IgG1 constant domain
(SEQ ID NO: 21)
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVF

SCSVMHEALHNHYTQKSLSLSPGK

In some embodiments, the bispecific anti-EGFR/c-Met antibody comprises the HC1 of SEQ ID NO: 17, the LC1 of SEQ ID NO: 18, the HC2 of SEQ ID NO: 19 and the LC2 of SEQ ID NO: 20.

In some embodiments, the bispecific anti-EGFR/c-Met antibody has a biantennary glycan structure with a fucose content of about between 1% to about 15%.

In some embodiments, the bispecific anti-EGFR/c-Met antibody has a biantennary glycan structure with fucose content of about between 1% to about 15%, for example 15%, 14%, 13%, 12%, 11% 10%, 9%, 8%, 7%, 6%, 5%, 4%, 3%, 2% or 1%.

The relative amount of fucose is the percentage of fucose-containing structures related to all glycostructures. These may be characterized and quantified by multiple methods, for example: 1) using MALDI-TOF of N-glycosidase F treated sample (e.g. complex, hybrid and oligo- and high-mannose structures) as described in Int Pat. Publ. No. WO2008/077546 2); 2) by enzymatic release of the Asn297 glycans with subsequent derivatization and detection/quantitation by HPLC (UPLC) with fluorescence detection and/or HPLC-MS (UPLC-MS); 3) intact protein analysis of the native or reduced mAb, with or without treatment of the Asn297 glycans with Endo S or other enzyme that cleaves between the first and the second GlcNAc monosaccharides, leaving the fucose attached to the first GlcNAc; 4) digestion of the mAb to constituent peptides by enzymatic digestion (e.g., trypsin or endopeptidase Lys-C), and subsequent separation, detection and quantitation by HPLC-MS (UPLC-MS); 5) Separation of the mAb oligosaccharides from the mAb protein by specific enzymatic deglycosylation with PNGase F at Asn 297. The oligosaccharides thus released can be labeled with a fluorophore, separated and identified by various complementary techniques which allow: fine characterization of the glycan structures by matrix-assisted laser desorption ionization (MALDI) mass spectrometry by comparison of the experimental masses with the theoretical masses, determination of the degree of sialylation by ion exchange HPLC (GlycoSep C), separation and quantification of the oligosacharride forms according to hydrophilicity criteria by normal-phase HPLC (GlycoSep N), and separation and quantification of the oligosaccharides by high performance capillary electrophoresis-laser induced fluorescence (HPCE-LIF).

The ability of antibodies to induce ADCC can be enhanced by engineering their oligosaccharide component. Human IgG1 or IgG3 are N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides enhances antibody-dependent cell-mediated cytotoxicity (ADCC) of antibodies via improved FcγRIIIa binding without altering antigen binding or complement dependent cytotoxicity (CDC) activity. Antibodies with reduced fucose content can be made using different methods reported to lead to the successful expression of relatively high defucosylated antibodies bearing the biantennary complex-type of Fc oligosaccharides such as control of culture osmolality (Konno et al., Cytotechnology 64:249-65, 2012), application of a variant CHO line Lec13 as the host cell line (Shields et al., J Biol Chem 277:26733-26740, 2002), application of a variant CHO line EB66 as the host cell line (Olivier et al., MAbs; 2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the α 1,6-fucosyltransferase (FUT8) gene (Mori et al., Biotechnol Bioeng 88:901-908, 2004), or coexpression of β-1,4-N-acetylglucosaminyltransferase III and Golgi α-mannosidase II or a potent alpha-mannosidase I inhibitor, kifunensine (Ferrara et al., Biotechnol Bioeng 93:851-861, 2006; Xhou et al., Biotechnol Bioeng 99:652-65, 2008).

In some embodiments, the compound of formula (I) or solvate, hydrate, tautomer, or a pharmaceutically acceptable salt thereof is represented by a compound of formula (II)

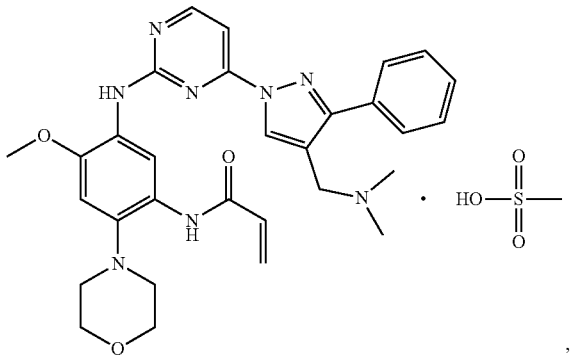

(II), a solvate, hydrate, or tautomer thereof. In some embodiments, the compound of formula (I) or solvate, hydrate, tautomer, or a pharmaceutically acceptable salt thereof is represented by a compound of formula (II)

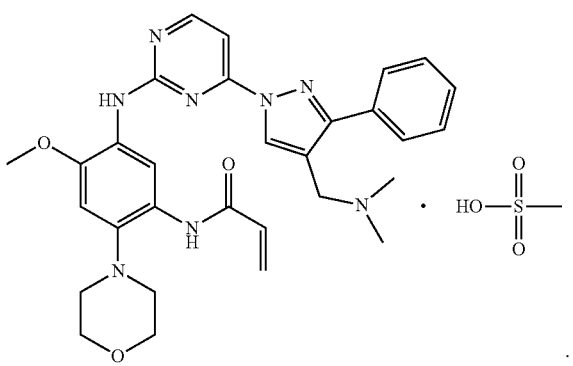

In some embodiments, the cancer is EGFR or c-Met expressing cancer.

In some embodiments, the cancer is EGFR and c-Met expressing cancer.

In some embodiments, the cancer is EGFR expressing cancer.

In some embodiments, the cancer is c-Met expressing cancer.

In some embodiments, the EGFR or c-Met expressing cancer is associated with a wild-type EGFR, an EGFR mutation, an EGFR gene amplification, increased levels of circulating HGF, a wild-type c-Met, a c-Met mutation, a c-Met gene amplification or a mutant KRAS. The EGFR mutation may be an activating mutation such as exon 19 deletion or L858R mutation.

Exemplary EGFR mutations, such as EGFR activating mutations that may be associated with cancer include point mutations, deletion mutations, insertion mutations, inversions or gene amplifications that lead to an increase in at least one biological activity of EGFR, such as elevated tyrosine kinase activity, formation of receptor homodimers and heterodimers, enhanced ligand binding etc. Mutations can be located in any portion of an EGFR gene or regulatory region associated with an EGFR gene and include mutations in exon 18, 19, 20 or 21. Other examples of EGFR activating mutations are known in the art (see e.g., U.S. Pat. Publ. No. US2005/0272083). Information about EGFR and other ErbB receptors including receptor homo- and hetero-dimers, receptor ligands, autophosphorylation sites, and signaling molecules involved in ErbB mediated signaling is known in the art (see e.g., Hynes and Lane, Nature Reviews Cancer 5: 341-354, 2005).

In some embodiments, the EGFR mutation is E709K, L718Q, L718V, G719A, G719X, G724X, G724S, I744T, E746K, L747S, E749Q, A750P, A755V, V765M, C775Y, T790M, L792H, L792V, G796S, G796R, G796C, C797S, T854I, L858P, L858R, L861X, delE746-A750, delE746_T751InsKV, delE746_A750InsHS, delE746_T751InsFPT, delE746_T751InsL, delE746_S752InsIP, delE746_P753InsMS, delE746_T751InsA, delE746_T751InsAPT, delE746_T751InsVA, delE746_S752InsV, delE746_P753InsVS, delE746_K754InsGG, delE746_E749, delE746_E749InsP, delL747_E749, delL747_A750InsP, delL747_T751InsP, delL747_T751InsN, delL747_S752InsPT, delL747_P753InsNS, delL747_S752InsPI, delL747_S752, delL747_P753InsS, delL747_K754, delL747_T751InsS, delL747_T751, delL747_P753InsS, delA750_I759InsPT, delT751_I759InsT, delS752_I759, delT751_I759InsN, delT751_D761InsNLY, delS752_I759, delR748-P753, delL747-P753insS, delL747-T751, M766_A767InsA, S768_V769InsSVA, P772_H773InsNS, D761_E762InsX, A763_Y764InsX, Y764_Y765 InsX, M766_A767InsX, A767_V768 InsX, S768_V769 InsX, V769_D770 InsX, D770_N771 InsX, N771_P772 InsX, P772_H773 InsX, H773_V774 InsX, V774_C775 InsX, one or more deletions in EGFR exon 20, or one or more insertions in EGFR exon 20, one or more deletions in EGFR exon 19, or one or more insertions in EGFR exon 19, or any combinations thereof, wherein X refers to any of the naturally occurring amino acids and can be one to seven amino acids long. The nomenclature of the mutations is well-known.

In some embodiments, the EGFR mutation is one or more deletions in exon 19 or L858R or any combination thereof. Exemplary exon 19 deletions are delE746-A750, delE746_T751InsKV, delE746_A750InsHS, delE746_T751InsFPT, delE746_T751InsL, delE746_S752InsIP, delE746_P753InsMS, delE746_T751InsA, delE746_T751InsAPT, delE746_T751InsVA, delE746_S752InsV, delE746_P753InsVS, delE746_K754InsGG, delE746_E749, delE746_E749InsP, delL747_E749, delL747_A750InsP, delL747_T751InsP, delL747_T751InsN, delL747_S752InsPT, delL747_P753InsNS, delL747_S752InsPI, delL747_S752, delL747_P753InsS, delL747_K754, delL747_T751InsS, delL747_T751, delL747_P753InsS, delA750_I759InsPT, delT751_I759InsT, delS752_I759, delT751_I759InsN, delT751_D761InsNLY, delS752_I759, delR748-P753 and delL747-P753insS, delL747-T751.

Exemplary c-Met mutations include point mutations, deletion mutations, insertion mutations, inversions or gene amplifications that lead to an increase in at least one biological activity of a c-Met protein, such as elevated tyrosine kinase activity, formation of receptor homodimers and heterodimers, enhanced ligand binding etc. Mutations can be located in any portion of the c-Met gene or regulatory regions associated with the gene, such as mutations in the kinase domain of c-Met. Exemplary c-Met mutations are mutations at residue positions N375, V13, V923, R175, V136, L229, S323, R988, S1058/T1010 and E168, or exon 14 skipping mutations.

In some embodiments, the c-Met mutation is c-Met exon 14 skipping mutation.

Methods for detecting EGFR and c-Met mutations or gene amplifications are well known.

In some embodiments, the cancer is KRAS mutant. Exemplary KRAS mutations include G12V, G12C or G12A substitution.

In some embodiments, the subject has been diagnosed with the EGFR mutation prior to administering the combination therapy.

In some embodiments, the subject has a newly diagnosed cancer.

In some embodiments, the subject has a newly diagnosed EGFR or c-Met expressing cancer.

In some embodiments, the subject has a newly diagnosed EGFR and c-Met expressing cancer.

In some embodiments, the subject has a newly diagnosed EGFR expressing cancer.

In some embodiments, the subject has a newly diagnosed c-Met expressing cancer.

In some embodiments, the subject having the newly diagnosed cancer has one or more EGFR exon 20 mutations. In some embodiments, the subject having the newly diagnosed EGFR or c-Met expressing cancer has one or more EGFR exon 20 mutations. Exon 20 mutations (insertion of one or more amino acids are generally resistant to EGFR tyrosine kinase inhibitors (TKI) (see. e.g. Int. Pat. Publ. No. WO2018/094225). Exemplary exon 20 mutations include M766_A767InsA, S768_V769InsSVA, P772_H773InsNS, D761_E762InsX, A763_Y764InsX, Y764_Y765 InsX, M766_A767InsX, A767_V768 InsX, S768_V769 InsX, V769_D770 InsX, D770_N771 InsX, N771_P772 InsX, P772_H773 InsX, H773_V774 InsX, and V774_C775 InsX, wherein X is one to seven amino acids.

In some embodiments, the subject is resistant to treatment with poziotinib.

In some embodiments, the subject is tyrosine kinase inhibitor (TKI) treatment naïve.

In some embodiments, the subject is EGFR tyrosine kinase inhibitor (TKI) treatment naïve.

In some embodiments, the subject is resistant or relapsed to treatment with a first generation EGFR TKI.

In some embodiments, the first generation EGFR TKI is erlotinib or gefitinib.

In some embodiments, the subject is resistant or relapsed to treatment with a second generation EGFR TKI.

In some embodiments, the second generation EGFR TKI is afatinib.

In some embodiments, the subject is resistant or relapsed to treatment with a third generation EGFR TKI.

In some embodiments, the third generation EGFR TKI is osimertinib.

In some embodiments, the subject is resistant or has acquired resistance to treatment with a prior anti-cancer therapy.

In some embodiments, the prior anti-cancer therapy is chemotherapy, a targeted anti-cancer therapy or a kinase inhibitor.

In some embodiments, the TKI is an inhibitor of EGFR, c-Met, HER2, HER3, HER4, VEGFR or AXL.

In some embodiments, the TKI is erlotinib, gefitinib, lapatinib, vandetanib, afatinib, osimertinib, poziotinib, criotinib, cabozantinib, capmatinib, axitinib, lenvatinib, nintedanib, regorafenib, pazopanib, sorafenib or sunitinib.

In some embodiments, the subject is resistant or has acquired resistance to an EGFR inhibitor. Exemplary EGFR inhibitors for which cancer may acquire resistance are anti-EGFR antibodies cetuximab (ERBITUX®), pantinumumab (VECTIBIX®), matuzumab, nimotuzumab, small molecule EGFR inhibitors erlotinib (TARCEVA®), gefitinib (IRESSA®), EKB-569 (pelitinib, irreversible EGFR TKI), pan-ErbB and other receptor tyrosine kinase inhibitors, lapatinib (EGFR and HER2 inhibitor), pelitinib (EGFR and HER2 inhibitor), vandetanib (ZD6474, ZACTIMA™, EGFR, VEGFR2 and RET TKI), PF00299804 (dacomitinib, irreversible pan-ErbB TKI), CI-1033 (irreversible pan-erbB TKI), afatinib (BIBW2992, irreversible pan-ErbB TKI), AV-412 (dual EGFR and ErbB2 inhibitor), EXEL-7647 (EGFR, ErbB2, GEVGR and EphB4 inhibitor), CO-1686 (irreversible mutant-selective EGFR TKI), AZD9291 (irreversible mutant-selective EGFR TKI), and HKI-272 (neratinib, irreversible EGFR/ErbB2 inhibitor).

Various qualitative and/or quantitative methods may be used to determine if a subject is resistant, has developed or is susceptible to developing a resistance to treatment with an anti-cancer therapy. Symptoms that may be associated with resistance to an anti-cancer therapy include a decline or plateau of the well-being of the patient, an increase in the size of a tumor, arrested or slowed decline in growth of a tumor, and/or the spread of cancerous cells in the body from one location to other organs, tissues or cells. Re-establishment or worsening of various symptoms associated with cancer may also be an indication that a subject has developed or is susceptible to developing resistance to an anti-cancer therapy, such as anorexia, cognitive dysfunction, depression, dyspnea, fatigue, hormonal disturbances, neutropenia, pain, peripheral neuropathy, and sexual dysfunction. The symptoms associated with cancer may vary according to the type of cancer. For example, symptoms associated with cervical cancer may include abnormal bleeding, unusual heavy vaginal discharge, pelvic pain that is not related to the normal menstrual cycle, bladder pain or pain during urination, and bleeding between regular menstrual periods, after sexual intercourse, douching, or pelvic exam. Symptoms associated with lung cancer may include persistent cough, coughing up blood, shortness of breath, wheezing chest pain, loss of appetite, losing weight without trying and fatigue. Symptoms for liver cancer may include loss of appetite and weight, abdominal pain, especially in the upper right part of abdomen that may extend into the back and shoulder, nausea and vomiting, general weakness and fatigue, an enlarged liver, abdominal swelling (ascites), and a yellow discoloration of the skin and the whites of eyes (jaundice). One skilled in oncology may readily identify symptoms associated with a particular cancer type.

In some embodiments, the cancer is a non-small cell lung cancer (NSCLC), an epithelial cell cancer, a breast cancer, an ovarian cancer, a lung cancer, a lung adenocarcinoma, a squamous ell lung cancer, a small cell lung cancer, a colorectal cancer, an anal cancer, a prostate cancer, a kidney cancer, a bladder cancer, a head and neck cancer, a pharynx cancer, a cancer of the nose, a pancreatic cancer, a skin cancer, an oral cancer, a cancer of the tongue, an esophageal cancer, a vaginal cancer, a cervical cancer, a cancer of the spleen, a testicular cancer, a gastric cancer, a cancer of the thymus, a colon cancer, a thyroid cancer, a liver cancer, a hepatocellular carcinoma (HCC) or sporadic or hereditary papillary renal cell carcinoma (PRCC). In some embodiments, the cancer is a metastatic cancer.

In some embodiments, the cancer is the NSCLC. In some embodiments, the cancer is the epithelial cell cancer. In some embodiments, the cancer is the breast cancer. In some embodiments, the cancer is the ovarian cancer. In some embodiments, the cancer is the lung cancer. In some embodiments, the cancer is the lung adenocarcinoma. In some embodiments, the cancer is the squamous cell lung cancer. In some embodiments, the cancer is the small cell lung cancer. In some embodiments, the cancer is the colorectal cancer. In some embodiments, the cancer is the anal cancer. In some embodiments, the cancer is the prostate cancer. In some embodiments, the cancer is the kidney cancer. In some embodiments, the cancer is the bladder cancer. In some embodiments, the cancer is the head and neck cancer. In some embodiments, the cancer is the pharynx cancer. In some embodiments, the cancer is the cancer of the nose. In some embodiments, the cancer is the pancreatic cancer. In some embodiments, the cancer is the skin cancer. In some embodiments, the cancer is the oral cancer. In some embodiments, the cancer is the cancer of the tongue. In some embodiments, the cancer is the esophageal cancer. In some embodiments, the cancer is the vaginal cancer. In some embodiments, the cancer is the cervical cancer. In some embodiments, the cancer is the cancer of the spleen. In some embodiments, the cancer is the testicular cancer. In some embodiments, the cancer is the gastric cancer. In some embodiments, the cancer is the cancer of the thymus. In some embodiments, the cancer is the colon cancer. In some embodiments, the cancer is the thyroid cancer. In some embodiments, the cancer is the liver cancer. In some embodiments, the cancer is the HCC. In some embodiments, the cancer is the PRCC.

In some embodiments, the NSCLC includes squamous cell carcinoma, adenocarcinoma, and large cell carcinoma. In some embodiments, cells of the NSCLC have an epithelial phenotype. In some embodiments, the NSCLC has acquired resistance to treatment with one or more EGFR inhibitors.

In NSCLC, specific mutations in the EGFR gene are associated with high response rates (70-80%) to EGFR tyrosine kinase inhibitors (EGFR-TKIs). A 5 amino acid deletion in exon 19 or the point mutation L858R in EGFR are associated with EGFR-TKI sensitivity (Nakata and Gotoh, Expert Opin Ther Targets 16:771-781, 2012). These mutations result in a ligand-independent activation of the EGFR kinase activity. Activating EGFR mutations occur in 10-30% of NSCLC patients and are significantly more common in East Asians, women, never smokers, and patients with adenocarcinoma histology (Janne and Johnson Clin Cancer Res 12(14 Suppl): 4416s-4420s, 2006). EGFR gene amplification is also strongly correlated with response after EGFR-TKI treatment (Cappuzzo et al., J Natl Cancer Inst 97:643-55, 2005). EGFR exon 20 insertions have been associated with EGFR TKI resistance.

Although the majority of NSCLC patients with EGFR mutations initially respond to EGFR TKI therapy, virtually all acquire resistance that prevents a durable response. 50-60% of patients acquire resistance due to a second-site point mutation in the kinase domain of EGFR (T790M). Nearly 60% of all tumors that become resistant to EGFR tyrosine kinase inhibitors increase c-Met expression, amplify the c-Met gene, or increase its only known ligand, HGF (Turke et al., Cancer Cell, 17:77-88, 2010).

In some embodiments, the bispecific anti-EGFR/c-Met antibody is administered at a dose of between about 200 mg and about 2000 mg.

In some embodiments, the bispecific anti-EGFR/c-Met antibody is administered at a dose of between about 350 mg and about 1400 mg.

In some embodiments, the bispecific anti-EGFR/c-Met antibody is administered at a dose of about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, about 910 mg, about 920 mg, about 930 mg, about 940 mg, about 950 mg, about 960 mg, about 970 mg, about 980 mg, about 990 mg, about 1000 mg, about 1010 mg, about 1020 mg, about 1030 mg, about 1040 mg, about 1050 mg, about 1060 mg, about 1070 mg, about 1080 mg, about 1090 mg, about 1100 mg, about 1110 mg, about 1120 mg, about 1130 mg, about 1140 mg, about 1150 mg, about 1160 mg, about 1170 mg, about 1180 mg, about 1190 mg, about 1200 mg, about 1210 mg, about 1220 mg, about 1230 mg, about 1240 mg, about 1250 mg, about 1260 mg, about 1270 mg, about 1280 mg, about 1290 mg, about 1300 mg, about 1310 mg, about 1320 mg, about 1330 mg, about 1340 mg, about 1350 mg, about 1360 mg, about 1370 mg, about 1380 mg, about 1390 mg, about 1400 mg, about 1410 mg, about 1420 mg, about 1430 mg, about 1440 mg, about 1450 mg, about 1460 mg, about 1470 mg, about 1480 mg, about 1490 mg, about 1500 mg, about 1510 mg, about 1520 mg, about 1530 mg, about 1540 mg, about 1550 mg, about 1560 mg, about 1570 mg, about 1580 mg, about 1590 mg, about 1600 mg, about 1610 mg, 1620 mg, about 1630 mg, about 1640 mg, about 1650 mg, about 1660 mg, about 1670 mg, about 1680 mg, about 1690 mg, about 1700 mg, about 1710 mg, about 1720 mg, about 1730 mg, about 1740 mg, about 1750 mg, about 1760 mg, about 1770 mg, about 1780 mg, about 1790 mg, about 1800 mg, about 1810 mg, about 1820 mg, about 1830 mg, about 1840 mg, about 1850 mg, about 1860 mg, about 1870 mg, about 1880 mg, 1890 mg, about 1900 mg, about 1910 mg, about 1920 mg, about 1930 mg, about 1940 mg, about 1950 mg, about 1960 mg, about 1970 mg, about 9810 mg, about 1990 mg or about 2000 mg.

In some embodiments, the bispecific anti-EGFR/c-Met antibody is administered at a dose of about 350 mg, about 700 mg, about 1050 mg or about 1400 mg. In some embodiments, the bispecific anti-EGFR/c-Met antibody is administered at a dose of about 350 mg. In some embodiments, the bispecific anti-EGFR/c-Met antibody is administered at a dose of about 700 mg. In some embodiments, the bispecific anti-EGFR/c-Met antibody is administered at a dose of about 1050 mg. In some embodiments, the bispecific anti-EGFR/c-Met antibody is administered at a dose of about 1400 mg.

In some embodiments, the bispecific anti-EGFR/c-Met antibody is administered once a week.

In some embodiments, the bispecific anti-EGFR/c-Met antibody is administered once in two weeks.

In some embodiments, the compound of formula (I) or solvate, hydrate, tautomer, or a pharmaceutically acceptable salt thereof (e.g., the compound of formula (II), the mesylate salt of lazertinib) is administered at a dose of between about 20 mg and about 320 mg. Doses of the compound of formula (I) or solvate, hydrate, tautomer, or a pharmaceutically acceptable salt thereof described herein refer to the amount of free base of the compound of formula (I) in the dose (e.g., the dose amounts in Examples 3-5 refer to the amount of Lazertinib). For example, according to embodiments in which the dose comprises the mesylate salt of lazertinib (compound of formula (II)), the dose refers to the amount of lazertinib free base (compound of formula (I)); for example, as shown in Table 1 of mg/dose:

TABLE 1

| Lazertinib mesylate (as Lazertinib) | 117.33 (100.00) | 140.79 (120.00) | 187.72 (160.00) | 281.58 (240.00) | 375.44 (320.00) |
|---|---|---|---|---|---|

In some embodiments, the compound of formula (I) or solvate, hydrate, tautomer, or a pharmaceutically acceptable salt thereof is administered at a dose of between about 40 mg and about 320 mg. In some embodiments, the compound of formula (I) or solvate, hydrate, tautomer, or a pharmaceutically acceptable salt thereof is administered at a dose of between about 80 mg and about 320 mg. In some embodiments, the compound of formula (I) or solvate, hydrate, tautomer, or a pharmaceutically acceptable salt thereof is administered at a dose of between about 160 mg and about 320 mg. In some embodiments, the compound of formula (I) or solvate, hydrate, tautomer, or a pharmaceutically acceptable salt thereof is administered at a dose of between about 240 mg and about 320 mg. In some embodiments, the compound of formula (I) or solvate, hydrate, tautomer, or a pharmaceutically acceptable salt thereof is administered at a dose of between about 20 mg and about 240 mg. In some embodiments, the compound of formula (I) or solvate, hydrate, tautomer, or a pharmaceutically acceptable salt thereof is administered at a dose of between about 40 mg and about 240 mg. In some embodiments, the compound of formula (I) or solvate, hydrate, tautomer, or a pharmaceutically acceptable salt thereof is administered at a dose of between about 80 mg and about 240 mg. In some embodiments, the compound of formula (I) or solvate, hydrate, tautomer, or a pharmaceutically acceptable salt thereof is administered at a dose of between about 100 mg and about 300 mg. In some embodiments, the compound of formula (I) or solvate, hydrate, tautomer, or a pharmaceutically acceptable salt thereof is administered at a dose of between about 160 mg and about 240 mg. In some embodiments, the compound of formula (I) or solvate, hydrate, tautomer, or a pharmaceutically acceptable salt thereof is administered at a dose of between about 100 mg and about 300 mg.

In some embodiments, the compound of formula (I) or solvate, hydrate, tautomer, or a pharmaceutically acceptable salt thereof (e.g., the compound of formula (II), the mesylate salt of lazertinib), is administered at a dose of at least about 20 mg, at least about 40 mg, at least about 60 mg, at least about 80 mg, at least about 100 mg, at least about 120 mg, at least about 140 mg, at least about 160 mg, at least about 180 mg, at least about 200 mg, at least about 220 mg, at least about 240 mg, at least about 260 mg, at least about 280 mg, at least about 300 mg, or at least about 320 mg.

In some embodiments, the compound of formula (I) or solvate, hydrate, tautomer, or a pharmaceutically acceptable salt thereof (e.g., the compound of formula (II), the mesylate salt of lazertinib) is administered at a dose of about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg or about 320 mg.

In some embodiments, the compound of formula (I) or solvate, hydrate, tautomer, or a pharmaceutically acceptable salt thereof (e.g., the compound of formula (II), the mesylate salt of lazertinib) is administered once a day.

In some embodiments, the compound of formula (I) or solvate, hydrate, tautomer, or a pharmaceutically acceptable salt thereof (e.g., the compound of formula (II), the mesylate salt of lazertinib) is administered at a dose of between about 20 mg and about 320 mg daily (e.g., about 240 mg daily).

In some embodiments, the compound of formula (I) or solvate, hydrate, tautomer, or a pharmaceutically acceptable salt thereof (e.g., the compound of formula (II), the mesylate salt of lazertinib) is administered at a dose of between about 160 mg and about 240 mg daily.

In some embodiments, the bispecific anti-EGFR/c-Met antibody is administered at a dose of between about 200 mg and about 2000 mg weekly for four weeks and once in two weeks thereafter, and the compound of formula (I) or solvate, hydrate, tautomer, or a pharmaceutically acceptable salt thereof is administered at any of the doses described herein, e.g., a dose of between about 20 mg and about 320 mg daily (e.g., about 240 mg daily).

In some embodiments, the bispecific anti-EGFR/c-Met antibody is administered at a dose of between about 200 mg and about 2000 mg weekly for four weeks and once in two weeks thereafter, and the compound of formula (II) or solvate, hydrate, or tautomer thereof is administered at any of the doses described herein, e.g., a dose of between about 20 mg and about 320 mg daily (e.g., about 240 mg daily).

In some embodiments, the bispecific anti-EGFR/c-Met antibody is administered at a dose of between about 350 mg and about 1400 mg weekly for four weeks and once in two weeks thereafter, and the compound of formula (I) or solvate, hydrate, tautomer, or a pharmaceutically acceptable salt thereof is administered at any of the doses described herein, e.g., a dose of between about 160 mg and about 240 mg daily (e.g., about 240 mg daily).

In some embodiments, the bispecific anti-EGFR/c-Met antibody is administered at a dose of between about 350 mg and about 1400 mg weekly for four weeks and once in two weeks thereafter, and the compound of formula (II) or solvate, hydrate, or tautomer thereof is administered at any of the doses described herein, e.g., a dose of between about 160 mg and about 240 mg daily (e.g., about 240 mg daily).

In some embodiments, the bispecific anti-EGFR/c-Met antibody is administered at a dose of about 700 mg weekly for four weeks and once in two weeks thereafter, and the compound of formula (I) or solvate, hydrate, tautomer, or a pharmaceutically acceptable salt thereof is administered at a dose of about 160 mg daily.

In some embodiments, the bispecific anti-EGFR/c-Met antibody is administered at a dose of about 700 mg weekly for four weeks and once in two weeks thereafter, and the compound of formula (II) or solvate, hydrate, or tautomer thereof is administered at a dose of about 160 mg daily.

In some embodiments, the bispecific anti-EGFR/c-Met antibody is administered at a dose of about 1050 mg weekly for four weeks and once in two weeks thereafter, and the compound of formula (I) or solvate, hydrate, tautomer, or a pharmaceutically acceptable salt thereof is administered at a dose of about 160 mg daily.

In some embodiments, the bispecific anti-EGFR/c-Met antibody is administered at a dose of about 1050 mg weekly for four weeks and once in two weeks thereafter, and the compound of formula (II) or solvate, hydrate, or tautomer thereof is administered at a dose of about 160 mg daily.

In some embodiments, the bispecific anti-EGFR/c-Met antibody is administered at a dose of about 1400 mg weekly for four weeks and once in two weeks thereafter, and the compound of formula (I) or solvate, hydrate, tautomer, or a pharmaceutically acceptable salt thereof is administered at a dose of about 160 mg daily.

In some embodiments, the bispecific anti-EGFR/c-Met antibody is administered at a dose of about 1400 mg weekly for four weeks and once in two weeks thereafter, and the compound of formula (II) or solvate, hydrate, or tautomer thereof is administered at a dose of about 160 mg daily.

In some embodiments, the bispecific anti-EGFR/c-Met antibody is administered at a dose of about 700 mg weekly for four weeks and once in two weeks thereafter, and the compound of formula (I) or solvate, hydrate, tautomer, or a pharmaceutically acceptable salt thereof is administered at a dose of about 240 mg daily.

In some embodiments, the bispecific anti-EGFR/c-Met antibody is administered at a dose of about 700 mg weekly for four weeks and once in two weeks thereafter, and the compound of formula (II) or solvate, hydrate, or tautomer thereof is administered at a dose of about 240 mg daily.

In some embodiments, the bispecific anti-EGFR/c-Met antibody is administered at a dose of about 1050 mg weekly for four weeks and once in two weeks thereafter, and the compound of formula (I) or solvate, hydrate, tautomer, or a pharmaceutically acceptable salt thereof is administered at a dose of about 240 mg daily.

In some embodiments, the bispecific anti-EGFR/c-Met antibody is administered at a dose of about 1050 mg weekly for four weeks and once in two weeks thereafter, and the compound of formula (II) or solvate, hydrate, or tautomer thereof is administered at a dose of about 240 mg daily.

In some embodiments, the bispecific anti-EGFR/c-Met antibody is administered at a dose of about 1400 mg weekly for four weeks and once in two weeks thereafter, and the compound of formula (I) or solvate, hydrate, tautomer, or a pharmaceutically acceptable salt thereof is administered at a dose of about 240 mg daily.

In some embodiments, the bispecific anti-EGFR/c-Met antibody is administered at a dose of about 1400 mg weekly for four weeks and once in two weeks thereafter, and the compound of formula (II) or solvate, hydrate, or tautomer thereof is administered at a dose of about 240 mg daily.

According to particular embodiments, a method of treating a patient with lazertinib in combination with JNJ-61186372, or lazertinib in combination with JNJ-61186372 for use as described herein, in accordance with a dosing regimen as described herein (e.g., as described above and in Example 3), is effective in reducing the patient's tumor volume (see, e.g., Example 4). For example, such effect may be observed in patients diagnosed with NSCLC with EGFR T790M negative disease after progression on 1st generation TKI, and in patients with progression after prior 3rd generation TKI therapy.

In some embodiments, the subject is homozygous for phenylalanine at position 158 of CD16 or heterozygous for valine and phenylalanine at position 158 of CD16.

Subject homozygous for phenylalanine at position 158 of CD16 has a FcγRIIIa-158F/F genotype. Subject heterozygous for valine and pheynylalanine at position 158 of CD16 has a FcγRIIIa-158F/V genotype. CD16 is also known as the Fc gamma receptor IIIa (FcγRIIIa) or the low affinity immunoglobulin gamma Fc region receptor III-A isoform. Valine/phenylalanine (V/F) polymorphism at FcγRIIIa protein residue position 158 has been shown to affect FcγRIIIa affinity to human IgG. Receptor with FcγRIIIa-158F/F or FcγRIIIa-158F/V polymorphisms demonstrates reduced Fc engagement and therefore reduced ADCC when compared to the FcγRIIIa-158V/V. The bispecific anti-EGFR/c-Met antibody having reduced fucose content may be more efficacious in the treatment of patients with FcγRIIIa-158F/F or FcγRIIIa-158F/V genotypes. Patients can be analyzed for their FcγRIIIa polymorphism using routine methods.

In some embodiments, the subject is further administered a third anti-cancer therapy.

In some embodiments, the third anti-cancer therapy is chemotherapy, a targeted anti-cancer therapy or a kinase inhibitor.

In some embodiments, the kinase inhibitor is an inhibitor of EGFR, c-Met, HER2, HER3, HER4, VEGFR or AXL. In some embodiments, the kinase inhibitor is an inhibitor of EGFR. In some embodiments, the kinase inhibitor is an inhibitor of c-Met. In some embodiments, the kinase inhibitor is an inhibitor of HER2. In some embodiments, the kinase inhibitor is an inhibitor of HER3. In some embodiments, the kinase inhibitor is an inhibitor of HER4. In some embodiments, the kinase inhibitor is an inhibitor of VEGFR. In some embodiments, the kinase inhibitor is an inhibitor of or AXL.

In some embodiments, the kinase inhibitor is erlotinib, gefitinib, lapatinib, vandetanib, afatinib, osimertinib, poziotinib, criotinib, cabozantinib, capmatinib, axitinib, lenvatinib, nintedanib, regorafenib, pazopanib, sorafenib or sunitinib.

In some embodiments, the kinase inhibitor is erlotinib. In some embodiments, the kinase inhibitor is gefitinib. In some embodiments, the kinase inhibitor is lapatinib. In some embodiments, the kinase inhibitor is vandetanib. In some embodiments, the kinase inhibitor is afatinib. In some embodiments, the kinase inhibitor is osimertinib. In some embodiments, the kinase inhibitor is poziotinib. In some embodiments, the kinase inhibitor is criotinib. In some embodiments, the kinase inhibitor is cabozantinib. In some embodiments, the kinase inhibitor is capmatinib. In some embodiments, the kinase inhibitor is axitinib. In some embodiments, the kinase inhibitor is lenvatinib. In some embodiments, the kinase inhibitor is nintedanib. In some embodiments, the kinase inhibitor is regorafenib. In some embodiments, the kinase inhibitor is pazopanib. In some embodiments, the kinase inhibitor is sorafenib. In some embodiments, the kinase inhibitor is sunitinib.

Anti-cancer therapies that may be administered in combination with the bispecific anti-EGFR/c-Met antibody and lazertinib in the methods of the disclosure include any one or more of the chemotherapeutic drugs or other anti-cancer therapeutics known to those of skill in the art. Chemotherapeutic agents are chemical compounds useful in the treatment of cancer and include growth inhibitory agents or other cytotoxic agents and include alkylating agents, anti-metabolites, anti-microtubule inhibitors, topoisomerase inhibitors, receptor tyrosine kinase inhibitors, angiogenesis inhibitors and the like. Examples of chemotherapeutic agents include alkylating agents such as thiotepa and cyclophosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-FU; folic acid analogues such as denopterin, methotrexate, pteropterin, trimetrexate; purine analogues such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; members of taxoid or taxane family, such as paclitaxel (TAXOL®) docetaxel (TAXOTERE®) and analogues thereof; chlorambucil; gemcitabine; 6-thioguanine; mercaptopurine; methotrexate; platinum analogues such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; inhibitors of receptor tyrosine kinases and/or angiogenesis, including sorafenib (NEXAVAR®), sunitinib (SUTENT®), pazopanib (VOTRIENT™) toceranib (PALLADIA™), vandetanib (ZACTIMA™), cediranib (RECENTIN®), regorafenib (BAY 73-4506), axitinib (AG013736), lestaurtinib (CEP-701), erlotinib (TARCEVA®), gefitinib (IRESSA®), afatinib (BIBW 2992), lapatinib (TYKERB®), neratinib (HKI-272), and the like, and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (FARESTON®); and anti-androgens such as flutamide, nilutamide, bicalutamide, leuprolide, and goserelin; and pharmaceutically acceptable salts, acids or derivatives of any of the above. Other conventional cytotoxic chemical compounds as those disclosed in Wiemann et al., 1985, in *Medical Oncology* (Calabresi et aL, eds.), Chapter 10, McMillan Publishing, are also applicable to the methods of the present invention.

In some embodiments, the bispecific anti-EGFR/c-Met antibody is administered prior to administration of the compound of formula (I) or solvate, hydrate, tautomer or a pharmaceutically acceptable salt thereof.

In some embodiments, the bispecific anti-EGFR/c-Met antibody is administered prior to administration of the compound of formula (II) or solvate, hydrate, or tautomer thereof.

In some embodiments, the bispecific anti-EGFR/c-Met antibody is administered after administration of the compound of formula (I) or solvate, hydrate, tautomer or a pharmaceutically acceptable salt thereof.

In some embodiments, the bispecific anti-EGFR/c-Met antibody is administered after administration of the compound of formula (II) or solvate, hydrate, or tautomer thereof.

In some embodiments, the bispecific anti-EGFR/c-Met antibody is administered one or more times after administering the compound of formula (I) or solvate, hydrate, tautomer or a pharmaceutically acceptable salt thereof.

In some embodiments, the bispecific anti-EGFR/c-Met antibody is administered one or more times after administering the compound of formula (II) or solvate, hydrate, or tautomer thereof.

In some embodiments, the bispecific anti-EGFR/c-Met antibody is administered two, three, four, five, six, seven, eight, nine, ten or more times after administering the compound of formula (I) or solvate, hydrate, tautomer or a pharmaceutically acceptable salt thereof.

In some embodiments, the bispecific anti-EGFR/c-Met antibody is administered two, three, four, five, six, seven, eight, nine, ten or more times after administering the compound of formula (II) or solvate, hydrate, or tautomer thereof.

In some embodiments, the bispecific anti-EGFR/c-Met antibody is administered intermittently after administering the compound of formula (I) or solvate, hydrate, tautomer or a pharmaceutically acceptable salt thereof.

In some embodiments, the bispecific anti-EGFR/c-Met antibody is administered intermittently after administering the compound of formula (II) or solvate, hydrate, or tautomer thereof.

The length of time between administrations of the bispecific anti-EGFR/c-Met antibody and the compound of formula (I) or solvate, hydrate, tautomer or a pharmaceutically acceptable salt thereof, or formula (II) or solvate, hydrate, or tautomer thereof, or the third anti-cancer therapy may be a few minutes, such as about 1, 2, 5, 10, 30 or 60 minutes or several hours, such as about 2, 4, 6, 10, 12, 24 or 36 hours, or such as about 2, 4, 7, 14, 21, 28, 35, 42, 49, 56 days or more.

The bispecific anti-EGFR/c-Met antibody and the compound of formula (I) or solvate, hydrate, tautomer or a pharmaceutically acceptable salt thereof or the third anti-cancer agent may be administered as pharmaceutical compositions.

The bispecific anti-EGFR/c-Met antibody and the compound of formula (II) or solvate, hydrate, or tautomer thereof or the third anti-cancer agent may be administered as pharmaceutical compositions.

The bispecific anti-EGFR/c-Met antibody may be formulated into a pharmaceutical composition comprising the bispecific anti-EGFR/c-Met antibody and a pharmaceutically acceptable carrier. The pharmaceutically acceptable carrier may be one or more diluents, adjuvants, excipients, vehicles and the like. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used to formulate the bispecific anti-EGFR/c-Met antibody. These solutions are sterile and generally free of particulate matter. They may be sterilized by conventional, well-known sterilization techniques (e.g., filtration).

In some embodiments, the bispecific anti-EGFR/c-Met antibody is administered by an intravenous injection. In some embodiments, the bispecific anti-EGFR/c-Met antibody is administered by a subcutaneous injection.

In some embodiments, the compound of formula (I), or solvate, hydrate, tautomer or a pharmaceutically acceptable salt thereof, or the compound of formula (II) or solvate, hydrate, or tautomer thereof, is administered as an oral preparation, such as for example a solid oral preparation, such as a powder, capsule and tablet.

For solid oral preparations, such as powders, capsules and tablets, such as for example for the compound of formula (I) or compound of formula (II), suitable carriers and additives include starches, sugars, diluents, granulating agents, lubricants, binders, disintegrating agents and the like. Solid oral preparations may also be coated with substances such as sugars or be enteric-coated to modulate major site of absorption. For parenteral administration, the carrier may comprise sterile water and other excipients may be added to increase solubility or preservation. Injectable suspensions or solutions may also be prepared utilizing aqueous carriers along with appropriate additives. Suitable vehicles and formulations, inclusive of other human proteins, e.g., human serum albumin, are described, for example, in e.g. Remington: The Science and Practice of Pharmacy, $21^{st}$ Edition, Troy, D. B. ed., Lipincott Williams and Wilkins, Philadelphia, PA 2006, Part 5, Pharmaceutical Manufacturing pp 691-1092, See especially pp. 958-989.

The compositions may contain pharmaceutically acceptable auxiliary substances as required to approximate physiological conditions such as pH adjusting and buffering agents, stabilizing, thickening, lubricating and coloring agents, etc. The concentration of the bispecific anti-EGFR/c-Met antibody in the pharmaceutical formulation may vary, from less than about 0.5%, usually to at least about 1% to as much as 15%, 20%, 30%, 40% or 50% by weight and may be selected primarily based on required dose, fluid volumes, viscosities, etc., according to the particular mode of administration selected. Pharmaceutical compositions comprising solid forms may contain about 0.1 mg to about 2000 mg, such as about 1 mg, about 5 mg, about 10 mg, about 25 mg, about 50 mg, about 100 mg, about 150 mg, about 200 mg, about 300 mg, about 500 mg about 600 mg or about 1000 mg of active ingredient.

The mode of administration may be any suitable route that delivers the antibody to the host, such as parenteral administration, e.g., intradermal, intramuscular, intraperitoneal, intravenous or subcutaneous, pulmonary, transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intratumoral, intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

Additional Embodiments: Lazertinib Monotherapy

Lazertinib has been shown in clinical trials to be safe and well-tolerated, and exhibited promising systemic and intracranial anti-tumor activity in EGFR T790M+ NSCLC patients (see, e.g., Example 5). Anti-tumor activity of lazertinib (YH25448) is also described in the article by Yun, Jiyeon et al., "YH25448, an irreversible EGFR-TKI with Potent Intracranial Activity in EGFR mutant non-small-cell lung cancer," Clinical Cancer Research, Vol. 25, Issue 8, April 2019 (available online Jan. 22, 2019), which is incorporated by reference herein. As described therein, a 37-year-old Korean male with EGFR Del19/T790M mutant lung adenocarcinoma who had experienced systemic progression including brain following 8-month treatment of AZD3759 and 2-month treatment of gefitinib was treated with lazertinib 40 mg daily treatment; and tumor assessment after 6 weeks confirmed a 49.3% intracranial tumor reduction, with a 12.7% extracranial tumor reduction (overall 25.9% tumor reduction) without significant adverse events.

An embodiment of the present invention provides a method of reducing the size of a brain lesion or tumor in a human subject diagnosed with cancer comprising administering to the subject a therapeutically effective amount of a compound of formula (I) or a solvate, hydrate, tautomer, or a pharmaceutically acceptable salt thereof. Another embodiment of the present invention provides a method of reducing the size of a brain lesion or tumor in a human subject diagnosed with NSCLC (e.g., brain metastatic NSCLC) comprising administering to the subject a therapeutically effective amount of a compound of formula (I) or a solvate, hydrate, tautomer, or a pharmaceutically acceptable salt thereof (e.g., the mesylate salt of lazertinib). The compound of formula (I) or a solvate, hydrate, tautomer, or a pharmaceutically acceptable salt thereof may be administered at any of the doses described herein, e.g., an amount between about 20 mg and about 320 mg. According to particular embodiments, the dose is administered daily; for example, over a period of at least one week, at least 2 weeks, at least 3 weeks, at least 4 weeks, at least 5 weeks, at least 6 weeks, at least 7 weeks, or at least 8 weeks.

According to particular embodiments, the patient has been diagnosed with NSCLC with single activating EGFR mutation (L858R or Exon19Del or G719X or L861Q); the patient may have had progressive disease on prior EGFR-TKI therapy. According to an embodiment, the patient has been diagnosed with EGFR Del19/T790M mutant lung adenocarcinoma. The methods of treatment described herein may be effective in reducing the size of a patient's brain lesion(s), e.g., by at least about 1%, at least about 5%, at least about 10%, at least about 15%, at least about 25%, at least about 30%, or at least about 40%.

Embodiments of the invention are provided below:

Embodiment (1): A method of reducing the size of a brain lesion in a human subject diagnosed with EGFR Mutation Positive NSCLC, the method comprising administering to the subject a therapeutically effective amount of a compound of formula (I) or a solvate, hydrate, tautomer, or a pharmaceutically acceptable salt thereof.

Embodiment (2): The method of Embodiment (1), wherein the compound of formula (I) or solvate, hydrate, tautomer, or a pharmaceutically acceptable salt thereof is lazertinib (e.g., administered in the from of lazertinib mesylate).

Embodiment (3): The method of Embodiment (1) or (2), wherein the cancer is brain metastatic NSCLC.

Embodiment (4): The method of any of Embodiments (1)-(3) comprising administering the compound of formula (I) or solvate, hydrate, tautomer, or a pharmaceutically acceptable salt thereof in an amount between about 20 mg and about 320 mg.

Embodiment (5): The method of any of Embodiments (1)-(3) comprising administering the compound of formula (I) or solvate, hydrate, tautomer, or a pharmaceutically acceptable salt thereof in an amount between about 40 mg and about 240 mg.

Embodiment (6): The method of any of Embodiments (1)-(3) comprising administering the compound of formula (I) or solvate, hydrate, tautomer, or a pharmaceutically acceptable salt thereof in an amount between about 240 mg.

Embodiment (7): The method of any of Embodiments (1)-(6), comprising administering the compound of formula (I) or solvate, hydrate, tautomer, or a pharmaceutically acceptable salt thereof to the patient once daily.

Embodiment (8): The method of any of Embodiments (1)-(7), comprising administering the compound of formula (I) or solvate, hydrate, tautomer, or a pharmaceutically acceptable salt thereof to the patient once daily over a period of at least one week, at least 2 weeks, at least 3 weeks, at least 4 weeks, at least 5 weeks, at least 6 weeks, at least 7 weeks, or at least 8 weeks.

Embodiment (9): The method of any of Embodiments (1)-(8), wherein the method is effective in reducing the size of one or more brain lesions in the subject by at least about 1%, at least about 5%, at least about 10%, at least about 15%, at least about 25%, at least about 30%, or at least about 40%.

Embodiment (10): The method of any of Embodiments (1)-(9) comprising administering the compound of formula (I) or solvate, hydrate, tautomer, or a pharmaceutically acceptable salt thereof as part of a combination therapy with an additional therapeutic agent.

The present invention will now be described with reference to the following specific, non-limiting examples.

Example 1. JNJ-372 in Combination with Lazertinib Exhibited Tumor Cell Killing in H1975 Human Lung Carcinoma Xenograft Model The goal of the study was to assess the antitumor activity of JNJ-372 in combination with the third-generation TKIs lazertinib and osimertinib in H1975 human lung xenografts, which have activating EGFR (L858R) and second-site resistance EGFR (T790M) mutations, as well as in H1975-HGF xenografts, where the c-Met pathway is activated by autocrine over-expression of human HGF (c-Met ligand).

Methods

Female athymic nude mice (Crl:NU(Ncr)-Foxn1nu, Charles River) were nine weeks old and had a body weight (BW) range of 19.0-27.2 grams (g) at the start of treatment. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated Enrich-o'Cobs™ Laboratory Animal Bedding in static microisolators on a 12-hour light cycle at 20-22° C. (68-72° F.) and at 40-60% humidity. All studies complied with the recommendations of the *Guide for Care and Use of Laboratory Animals* with respect to restraint, husbandry, surgical procedures, feed and fluid regulation, and veterinary care.

Tumor Cell Culture

NCI-H1975 cells were grown to mid-log phase in RPMI 1640 medium containing 10% fetal bovine serum, 2 mM glutamine, 100 units/mL sodium penicillin G, 25 μg/mL gentamicin, and 100 μg/mL streptomycin sulfate. The tumor cells were cultured in tissue culture flasks in a humidified incubator at 37° C., in an atmosphere of 5% CO2 and 95% air.

In Vivo Implantation and Tumor Growth

On the day of implant, the NCI-H1975 cells were harvested during log phase growth and resuspended in phosphate buffered saline (PBS) at a concentration of $5 \times 10^7$ cells/mL. Xenografts were initiated by subcutaneously implanting $5 \times 10^6$ NCI-H1975 cells per animal (0.1 mL suspension) into the right flank of each test animal and tumors were monitored as their volumes approached the target range of 150-200 mm$^3$. Fifteen days later, animals were sorted into bins by calculated tumor volumes based on vernier caliper measurements of tumor width and length to the nearest mm. The animals were then heuristically sorted among treatment groups, balancing the distribution of small to large sized tumor volumes among group assignments. Residual animals were subjectively placed to minimize the standard error in tumor volume between groups until the number of animals assigned to each cohort satisfied the protocol design. Individual tumor volumes ranged from 108 to 288 mm$^3$ resulting in a group mean tumor volumes of 206 to 209 mm$^3$ for all groups. Tumor size, in mm$^3$, was calculated using the following formula:

$$\text{Tumor Volume} = (w^2 \times l)/2$$

where w=width and l=length, in mm, of the tumor. Tumor weight was estimated with the assumption that 1 mg is equivalent to 1 mm$^3$ of tumor volume.

Test Articles

JNJ-372 (also referred to as CNT04424 or HH80) and isotype control were dosed at 1 mg/mL PBS, resulting in a 10 mg/kg dosage. Osimertinib powder was suspended at 1 mg/mL in 20% (w/v) hydroxypropyl beta cyclodextrin (20% HPBCD) in deionized water, and stirred magnetically for 15 min to create an evenly dispersed suspension. Lazertinib (also referred to as JNJ-70080595, JNJ-595 or YH-CNT) powder was suspended at 1.17 mg/mL in 0.5% (w/v) methylcellulose (0.5% MC, vehicle) in deionized water which provided an active dosage of 10 mg/kg. All dosing solutions were formulated to provide the stated mg/kg dosage in a dosing volume of 10 mL/kg.

Treatment

Female athymic nude mice were used in the studies (n=10/group). Treatment began when SC tumors reached approximately 100 to 300 mm$^3$ in size. and dosing was initiated according to the treatment plan summarized in Table 2. JNJ-372, isotype control antibody, osimertinib, and lazertinib (also called JNJ-595) were dosed at 10 mg/kg (effective concentration). JNJ-372 was dosed twice a week IP for 3 weeks, and osimertinib and lazertinib were dosed orally daily for 21 days. The control group was dosed with vehicle orally daily for 21 days, and the isotype control antibody was dosed twice a week IP for 3 weeks. Mice were monitored for body weight and tumor volume up to Day 95, and were euthanized when individual tumor volume reached 2,000 mm$^3$ or at study conclusion.

TABLE 2

| Group | n | Agent | mg/kg | Route | Schedule | Agent | mg/kg | Route | Schedule |
|---|---|---|---|---|---|---|---|---|---|
| | | Treatment Regimen 1 | | | | Treatment Regimen 2 | | | |
| 1 | 10 | Vehicle* | — | po | Qd × 21 | Isotype | 10 | ip | Biwk × 3 |
| 2 | 10 | JNJ-595 | 10 | po | Qd × 21 | — | — | — | |
| 3 | 10 | Osimertinib | 10 | po | Qd × 21 | — | — | — | |
| 4 | 10 | JNJ-372 | 10 | ip | Biwk × 3 | — | — | — | |
| 5 | 10 | JNJ-595 | 10 | po | Qd × 21 | JNJ-372 | 10 | ip | Biwk × 3 |
| 6 | 10 | Osimertinib | 10 | po | Qd × 21 | JNJ-372 | 10 | ip | Biwk × 3 |

*vehicle = 0.5% MC in water

Calculations and Data Analysis

Relative body weight of individual mice was calculated using the formula: (W/W0)×100, where 'W' represents body weight on a particular day, and 'W0' represents body weight at initiation of treatment. Body weight was graphically represented as mean % of initial body weight±SEM.

Tumor volume data were graphically represented as the mean tumor volume±SEM. Tumor volume was calculated using the formula: tumor volume (mm$^3$)=(D×d2)/2; where 'D' represents the larger diameter, and 'd' the smaller diameter of the tumor as determined by caliper measurements.

The % TGI was defined as the difference between mean tumor burden of the treated and control group, calculated as % $\Delta TGI=([(TVc-TVc0)-(TVt-TVt0)]/(TVc-TVc0))\times 100$ where 'TVc' is the mean tumor burden of a given control group, 'TVc0' is the mean initial tumor burden of a given control group, 'TVt' is the mean tumor burden of the treated group, and 'TVt0' is the mean initial tumor burden of the treated group. Animals were removed from studies when a maximum tumor volume of ≥2,000 mm$^3$ was reached or when adverse clinical signs were noted. A CR was defined as a complete response (complete tumor regression) where the tumor was not measurable on the last day of analysis.

Tumor volume and body weight data were graphically represented using Prism software (GraphPad, version 7). Statistical significance was evaluated for all pairwise comparisons on the last day of the study when at least eight mice remained in each group. Differences between groups were considered significant when p<0.05. Statistical significance of tumor volume and body weight was calculated using the Linear Mixed-Effects analysis in R software version 3.4.2 (using Janssen's internally developed Shiny application version 3.3), with treatment and time as fixed effects and animal as random effect. Logarithmic transformation (base 10) was performed if individual longitudinal response trajectories were not linear. The information derived from this model was used to make pairwise treatment comparisons to the control group or between all the treatment groups.

Survival data was graphed and analyzed using GraphPad Prism 7.04 for Windows with day 1 as the treatment start date. Logrank (Mantel-Cox) analysis included the data for all animals in a group except those assessed as non treatment related (NTR) deaths. Two-tailed statistical analyses were conducted at significance level P=0.05. The statistical tests were not adjusted for multiple comparisons. Differences between groups were considered significant when p<0.05.

Results

Body Weight

Tolerability of JNJ-372 monotherapy or in combination with either TKI could not be assessed in these studies, since JNJ-372 does not bind to mouse EGFR or c-Met. Consistent with this, JNJ-372 monotherapy treatment did not elicit significant body weight loss compared to the control group at Day 29 in H1975-xenograft-bearing nude mice (FIG. 1). Treatment with osimertinib or lazertinib, either as monotherapies or in combination with JNJ-372, elicited some transient body weight loss in the H1975 model and lack of body weight gain compared to controls (p<0.05). Body weight loss was not significantly different with the combination of osimertinib or lazertinib plus JNJ-372, when compared to osimertinib or lazertinib monotherapies. One animal each in the groups treated with lazertinib, JNJ-372, and JNJ-372 plus lazertinib combination was euthanized on Days 21, 43, and 71, respectively, due to negative clinical signs; however, it was unclear whether this was due to tumor burden or treatment.

Efficacy

In Study H1975, monotherapy treatment with JNJ-372, lazertinib, or osimertinib elicited significant TGI of H1975 xenografts at Day 28 (86%, 112%, and 111%, respectively) as compared to controls (p≤0.0003). Combination of JNJ-372 plus either lazertinib or osimertinib resulted in 112% TGI as compared to controls at Day 28 (p<0.0001). Additionally, the combination of JNJ-372 plus osimertinib demonstrated statistically significant TGI as compared to either monotherapy (p≤0.03) and resulted in a CR in one animal. The combination of JNJ-372 plus lazertinib demonstrated significant TGI as compared to single agent JNJ-372 treatment (p<0.0001), with a nonsignificant trend of longer delay in tumor regrowth compared to lazertinib monotherapy. The combination of JNJ-372 plus lazertinib resulted in CRs in 7 of 10 mice, as compared to 1 of 10 CRs among mice treated with lazertinib alone. Combination of JNJ-372 plus either lazertinib or osimertinib resulted in statistically significant survival advantage as compared to controls (p≤0.0003). The combination of JNJ-372 plus lazertinib demonstrated statistically significant survival advantage compared to single agent JNJ-372 and single agent lazertinib treatment (p≤0.0344). The combination of JNJ-372 plus osimertinib demonstrated statistically significant survival advantage compared to single agent JNJ-372 treatment (p<0.0001) and a non-significant trend in survival advantage compared to single agent osimertinib treatment.

Figure 2:
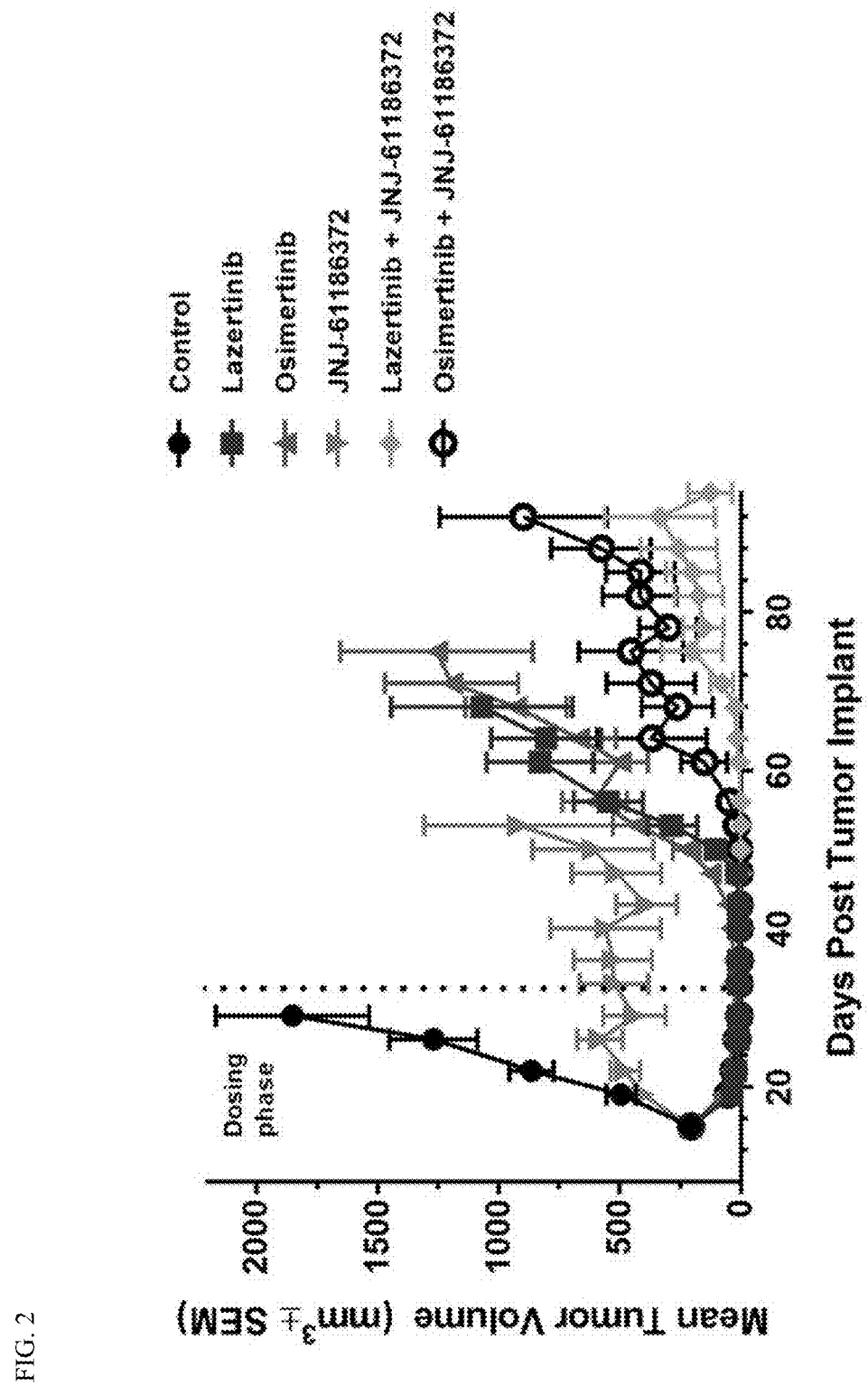
FIG. 2 shows the mean tumor volume ($mm^3$) in nude mice bearing H1975 xenografts treated with JNJ-61186372 monotherapy or combination with lazertinib or osimertinib.
Figure 3:
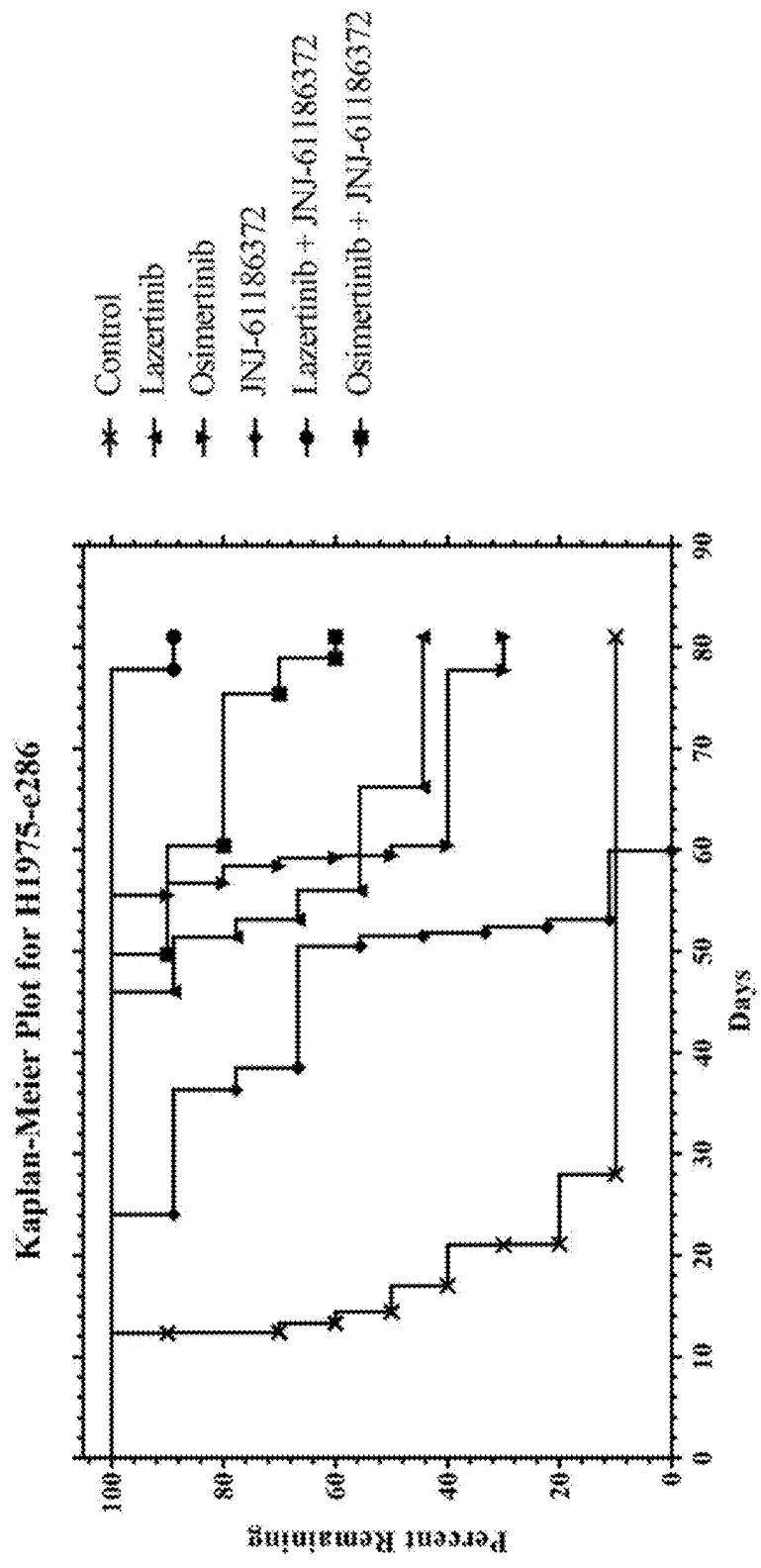
FIG. 3 shows the Kaplan-Meier plot for percent remaining animals in mice bearing H1975 xenografts treated with JNJ-61186372 monotherapy or combination with lazertinib or osimertinib.

Table 3 shows the tumor growth inhibition p values in the H1975 xenograft model. FIG. 2 shows the mean tumor volume (mm$^3$) days post tumor implant in nude mice bearing H1975 xenografts treated with JNJ-372 monotherapy or combination with lazertinib or osimertinib. FIG. 3 shows the Kaplan-Meier plot for percent remaining animals in mice bearing H1975 xenografts treated with treated with JNJ-372 monotherapy or combination with lazertinib or osimertinib. Table 4 shows the survival statistics p values in the H1975 xenograft model.

TABLE 3

| Treatment | Control | Lazertinib | Osimertinib | JNJ-372 |
|---|---|---|---|---|
| Lazertinib | <0.0001 | — | — | — |
| Osimertinib | <0.0001 | — | — | — |
| JNJ-372 | 0.0003 | — | — | — |
| Lazertinib + JNJ-372 | <0.0001 | 0.1606 | — | <0.0001 |
| Osimertinib + JNJ-372 | <0.0001 | — | 0.0307 | <0.0001 |

TABLE 4

| Treatment | Control | Lazertinib | Osimertinib | JNJ-372 |
|---|---|---|---|---|
| Lazertinib | 0.0022 | — | — | — |
| Osimertinib | 0.0037 | — | — | — |
| JNJ-372 | 0.0582 | — | — | — |
| Lazertinib + JNJ-372 | 0.0002 | 0.0344 | — | <0.0001 |
| Osimertinib + JNJ-372 | 0.0005 | — | 0.1259 | <0.0001 |

Example 2. JNJ-372 in Combination with Lazertinib or Osimertinib in H1975-HGF Exhibited Tumor Cell Killing in Human Lung Carcinoma Xenograft Model The experimental design was as described in Example 1 except that H1975 cells stably transfected to express hepatocyte growth factor (HGF) (H1975-HGF cells) were used in the studies and hereafter referred to as H1975-HGF-CNT. The cells were cultured in RPMI 1640 medium containing 2 mM L-glutamine (Invitrogen, Cat #11875-127). The medium was supplemented with 10% heat inactivated fetal bovine serum and 2 μg/mL puromycin. Puromycin was used as a selection agent in the cell culture system. Cells were cultured in tissue culture flasks in a humidified incubator at 37° C., in an atmosphere of 5% $CO_2$ and 95% air.

Results

Body Weight

Figure 4:
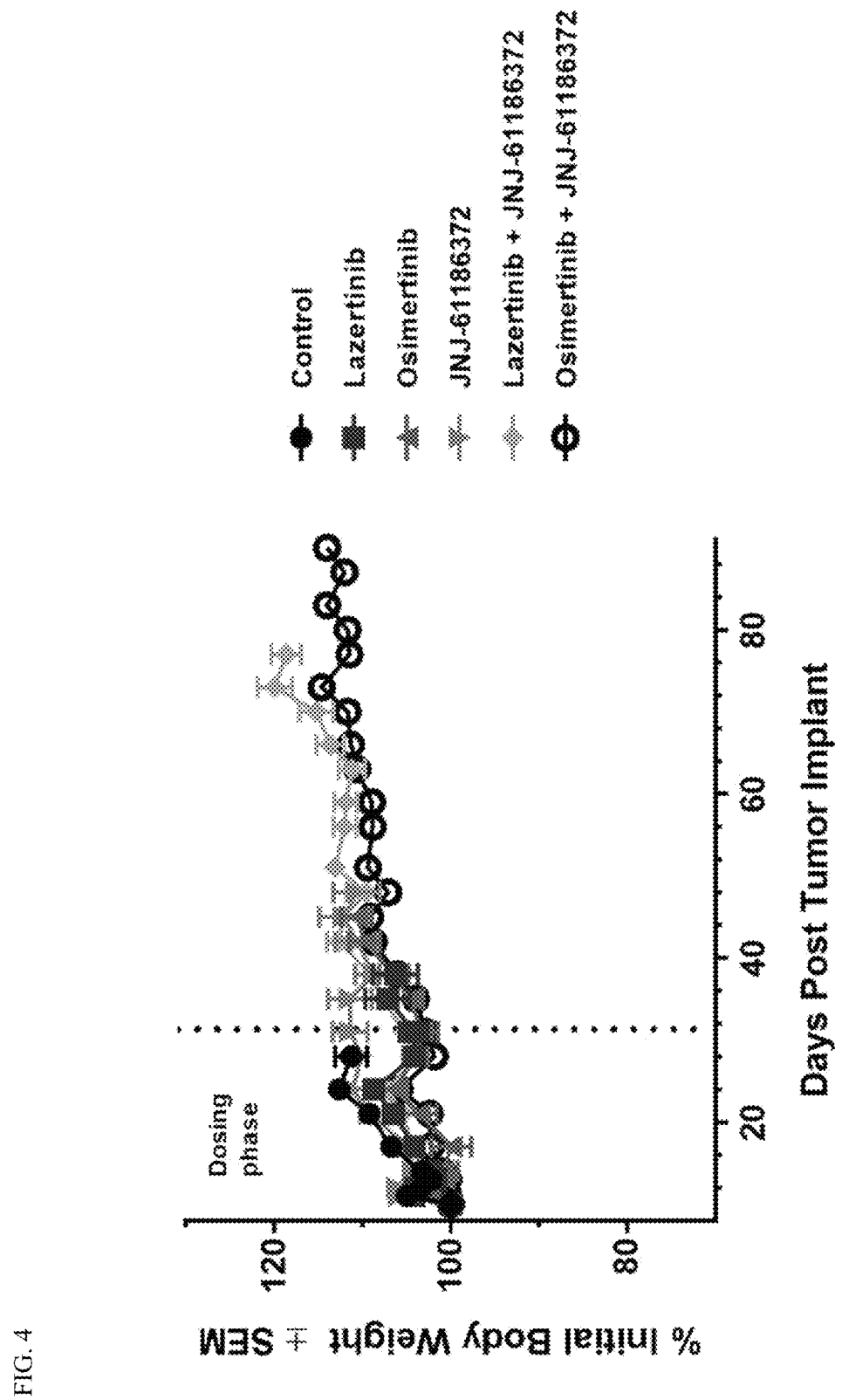
FIG. 4 shows the effect of JNJ-61186372 monotherapy or combination with lazertinib or osimertinib on body weight of nude mice bearing H1975-HGF xenografts.

In Study H1975-HGF, JNJ-372 monotherapy treatment did not elicit significant body weight loss compared to controls at Day 28 in H1975-HGF-tumor-bearing mice (FIG. 4). Treatment with osimertinib or lazertinib, either as monotherapies or in combination with JNJ-372, elicited some transient body weight loss and lack of body weight gain compared to the control group (p<0.05). Body weight loss was not significantly different with the combination of osimertinib or lazertinib plus JNJ-372, when compared to osimertinib or lazertinib monotherapies, respectively. One mouse each in the osimertinib and JNJ-372 monotherapy groups, and two mice in the group treated with JNJ-372 plus lazertinib combination were found dead or euthanized on Days 51, 53, 70, and 36, respectively, due to negative clinical signs; however, it was unclear whether this was due to tumor burden or treatment.

Treatment groups were as shown in Table 2.

Efficacy

In Study H1975-HGF, monotherapy with JNJ-372 or lazertinib elicited 70% and 75% TGI, respectively, of H1975-HGF xenografts, as compared to controls at Day 28 (p=0.0059 and p=0.0030, respectively). Treatment with osimertinib resulted in a statistically non-significant 57% TGI as compared to controls at Day 28 (p=0.0651). Combinations of JNJ-372 plus either lazertinib or osimertinib resulted in 109% or 108% TGI, respectively, as compared to controls at Day 28 of treatment (p<0.0001). Additionally, the combination of JNJ-372 plus either lazertinib or osimertinib resulted in significant TGI as compared to JNJ-372 or to the respective TKI monotherapy (p<0.0001). Finally, JNJ-372 plus lazertinib led to CRs in 3 of 10 mice while lazertinib monotherapy resulted in 2 of 10 CR. JNJ-372 plus osimertinib produced CRs in 4 of 10 mice. Combination of JNJ-372 plus either lazertinib or osimertinib resulted in statistically significant survival advantage as compared to controls (p<0.0001). The combination of JNJ-372 plus lazertinib demonstrated statistically significant survival advantage compared to single agent JNJ-372 and single agent lazertinib treatment (p≤0.0131). The combination of JNJ-372 plus osimertinib demonstrated statistically significant survival advantage compared to single agent JNJ-372 and single agent osimertinib treatment (p<0.0001).

Figure 5:
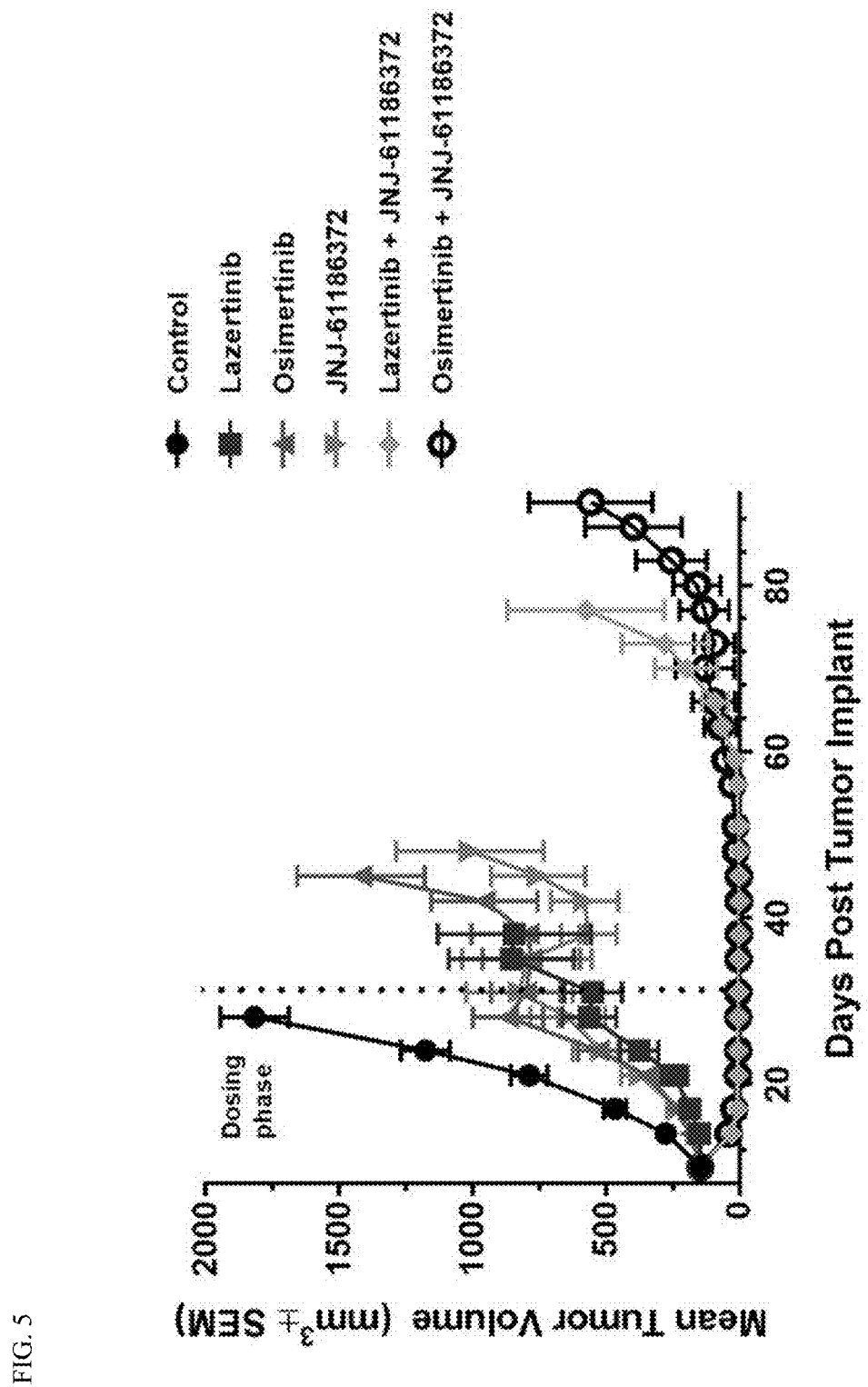
FIG. 5 shows the mean tumor volume ($mm^3$) days post tumor implant in nude mice bearing H1975-HGF xenografts treated with JNJ-61186372 monotherapy or combination with lazertinib or osimertinib.
Figure 6:
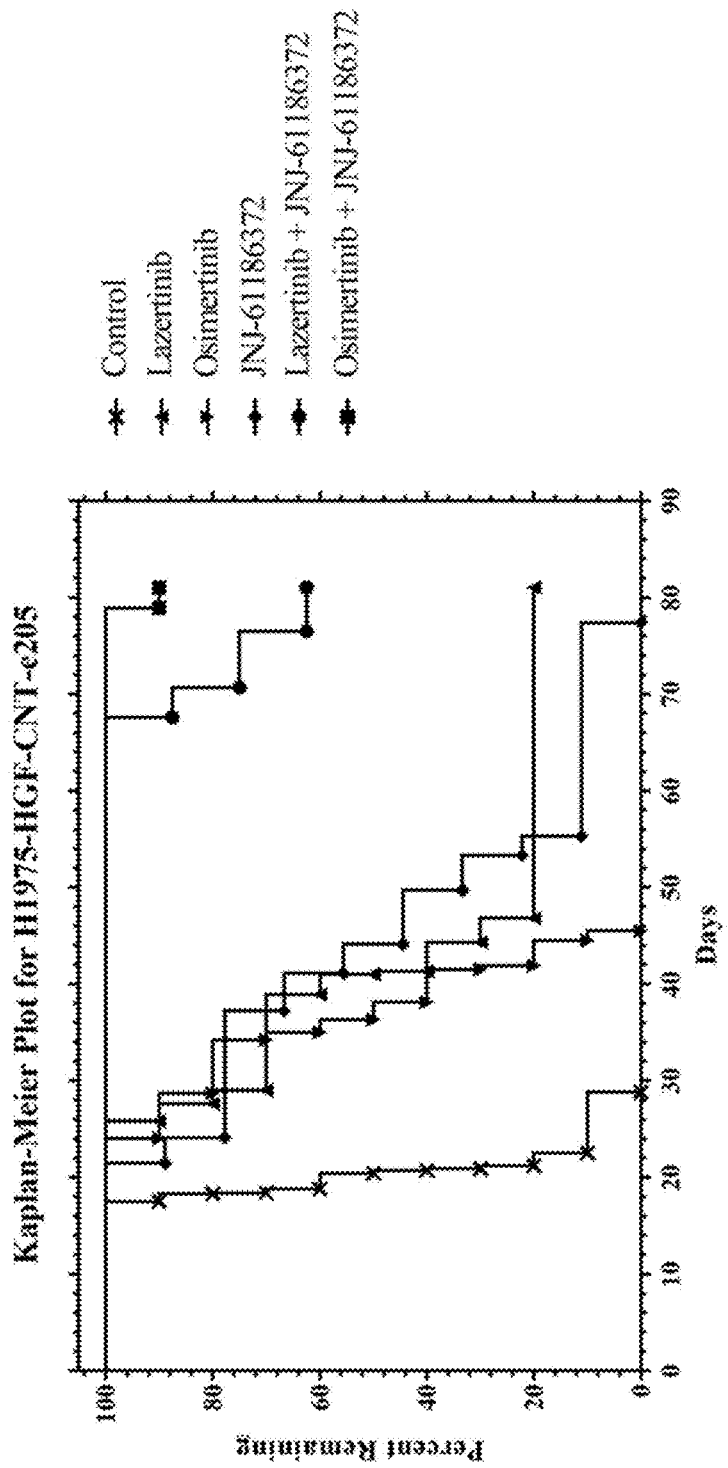
FIG. 6 shows the Kaplan-Meier plot for percent remaining animals in mice bearing H1975-HGF xenografts treated with JNJ-61186372 monotherapy or combination with lazertinib or osimertinib.

Table 5 shows the tumor growth inhibition p values in the H1975-HGF xenograft model. FIG. 5 show the mean tumor volume ($mm^3$) days post tumor implant in nude mice bearing H1975-HGF xenografts treated with JNJ-372 monotherapy or combination with lazertinib or osimertinib. FIG. 6 shows the Kaplan-Meier plot for percent remaining animals in mice bearing H1975-HGF xenografts treated with JNJ-372 monotherapy or combination with lazertinib or osimertinib. Table 6 shows the survival statistics p values in the H1975-HGF xenograft model.

TABLE 5

| Treatment | Control | Lazertinib | Osimertinib | JNJ-372 |
|---|---|---|---|---|
| Lazertinib | 0.0030 | — | — | — |
| Osimertinib | 0.0651 | — | — | — |
| JNJ-372 | 0.0059 | — | — | — |
| Lazertinib + JNJ-372 | <0.0001 | <0.0001 | — | <0.0001 |
| Osimertinib + JNJ-372 | <0.0001 | — | <0.0001 | <0.0001 |

TABLE 6

| Treatment | Control | Lazertinib | Osimertinib | JNJ-372 |
|---|---|---|---|---|
| Lazertinib | <0.0001 | — | — | — |
| Osimertinib | <0.0001 | — | — | — |
| JNJ-372 | <0.0001 | — | — | — |
| Lazertinib + JNJ-372 | <0.0001 | 0.0131 | — | 0.0004 |
| Osimertinib + JNJ-372 | <0.0001 | — | <0.0001 | <0.0001 |

Conclusions

The goal of these studies was to assess the antitumor activity of JNJ-372 in combination with the third-generation EGFR TKIs osimertinib and lazertinib in H1975 and H1975-HGF human NSCLC tumors.

JNJ-372 in combination with osimertinib or lazertinib demonstrated enhanced antitumor efficacy (by increasing TGI and/or CRs) as compared to JNJ-372 and respective TKI monotherapy treatment in both H1975 and H1975-HGF xenograft models. Some transient body weight loss was observed with osimertinib or lazertinib treatment. Tolerability of JNJ-372 plus TKI combinations could not be assessed since JNJ-372 does not bind to mouse EGFR or c-MET.

Overall, data from both the H1975 and H1975-HGF models suggested that combination treatment with TKIs plus JNJ-61186372 can provide superior anti-tumor activity as compared with TKI monotherapy and may be considered for further investigation in the clinical setting.

Example 3: Study 61186372EDI1001: A Phase 1, First-In-Human, Open-Label, Dose Escalation Study of JNJ-61186372, a Human Bispecific EGFR and c-Met Antibody, in Subjects with Advanced Non-Small Cell Lung Cancer This study is a first-in-human, open-label, multicenter, 2-part, Phase 1 dose escalation study to evaluate the safety and PK, establish a recommended Phase 2 dose (RP2D) and recommended Phase 2 combination dose (RP2CD) regimen, and to assess the preliminary efficacy of JNJ-61186372 as a monotherapy and in combination with lazertinib in subjects who are ≥18 years of age with advanced NSCLC. Objectives and endpoints of the study are shown in Table 7.

the MTD or MAD is reached, and whether dose cohort expansions are indicated. Additional subjects may be enrolled within a dose cohort already declared safe by the SET, in order to collect additional safety and PK data at the dose, up to 20 subjects per dose cohort. Additional subjects

TABLE 7

| OBJECTIVES | ENDPOINTS |
|---|---|
| Primary Part 1 Monotherapy and Combination Dose Escalations | |
| Determine the maximum tolerated dose (MTD), if one exists (Part 1 monotherapy dose escalation only), and the recommended Phase 2 dose (RP2D)/recommended Phase 2 combination dose (RP2CD) regimen for subjects with NSCLC treated with JNJ-61186372 or JNJ-61186372 and lazertinib, respectively | Dose Limiting Toxicity (DLT) |
| Part 2 Monotherapy and Combination Dose Expansions | |
| Determine the safety, tolerability, and anti-tumor activity of JNJ-61186372 monotherapy at the RP2D, and of JNJ-61186372 and lazertinib combination therapy at the RP2CD Estimate the anti-tumor activity of JNJ-61186372 at the RP2D, and of JNJ-61186372 and lazertinib combination therapy at the RP2CD, in selected populations of subjects with documented EGFR mutation(s) who have progressed after treatment with standard of care | Adverse events defined by the NCI CTCAE Criteria Version 4.03 in subjects treated at the RP2D regimen of JNJ-61186372 Overall response rate (ORR), duration of response (DOR), and clinical benefit rate (CBR) as determined by investigator, according to the Response Criteria in Solid Tumors (RECIST) v1.1 |
| Secondary JNJ-61186372 Monotherapy and JNJ-61186372 + Lazertinib Combination | |
| Assess additional measures of clinical benefit with JNJ-61186372 as monotherapy and in combination with lazertinib Assess the PK and immunogenicity of JNJ-61186372 monotherapy and JNJ-61186372 and lazertinib combination therapy following multiple dose administrations in subjects with NSCLC | Progression free survival, overall survival (OS), time to treatment failure (TTF) Serum PK parameters of JNJ-61186372 including but not limited to $C_{max}$, $T_{max}$, $AUC_{(t1-t2)}$, $AUC_{tau}$, $C_{trough}$, and R; detection of anti-JNJ-61186372 antibodies Plasma PK parameters of lazertinib including but not limited to $C_{max}$, $T_{max}$, and $C_{trough}$ |
| Exploratory | |
| Explore the relationship between serum PK and pharmacodynamic (PD) markers (e.g., soluble EGFR and c-Met) Explore biomarkers predictive of clinical response and resistance to JNJ-61186372 in blood and tumor tissue | |

Overview of Study Design

This study is a first-in-human, open-label, multicenter, 2-part, Phase 1 dose escalation study to evaluate the safety and PK, establish a recommended Phase 2 dose (RP2D) and recommended Phase 2 combination dose (RP2CD) regimen, and to assess the preliminary efficacy of JNJ-61186372 as a monotherapy and in combination with lazertinib in subjects who are ≥18 years of age with advanced NSCLC.

Part 1 JNJ-61186372 Monotherapy and Combination Dose Escalations: A traditional 3+3 design will be utilized to determine the MTD (or the maximum administered dose [MAD] if no MTD is defined) and the RP2D regimen(s) for JNJ-61186372 monotherapy, and the RP2CD of the JNJ-61186372 and lazertinib combination, in subjects with advanced NSCLC. The total number of subjects enrolled in each dose escalation will depend on the dose level at which may be enrolled into country-specific Part 1 dose cohorts in order to define safety and PK if required by their respective Health Authorities.

For the JNJ-61186372 and lazertinib Combination Dose Escalation, a strategy adapted from prior antibody and TKI combination studies in subjects with EGFR-mutated NSCLC will be utilized to determine the RP2CD of JNJ-61186372 and lazertinib, with the target dose of each agent in the RP2CD being the same as the RP2D of each agent as a monotherapy. The total number of subjects enrolled in the Combination Dose Escalation will depend upon the number of dose levels tested and dose cohorts at which the RP2CD is reached, and whether dose cohort expansions are required to determine the RP2CD. As in the monotherapy dose escalation, additional country-specific combination cohorts may be enrolled in order to define safety and PK if required by their respective Health Authorities.

Part 2 JNJ-61186372 Monotherapy and Combination Dose Expansions: Enrollment into Part 2 Cohorts A-D will commence after the RP2D regimen for JNJ-61186372 monotherapy is determined in Part 1. Up to approximately 120 subjects with advanced NSCLC who have a previously diagnosed activating EGFR mutation, measurable disease, and disease progression following prior systemic anti-cancer treatment for their disease will be initially enrolled at the RP2D regimen(s) determined during Part 1. The goal of Part 2 Cohorts A-D is to better characterize the safety and PK of JNJ-61186372 and to explore clinical activity within molecularly-defined tumor subgroups. In Cohorts C and D, the SET may recommend enrolling up to an additional 70 subjects each based upon safety and efficacy data. In addition, the SET may restrict enrollment to sub-populations if clinical benefit is demonstrated in molecularly-defined populations within a cohort.

Once the RP2CD for the combination of JNJ-61186372 and lazertinib has been identified in the Part 1 Combination Dose Escalation, the available safety, PK and preliminary efficacy data will be communicated with the relevant Health Authorities, prior to the commencement of the Part 2 combination Cohort E Expansion. Approximately 25 subjects with advanced EGFR-mutated NSCLC will be enrolled to further characterize the safety, tolerability, and preliminary efficacy of the combination. Subjects will be either treatment naïve for advanced disease, or have progressed after front-line treatment with erlotinib, gefitinib, afatinib, or after front- or second-line treatment with a third generation EGFR TKI.

Overall Study

For both Part 1 and Part 2, the study is divided into 3 periods. During the Screening Period, subject eligibility will be determined up to 28 days prior to the first dose of study drug. The Treatment Period will extend from the first dose of study drug until 30 days after the last dose of study drug. The Follow-Up Period will begin at the end of the Treatment Period and continue as subjects are followed for survival and subsequent anticancer therapies, until the end of the study. Subjects who permanently discontinue all study treatment for any reason other than radiological disease progression or withdrawal of consent will continue disease assessments per the protocol schedule until radiological progression is confirmed or new anticancer therapy begins, whichever comes first.

The study will be conducted in an outpatient setting. Subjects will be seen at the study center on the pre-specified days for study drug administration and study evaluations (e.g., adverse event monitoring, physical examinations, concomitant medication usage, laboratory assessments, and collection of PK samples). More frequent site visits may be scheduled, if needed, on the basis of emerging safety observations. Safety monitoring will be the same for both Part 1 and Part 2 of the study and includes evaluation of adverse events and laboratory abnormalities, which will be graded according to the NCI CTCAE (Version 4.03). Other safety measures include monitoring of vital signs, electrocardiograms (ECG), and physical examinations. Additional safety assessments such as chest X-rays and LVEF assessments (echocardiogram or MUGA) will be performed for those subjects receiving combination JNJ-61186372 and lazertinib, in Part 1 and Part 2 of the study. The overall safety of JNJ-61186372, as both a monotherapy and in combination with lazertinib, will be assessed by the Safety Evaluation Team (SET).

Anti-tumor activity will be evaluated by clinical responses as per the Response Evaluation Criteria in Solid Tumors (RECIST v1.1) (Eisenhauer et al., *Eur J Cancer* 2009; 45(2):228-247) The investigator will evaluate sites of disease by radiological imaging, physical examination, and other procedures, as necessary, and all results will be recorded in the case report form (CRF). In Part 2, intra-subject dose escalations may be permitted in subjects with non-progressing disease, in the event a new or modified RP2D or RP2CD has been selected by the SET.

Subject Population

In this study, subjects with advanced NSCLC will be enrolled, as these tumors may potentially respond to treatment with JNJ-61186372. In addition, all subjects will have progressed on prior therapy or will be ineligible for or refused all other currently available approved therapeutic options and will be in need of additional effective therapies.

In Part 1 (Dose Escalation) of the study, subjects with advanced NSCLC will be enrolled. For Part 1 Combination Dose Escalation only, subjects must have been diagnosed with EGFR Exon 19del or L858R activating mutation and be TKI treatment naïve for advanced disease, or have progressed after front-line treatment with first or second generation TKI, or have been treated with a third generation TKI in either the front-line or second-line setting, and are not eligible for enrollment in Cohort C. The total number of subjects enrolled will depend on the dose level at which the MTD or MAD is reached, and whether dose cohort expansions are indicated.

In Part 2 (Dose Expansion) of the study, up to approximately 145 subjects with previously treated advanced NSCLC with a previously diagnosed activating EGFR mutation and measurable disease, will be initially enrolled into one of 5 distinct cohorts, as defined by the following:

Cohort A: subjects with previously treated, EGFR-driven tumor progression

Cohort B: subjects with previously treated, EGFR-independent tumor progression.

Cohort C: subjects with documented EGFR or c-Met alterations that mediate resistance to previous treatment with third generation TKI (e.g., osimertinib), or in the case of primary Exon 20ins disease, previous treatment with TKI with known activity in Exon 20ins disease (e.g., poziotinib). The alteration must be demonstrated by previous characterization, using local lab testing of equivalent tumor tissue prior to screening, until appropriately validated NGS of ctDNA or tumor tissue for central testing is available. Once available, all subjects will be centrally assessed for eligibility based on EGFR and c-Met characterization of tumor sample obtained during the Screening Period, or with equivalent tumor tissue obtained prior to the Screening Period, but following treatment with most recent systemic anti-cancer therapy.

Cohort D: subjects with previously diagnosed activating EGFR exon 20 insertion mutation.

Cohort E (combination JNJ-61186372 and lazertinib): subjects with advanced EGFR-mutated NSCLC characterized by Exon19del or L858R sensitive activating mutations.

In Cohorts C and D, the SET may recommend enrolling up to an additional 70 subjects each based on results of interim monitoring. Subjects who do not have their EGFR mutation confirmed at the central laboratory may be replaced. Due to changing standard of care, and overlapping target populations, Cohort A and B will be closed to further recruitment upon opening of Cohort C and D. Approximately 25 subjects will be enrolled into combination Cohort E to further characterize the safety, tolerability, and preliminary efficacy of the combination JNJ-61186372 and lazertinib at the RP2CD.

JNJ-61186372 and Lazertinib Combination

The monotherapy RP2Ds (1050/1400 mg for JNJ-61186372 and 240 mg for lazertinib) and PK profiles for both JNJ-61186372 and lazertinib have been established through their respective FIH dose escalation studies, in which no DLTs were observed for either compound through doses higher than their respective RP2Ds (1400 mg for JNJ-61186372 and 320 mg for lazertinib). The safety profile and preliminary efficacy of both agents in EGFR-mutated NSCLC population is based upon clinical experience of approximately 100 subjects in each study, including those enrolled into expansion cohorts at their respective RP2D. In addition, both agents have demonstrated clinical activity in the targeted population starting at doses below their respective RP2Ds (700 mg for JNJ-61186372 and 240 mg for lazertinib), allowing for the potential to maintain efficacy if the safety profile of the combination requires dosing of either agent below their monotherapy RP2D.

Rationale for Dose and Regimen Selection

The doses to be explored in the combination study (Table 8) were selected based on the currently available clinical safety, tolerability, efficacy, and clinical PK observed in the FIH studies of both drugs as described above, taking into account the potential overlapping toxicity profile and the predicted lack of anticipated DDI. The starting dose of JNJ-61186372 was set to one dose level lower (700/1050 mg) than its monotherapy RP2D, while lazertinib was set at its RP2D (240 mg). Table 8 describes the dose levels that are anticipated to be explored in the combination study.

TABLE 8

| *Dose level | JNJ-61186372 (4XQW/Q2W) (Dose < 80 kg/Dose ≥ 80 kg) | Lazertinib (mg/day) |
|---|---|---|
| −1** | 700/1050 | 160 |
| 1 (starting dose) | 700/1050 | 240 |
| 2 | 1050/1400 | 240 |

*Additional and/or intermediate dose levels may be added during the course of the study. Cohorts may be added at any dose level below the MTD in order to better understand safety, PK or PD.
**Dose level −1 represent dose de-escalation cohorts or treatment doses for patients requiring a dose reduction from the starting dose level.

Although target doses for both JNJ-61186372 and lazertinib in combination are consistent with their RP2D as monotherapies (1050/1400 mg; and 240 mg, respectively), higher doses may be pursued if the evolving exposure data suggest that higher doses are required to achieve equivalent target PK exposures. If the evolving exposure data suggest that higher doses than level 2 (Table 8) are required to achieve exposures observed at the monotherapy RP2D of either agent, the combination safety, PK, and efficacy data will be communicated with the relevant Health Authorities, as well as the rationale for the next suggested dose cohort level, prior to initiation of the next combination cohort.

Dosing Schedule of the Combination

In the current monotherapy dosing regimen, lazertinib is administered as a daily oral therapy, while JNJ-61186372 is administered intravenously weekly during Cycle 1, and then every other week thereafter, beginning with Cycle 2 Day 1.

The first dose of JNJ-61186372 is administered as a split dose over 2 days (i.e., Cycle 1 Day 1 [350 mg] and Cycle 1 Day 2 [remainder of dose]) as a mitigation against the risk of infusion related reactions, one of the more common toxicities associated with JNJ-61186372, which occur primarily with the first (C1D1) dose. In addition, steroid premedication is currently required for only this first dose.

Dosing with lazertinib will begin before JNJ-61186372 initiation, no more than 2 hours prior to the initiation of the first dose of JNJ-61186372 on Cycle 1 Day 1, and continue in the same order daily thereafter.

The combination regimen will be administered in 28-day cycles, beginning with the first dose of JNJ-61186372 and lazertinib. The first 28-day cycle (Cycle 1) of the combination regimen should include 4 weekly doses of JNJ-61186372 and 28 doses of lazertinib, while Cycle 2 and all subsequent cycles will include 2 biweekly doses of JNJ-61186372 and 28 daily doses of lazertinib.

Subject Selection

Screening for eligible subjects will be performed within 28 days before the first administration of the study drug.

The inclusion and exclusion criteria for enrolling subjects in this study are described in the following 2 subsections. Subjects must meet all of these criteria to be eligible for study participation and no exceptions to these criteria will be granted by the sponsor. However, if there is a question about the inclusion or exclusion criteria below, the investigator should consult with the appropriate sponsor representative before enrolling a subject in the study.

Inclusion Criteria

Each potential subject must satisfy all of the following criteria to be enrolled in the study.

1. Subject must be ≥18 years of age and satisfy the legal age of consent in the jurisdiction in which the study is being conducted.
2. Subject must have histologically or cytologically confirmed NSCLC that is metastatic or unresectable. Subjects must have either progressed after receiving prior therapy for metastatic disease, be ineligible for, or have refused all other currently available therapeutic options. In cases where subjects refuse currently available therapeutic options, this must be documented in the study records.
3. For Part 1 Combination Dose Escalation only: Subjects must have been diagnosed with EGFR Exon 19del or L858R activating mutation and
    be TKI treatment naïve for advanced disease, or
    have progressed after front-line treatment with first (erlotinib or gefitinib) or second generation (afatinib) TKI, or
    have been treated with a third generation TKI (e.g., osimertinib) in either the front-line or second-line setting, and are not eligible for enrollment in Cohort C.
    For Part 2 only: Subjects must also have disease with a previously diagnosed activating EGFR mutation (includes both inhibitor sensitive primary mutations such as Exon 19 deletion and L858R [Cohort C and E], as well as marketed TKI-resistant mutations such as Exon 20 insertion [Cohort C and D]). Documentation of EGFR mutation eligibility by CLIA-certified laboratory (or equivalent) testing is required.
4. For Part 1: Subject must have evaluable disease.
    For Part 2: Subject must have measurable disease according to RECIST v1.1.
5. For Part 2:
    Cohort A and B: Subject's disease must have most recently progressed following treatment with a marketed EGFR inhibitor. Exception: In subjects diagnosed with mutations associated with de novo EGFR inhibitor resistance (e.g., exon 20 insertions), only previous treatment with combination platinum-based chemotherapy is required.

Cohort C: Subjects must have documented EGFR or c-Met alterations mediating resistance to previous treatment with a third generation TKI (e.g., osimertinib), or in the case of primary Exon 20ins disease, previous treatment with a TKI with known activity against Exon 20ins disease (e.g. poziotinib), which must be demonstrated by previous characterization, using local lab testing of equivalent tumor tissue prior to screening, until appropriately validated NGS of ctDNA or tumor tissue for central testing is available. Once available, all subjects will be centrally assessed for eligibility based on EGFR and c-Met characterization of tumor sample obtained during the Screening period, or with equivalent tumor tissue obtained prior to the Screening Period, but following treatment with most recent systemic anti-cancer therapy.

Cohort D: Subjects must have been previously diagnosed with an EGFR Exon 20 insertion.

Cohort E (combination JNJ-61186372 and lazertinib): Subjects must have been diagnosed with EGFR Exon 19del or L858R activating mutation, and
  be TKI treatment naïve for advanced disease, or
  have progressed after front-line treatment with first generation (erlotinib or gefitinib) or second generation (afatinib) TKI, or
  have progressed after treatment with a third generation TKI (e.g., osimertinib) in either the front-line or second-line setting and are not eligible for enrollment in Cohort C.

6. Subject must have ECOG performance status 0 or 1.
7. Subject must have organ and bone marrow function as follows:
  Hemoglobin≥10 g/dL
  ANC≥1.5×10$^9$/L
  Platelets≥75×10$^9$/L
  AST and ALT≤3×ULN (upper limit of normal)
  Total bilirubin≤1.5×ULN; subjects with Gilbert's syndrome can enroll if conjugated bilirubin is within normal limits
  Serum creatinine<1.5×ULN or if available, calculated or measured creatinine clearance>50 mL/min/1.73 m$^2$
  Subjects must meet laboratory criteria above without having history of red blood cell transfusion, platelet transfusion or G-CSF support within 7 days prior to the date of the test.
8. Before enrollment, a woman must be either:
  a. Not of childbearing potential: premenarchal; postmenopausal (>45 years of age with amenorrhea for at least 12 months); permanently sterilized (e.g., bilateral tubal occlusion [which includes tubal ligation procedures as consistent with local regulations], hysterectomy, bilateral salpingectomy, bilateral oophorectomy); or otherwise be incapable of pregnancy,
  b. Of childbearing potential and practicing effective method(s) of birth control consistent with local regulations regarding the use of birth control methods for subjects participating in clinical studies, as described below:
    1) Practicing true abstinence (when this is in line with the preferred and usual lifestyle of the subject), which is defined as refraining from heterosexual intercourse during the entire period of the study, including up to 6 months after the last dose of study drug is given. Periodic abstinence (calendar, symptothermal, post-ovulation methods) is not considered an acceptable contraceptive method.
    or
    2) Have a sole partner who is vasectomized
    or
    3) Practicing 2 methods of contraception, including one highly effective method (i.e., established use of oral, injected or implanted hormonal methods of contraception; placement of an intrauterine device [IUD] or intrauterine system [IUS], AND, a second method, (e.g., condom with spermicidal foam/gel/film/cream/suppository or occlusive cap [diaphragm or cervical/vault caps] with spermicidal foam/gel/film/cream/suppository)
  Subjects must agree to continue contraception throughout the study and continuing through 6 months after the last dose of study drug.
  Note: If the childbearing potential changes after start of the study (e.g., woman who is not heterosexually active becomes active, premenarchal woman experiences menarche) the woman must begin a highly effective method of birth control, as described above.
9. A woman of childbearing potential must have a negative serum (β-human chorionic gonadotropin [β-hCG]) at screening.
10. A woman must agree not to donate eggs (ova, oocytes) for the purposes of assisted reproduction during the study and for 6 months after receiving the last dose of study drug.
11. A man who is sexually active with a woman of childbearing potential must agree to use a condom with spermicidal foam/gel/film/cream/suppository and his partner must also be practicing a highly effective method of contraception (i.e., established use of oral, injected or implanted hormonal methods of contraception; placement of an intrauterine device [IUD] or intrauterine system [IUS]).
  If the subject is vasectomized, he must still use a condom (with or without spermicide), but his female partner is not required to use contraception.
  The subject must also not donate sperm during the study and for 6 months after receiving the last dose of study drug.
12. Subject must be willing and able to adhere to the prohibitions and restrictions specified in this protocol.
13. Each subject must sign an informed consent form (ICF) indicating that he or she understands the purpose of and procedures required for the study is willing to participate in the study, including the requirement to provide information during the Follow-up period.
14. Subjects eligible for Part 2 must agree to the pre-treatment tumor biopsy (or submission of equivalent archival material) and a tumor biopsy at the time of disease progression, as well as corresponding blood samples for ctDNA analysis. For subjects in Cohort C, equivalent pre-treatment tumor tissue must have been collected following treatment with the most recent prior systemic anti-cancer treatment.

Exclusion Criteria

Any potential subject who meets any of the following criteria will be excluded from participating in the study.
  1. Subject has uncontrolled inter-current illness, including but not limited to poorly controlled hypertension or diabetes, ongoing or active infection, or psychiatric illness/social situation that would limit compliance with study requirements.
2. Subject has had prior chemotherapy, targeted cancer therapy, immunotherapy, or treatment with an investigational anticancer agent within 2 weeks or 4 half-lives whichever is longer, before the first administration of JNJ-61186372. For agents with long half-lives, the maximum required time since last dose is 4 weeks. Toxicities from previous anticancer therapies should have resolved to baseline levels or to Grade 1 or less, (except for alopecia [any grade], Grade≤2 peripheral neuropathy, and Grade≤2 hypothyroidism stable on hormone replacement).
    For Part 1 Combination Dose Escalation: Any previous treatment with systemic anti-cancer immunotherapy, including but not limited to anti-PD-1, anti-PD-L1, and anti-CTLA-4 agents.
    For Part 2 only:
    Cohorts A and B: Prior treatment with chemotherapy for metastatic disease is not allowed unless the tumor mutation carries de-novo resistance to EGFR TKI (e.g., exon-20 insertions).
    Cohort C: Prior treatment with more than 2 lines of cytotoxic chemotherapy for metastatic disease (maintenance therapy is not included).
    Cohort D: Previous treatment with an EGFR TKI with activity against EGFR Exon 20 insertions (such as poziotinib).
    Cohort E (combination JNJ-61186372 and lazertinib): Any previous treatment with systemic anti-cancer immunotherapy including but not limited to anti-PD-1, anti-PD-L1, and anti-CTLA-4 agents.
    Note: Localized, radiotherapy for palliative purposes must be completed at least 7 days prior to treatment with JNJ-61186372.
3. Subjects with untreated brain metastases. Patients with treated metastases that are clinically stable and asymptomatic for at least 2 weeks and who are off or receiving low-dose corticosteroid treatment (510 mg prednisone or equivalent) for at least 2 weeks prior to study treatment are eligible. Exception: subjects with asymptomatic, untreated brain metastases, each less than 1 cm in diameter, may be eligible for JNJ-61186372 and lazertinib combination therapy in the Part 1 Combination Dose Escalation or Part 2 Combination Expansion Cohort E.
4. Subject has a history of malignancy other than the disease under study within 3 years before screening (exceptions are squamous and basal cell carcinomas of the skin and carcinoma in situ of the cervix, or malignancy that in the opinion of the investigator, with concurrence with the sponsor's medical monitor, is considered cured, or with minimal risk of recurrence within a year from screening).
5. Subject has a history of clinically significant cardiovascular disease including, but not limited to:
    Diagnosis of deep vein thrombosis or pulmonary embolism within 1 month prior to the first dose of study drug, or any of the following within 6 months prior to the first dose of study drug: myocardial infarction, unstable angina, stroke, transient ischemic attack, coronary/peripheral artery bypass graft, or any acute coronary syndrome. Clinically non-significant thrombosis, such as non-obstructive catheter-associated clots, are not exclusionary.
    Prolonged QTcF interval>480 msec or clinically significant cardiac arrhythmia or electrophysiologic disease (e.g., placement of implantable cardioverter defibrillator or atrial fibrillation with uncontrolled rate).
    Uncontrolled (persistent) hypertension: systolic blood pressure>180 mmHg; diastolic blood pressure>100 mmHg
    Congestive heart failure defined as New York Heart Association (NYHA) class III-IV or Hospitalization for CHF (any NYHA class) within 6 months of study Day 1
    Pericarditis/clinically significant pericardial effusion
    Myocarditis
    Baseline LVEF ejection fraction below the lower limit of normal (LLN), as assessed by screening echocardiogram or multigated acquisition (MUGA) scan.
6. Subject has leptomeningeal disease.
7. Subject has known allergies, hypersensitivity, or intolerance to JNJ-61186372 or its excipients
8. Subject has received an investigational drug (including investigational vaccines, but not including anticancer therapy [refer to Exclusion Criterion #2]) or used an invasive investigational medical device within 6 weeks before the planned first dose of study drug.
9. Subject is a woman who is pregnant, or breast-feeding, or planning to become pregnant while enrolled in this study or within 6 months after the last dose of study drug.
10. Subject is a man who plans to father a child while enrolled in this study or within 6 months after the last dose of study drug.
11. Subject has, or will have, any of the following:
    a. An invasive operative procedure with entry into a body cavity, within 4 weeks or without complete recovery before Cycle 1 Day 1. Thoracentesis, if needed, and percutaneous biopsy for baseline tumor tissue sample may be done less than 4 weeks prior to Cycle 1 Day 1, as long as the subject has adequately recovered from the procedure prior to the first dose of study drug in the clinical judgement of the investigator;
    b. Significant traumatic injury within 3 weeks before the start of Cycle 1 Day 1 (all wounds must be fully healed prior to Day 1);
    c. Any medical condition that requires intact wound healing capacity and is expected to endanger subject safety if wound healing capacity would be severely reduced during administration of the investigational agent;
    d. Expected major surgery while the investigational agent is being administered or within 6 months after the last dose of study drug.
12. Subject has any condition for which, in the opinion of the investigator, participation would not be in the best interest of the subject (e.g., compromise the well-being) or that could prevent, limit, or confound the protocol-specified assessments.
13. Any investigative site personnel directly affiliated with this study.
14. Subject has a history of hepatitis B surface antigen (HBsAg) or hepatitis C antibody (anti-HCV) positive, or other clinically active infectious liver disease, or tests positive for HBsAg or anti-HCV at Screening.
    Note: Subjects with a history of hepatitis C, who have completed antiviral treatment and have subsequently documented absence of serum HCV RNA at Screening are allowed to participate.
15. Subject has a history of human immunodeficiency virus (HIV) antibody positive, or tests positive for HIV at Screening.
16. Subject has any serious underlying medical or psychiatric condition (e.g., alcohol or drug abuse), dementia or altered mental status or any issue that would impair the ability of the subject to receive or tolerate the planned treatment at the investigational site, to understand informed consent or that in the opinion of the investigator would contraindicate the subject's participation in the study or confound the results of the study.
17. Medical history of interstitial lung disease (ILD), including drug-induced ILD or radiation pneumonitis requiring treatment with prolonged steroids or other immune suppressive agents within the last 2 years.

Toxicity Monitoring and Dose Modification

Monitoring of toxicities for subjects receiving combination JNJ-61186372 and lazertinib therapy will be identical to that of subjects receiving monotherapy JNJ-61186372, with the additional assessments of 1) a chest X-ray at baseline and at the end of Cycle 1 and 2) assessments of LVEF at baseline and again after 6 weeks.

In instances where dose reductions are felt to be indicated, they should occur as outlined in Table 9.

TABLE 9

| Combination Dosing Level | JNJ-61186372 dose (mg) (dose < 80 kg/dose ≥ 80 kg) | Lazertinib Dosing (mg) |
|---|---|---|
| 1 | 1050/1400 | 240 |
| 2 | 700/1050 | 240 |
| 3 | 700/1050 | 160 |
| 4 | 350/700 | 160 |
| 5 | Discontinue | 240 |
| 6 | Discontinue | 160 |
| 7 | Discontinue | Discontinue |

[a]Initiate dose reductions starting at step corresponding to RP2CD

Safety Evaluations

The safety of JNJ-61186372 as a monotherapy or in combination with lazertinib will be assessed by physical examinations, Eastern Cooperative Oncology Group (ECOG) criteria for performance status, laboratory tests, vital signs, electrocardiograms, monitoring of adverse events, and concomitant medication usage. Additional Chest X-rays and LVEF assessments will be conducted for those subjects undergoing treatment with JNJ-61186372 and lazertinib combination therapy. Adverse events that occur between the signing of the informed consent through 30 days following the last dose of study drug will be recorded. The severity of adverse events will be assessed using National Cancer Institute Common Terminology Criteria for Adverse Events (NCI CTCAE), Version 4.03. All subjects will be followed for survival until the end of study. Subjects who discontinue study treatment for any reason other than disease progression or withdrawal of consent for follow-up will continue to have disease assessments performed until either disease progression is documented by imaging or the subject begins a new cancer therapy. Data on anticancer therapies administered after this study will also be collected.

Pharmacokinetic Evaluations

Blood samples will be collected from all subjects for the measurement of serum JNJ-61186372 and plasma lazertinib concentration for PK analyses. The PK profile of JNJ-61186372 will be based on serum concentration data obtained from the timepoints surrounding the first and fifth dose administrations. Blood samples for sparse PK will also be obtained following all other dose administrations. Pharmacokinetic parameters will be estimated for individuals, and descriptive statistics will be calculated for each dose level.

Immunogenicity Evaluations

Blood samples will be collected and analyzed for antibodies to JNJ-61186372 using a validated immunoassay. Serum samples will be screened for antibodies binding to JNJ-61186372, and serum titer will be determined from positive samples. All samples collected for immune response analysis will be evaluated for JNJ-61186372 concentration in serum to ensure appropriate interpretation of immune response data. Other immunogenicity analyses may be performed to further characterize any immune responses generated. The incidence of antibodies against JNJ-61186372 will be summarized for all subjects who received at least one administration of study drug.

Pharmacodynamic and Biomarker Evaluations

Blood samples collected at screening and during the study will undergo analysis for circulating tumor DNA (ctDNA) to evaluate molecular alterations at baseline for cohort assignment, track response to treatment, and understand mechanisms of resistance to JNJ-61186372. In addition, blood samples for PD assessments will be collected. Tumor tissue collected at screening, post-treatment, and post-progression (within approximately 30 days of documentation of disease progression) may be evaluated for biomarkers relevant to cancer. The analysis of these tumor tissue samples will help to understand the molecular biology of the tumor, the efficacy observed with JNJ-61186372, and the mechanisms of acquired resistance to JNJ-61186372. These samples may also be utilized to confirm ctDNA testing results.

Efficacy Analyses

Primary efficacy analysis of ORR with confirmed best overall responses will be performed approximately 16 weeks after the last subject receives the first infusion or at the end of study, whichever comes first. The data cutoff will be communicated to the sites. All treated analysis set will be used for the primary efficacy analysis. Any additional data will be reported to the appropriate health authorities in a CSR addendum when all subjects are off the study drug.

For Cohort A and B, due to the limited number of subjects and the nature of the study, all efficacy analyses will be considered descriptive.

For Cohort C, and Cohort D, interim monitoring will be conducted.

Overall response rate (ORR) is defined as the proportion of subjects who achieve either a complete (CR) or partial response (PR) in all treated analysis set (or response evaluable analysis set for interim monitoring) in each expansion cohort (Part 2), as defined by RECIST v1.1. Observed ORR along with their two-sided 95% confidence intervals will be presented for each cohort and dose level as appropriate.

The following Bayesian approach will be used as a sensitivity analysis. The first criterion ensures that the ORR should be better than the clinically minimally effective threshold, 50%, and the second criteria is to make sure the type I error of 0.2 is controlled.
1. P (true ORR≥250%|observed ORR, n=100)≥0.5; the posterior probability of true ORR≥50% is at least 0.5
2. P (true ORR≥30%|observed ORR, n=100)≥0.8; the posterior probability of true ORR>30% is at least 0.8

Using Bayesian power, meeting the $2^{nd}$ criterion at the end of each cohort, a preliminary evidence of anti-tumor activity could be declared if the number of confirmed responses is at least 34 out of 100 subjects in each Cohort C and Cohort D.

Clinical benefit rate (CBR) is defined as the percentage of subjects achieving complete or partial response, or durable stable disease (duration of at least 6 months) as defined by RECIST v1.1. Observed ORR and CBR, along with their two-sided 95% confidence intervals, will be presented for each cohort and dose level as appropriate.

Time to event endpoints including progression-free survival (PFS), duration of response (DOR), time to treatment failure (TTF), and overall survival (OS) will be estimated using the Kaplan-Meier method. DOR will be calculated as time from initial response of CR or PR to progressive disease (PD) or death due to underlying disease, whichever comes first, only for subjects who achieve CR or PR. PFS is defined as the time from first infusion of study drug to PD or death due to any cause. TTF is defined as the time from the first infusion of the study drug to discontinuation of treatment for any reason, including disease progression, treatment toxicity, death, and will be utilized to capture clinical benefit for patients continuing treatment beyond RECIST v1.1 defined disease progression. OS is defined as the time from first infusion of study drug to death due to any cause. For time-to-endpoint endpoints, Kaplan-Meier estimates will be presented graphically, and median time to event, along with corresponding 95% Cis, will be obtained from the Kaplan-Meier estimates.

Example 4. Clinical Results of the Combination (JNJ-61186372+Lazertinib)

The combination of lazertinib and JNJ-61186372 was explored in a Phase 1 study in a combination dose escalation cohort (Part 1, see Example 3). A dose of 240 mg lazertinib (oral; once daily) and 1050 mg (subjects<80 kg)/1400 mg (subjects>80 kg) JNJ61186372 (IV weekly for Cycle 1; biweekly from Cycle 2) was identified as safe and tolerable, after no dose limiting toxicities (DLTs) were observed in dose cohorts evaluated. A Part 2 expansion cohort (Cohort E, see Example 3) was opened to further characterize the safety, tolerability, and preliminary efficacy of the combination in 40 subjects with EGFR-mutated NSCLC, who have progressed on osimertinib. In parallel, an additional Part 1 cohort of treatment naïve subjects with EGFR-mutated NSCLC was assessed to confirm the dose in this population and was subsequently expanded to 20 subjects to further characterize the safety and tolerability of the combination in subjects without previous exposure to anti-EGFR therapy. A total of 36 subjects had been treated with lazertinib in combination with JNJ-61186372 in the Phase 1 study (34 subjects in Part 1 and 2 subjects in the expansion cohort (Cohort E)). The most common adverse events (AEs) were consistent with toxicities associated with EGFR inhibition in subjects treated with the combination and included rash, dermatitis acneiform, paronychia, stomatitis, pruritis, and diarrhea and were similar to AEs observed with other approved EGFR TKIs. Evidence of clinical activity, defined as tumor response or shrinkage as assessed by the study investigator, was observed in the majority of subjects in the initial 26 subject combination dose escalation, including in subjects with unmet need, with either EGFR T790M negative disease after progression on 1st generation TKI, and in subjects with progression after prior 3rd generation TKI therapy. These results demonstrated activity of the combination in subjects for whom there are currently no approved targeted therapies.

Example 5. Clinical Trial of Lazertinib Monotherapy in Patients with EGFR Mutation Positive Advanced NSCLC Clinical Trial No. NCT03046992 was primarily designed to evaluate the safety, tolerability, and efficacy of YH25448 in in patients with EGFR mutation positive (EGFRm+) advanced NSCLC with or without asymptomatic brain metastasis who progressed following prior therapy with an EGFR TKIs agent.

Methods:

Patients with advanced and metastatic NSCLC who had progressed after treatment with EGFR-TKIs with/without asymptomatic brain metastases (BM) were enrolled in an open-label, multicenter, phase I/II study with dose-escalation and expansion cohorts. Lazertinib was administered once daily at doses between 20 to 320 mg in a 21-day cycle. Patients were assessed for safety, tolerability, pharmacokinetics and efficacy. T790M status was confirmed in the dose-expansion cohorts.

Results:

A total of 115 patients (median age 62 years, female 62%) were enrolled. The dose-escalation cohort included 38 patients administered with 20 to 320 mg across 7 dose levels, and 77 patients in the dose-expansion cohort were administered with 40 to 240 mg across 5 dose levels. No dose-limiting toxicities were observed in the dose-escalation cohort. Systemic exposure increased dose-dependently. Of the evaluable patients (n=110) at data cut-off, the objective response rate (ORR) was 65% (95% confidence interval [CI], 54.9 to 73.4). The ORR for 93 of the T790M+ patients was 69% (95% CI, 58.4 to 78.0). In patients with BM (n=12), the intracranial ORR was 50% (95% CI, 21.1 to 78.9). The most common treatment-emergent adverse events (TEAEs) were pruritus (19%), decreased appetite (17%), rash (14%), and constipation (12%). The most frequently reported TEAEs of grade≥3 were hyponatraemia (2%), nausea (2%) and pneumonia (2%).

| ORR in T790M + patients: | | | | | | |
|---|---|---|---|---|---|---|
| Dose QD | 20 mg | 40 mg | 80 mg | 120 mg | 160 mg | 240 mg |
| Evaluable patients*, n | 2 | 25 | 18 | 22 | 18 | 8 |
| ORR, n (%) | 2 (100) | 17 (68) | 11 (61) | 17 (77) | 11 (61) | 6 (75) |

*Patients were deemed evaluable for response if they underwent a post-baseline radiological assessment (RECIST 1.1) or were discontinued prior to the post-baseline assessment.

Conclusions:

Lazertinib was well tolerated and exhibited promising systemic and intracranial anti-tumor activity at multiple dose levels in EGFR T790M+NSCLC patients.

Embodiments of the Combination

The following clauses describe particular Embodiments of the present invention.

1) A pharmaceutical combination comprising a therapeutically effective amount of an isolated bispecific anti-epidermal growth factor receptor (EGFR)/hepatocyte growth factor receptor (c-Met) antibody and a therapeutically effective amount of a compound of formula (I)

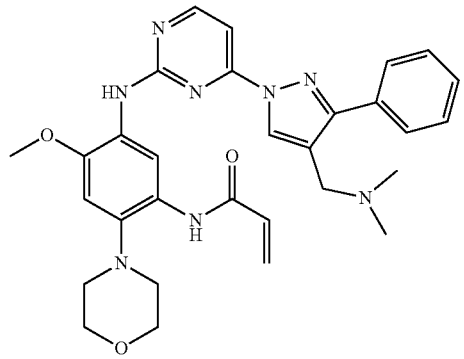

(I)

, or solvate, hydrate, tautomer, or a pharmaceutically acceptable salt thereof, for use in the treatment of EGFR or c-Met expressing cancer.

2) The pharmaceutical combination for use of Embodiment 1, wherein the bispecific anti-EGFR/c-Met antibody comprises a first domain that binds EGFR comprising a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6 and a second domain that binds c-Met comprising the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12.

3) The pharmaceutical combination for use of Embodiment 2, wherein the first domain that binds EGFR comprises a heavy chain variable region (VH) of SEQ ID NO: 13 and a light chain variable region (VL) of SEQ ID NO: 14 and the second domain that binds c-Met comprises the VH of SEQ ID NO: 15 and the VL of SEQ ID NO: 16.

4) The pharmaceutical combination for use of any one of Embodiments 1 to 3, wherein the bispecific anti-EGFR/c-Met antibody is an IgG1 isotype.

5) The pharmaceutical combination for use of any one of Embodiments 1 to 4, wherein the bispecific anti-EGFR/c-Met antibody comprises a first heavy chain (HC1) of SEQ ID NO: 17, a first light chain (LC1) of SEQ ID NO: 18, a second heavy chain (HC2) of SEQ ID NO: 19 and a second light chain (LC2) of SEQ ID NO: 20.

6) The pharmaceutical combination for use of any one of Embodiments 1 to 5, wherein the bispecific anti-EGFR/ c-Met antibody has a biantennary glycan structure with a fucose content of between about 1% to about 15%.

7) The pharmaceutical combination for use of any one of Embodiments 1 to 6, wherein the compound of formula (I) or solvate, hydrate, tautomer, or a pharmaceutically acceptable salt thereof is represented by a compound of formula (II)

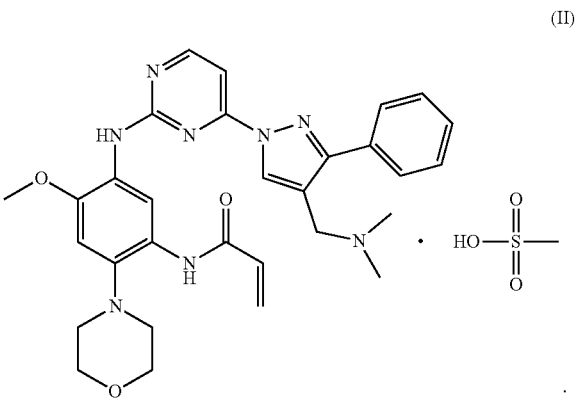

(II)

8) The pharmaceutical combination for use of any one of Embodiments 1 to 6, wherein the compound of formula (I) or solvate, hydrate, tautomer, or a pharmaceutically acceptable salt thereof is N-(5-(4-(4-((dimethylamino) methyl)-3-phenyl-1H-pyrazol-1-yl)pyrimidin-2-ylamino)-4-methoxy-2-morpholinophenyl)acrylamide.

9) The pharmaceutical combination for use of any one of Embodiments 1 to 8, wherein the EGFR or c-Met expressing cancer is associated with a wild-type EGFR, an EGFR mutation, an EGFR gene amplification, increased levels of circulating HGF, a wild-type c-Met, a c-Met mutation, a c-Met gene amplification or a mutant KRAS.

10) The pharmaceutical combination for use of Embodiment 9, wherein the EGFR mutation is E709K, L718Q, L718V, G719A, G719X, G724X, G724S, I744T, E746K, L747S, E749Q, A750P, A755V, V765M, C775Y, T790M, L792H, L792V, G796S, G796R, G796C, C797S, T8541, L858P, L858R, L861Q, delE746-A750, delE746_T751InsKV, delE746_A750InsHS, delE746_T751InsFPT, delE746_T751InsL, delE746_S752InsIP, delE746_P753InsMS, delE746_T751InsA, delE746_T75IInsAPT, delE746_T751InsVA, delE746_S752InsV, delE746 P753InsVS, delE746_K754InsGG, delE746_E749, delE746_E749InsP, delL747_E749, delL747_A750InsP, delL747_T751InsP, delL747_T751InsN, delL747_S752InsPT, delL747_P753InsNS, delL747_S752InsPI, delL747_S752, delL747_P753InsS, delL747_K754, dekL747_T751InsS, dekL747_T751, delL747_P753InsS, delA750_I759InsPT, delT751_I759InsT, delS752_I759, delT751_I759InsN, delT751_D761InsNLY, delS752_I759, delR748-P753, delL747-P753insS, delL747-T751, M766 A767InsA, S768_V769InsSVA, P772_H773InsNS, D761_E762InsX$_{1-7}$, A763_Y764InsX$_{1-7}$, Y764_Y765 InsX$_{1-7}$, M766_A767InsX$_{1-7}$, A767_V768 InsX$_{1-7}$, S768_V769 InsX$_{1-7}$, V769_D770 InsX$_{1-7}$, D770_N771 InsX$_{7}$, N771_P772 InsX$_{17}$, P772_H773 InsX$_{1-7}$, H773_V774 InsX$_{1-7}$, V774_C775 InsX$_{1-7}$, one or more deletions in EGFR exon 20, or one or more insertions in EGFR exon 20, one or more deletions in EGRF exon 19, or one or more insertions in EGFR exon 19, or any combination thereof, wherein X is any amino acids.

11) The pharmaceutical combination for use of Embodiment 10, wherein the EGFR mutation is the one or more deletions in exon 19 or L858R, or any combination thereof.

12) The pharmaceutical combination for use of Embodiment 9, wherein the c-Met mutation is c-Met exon 14 skipping mutation.

13) The pharmaceutical combination for use of Embodiment 9, wherein the mutant KRAS has a G12V, G12C or G12A substitution.

14) The pharmaceutical combination for use of any one of Embodiments 1 to 13, wherein the subject has been diagnosed with the EGFR mutation prior to administering the combination therapy.

15) The pharmaceutical combination for use of any one of Embodiments 1 to 14, wherein the subject has a newly diagnosed EGFR or c-Met expressing cancer.

16) The pharmaceutical combination for use of any one of Embodiments 1 to 15, wherein the subject is EGFR tyrosine kinase inhibitor (TKI) treatment naïve.

17) The pharmaceutical combination for use of any one of Embodiments 1 to 15, wherein the subject is resistant or relapsed to treatment with a first generation EGFR TKI.

18) The pharmaceutical combination for use of Embodiment 17, wherein the first generation EGFR TKI is erlotinib or gefitinib.

19) The pharmaceutical combination for use of any one of Embodiments 1 to 14, wherein the subject is resistant or relapsed to treatment with a second generation EGFR TKI.

20) The pharmaceutical combination for use of Embodiment 19, wherein the second generation EGFR TKI is afatinib.

21) The pharmaceutical combination for use of any one of Embodiments 1 to 14, wherein the subject is resistant or relapsed to treatment with a third generation EGFR TKI.

22) The pharmaceutical combination for use of Embodiment 21, wherein the third generation EGFR TKI is osimertinib.

23) The pharmaceutical combination for use of any one of Embodiments 1 to 22, wherein the EGFR or c-Met expressing cancer is a non-small cell lung cancer (NSCLC), an epithelial cell cancer, a breast cancer, an ovarian cancer, a lung cancer, a squamous cell lung cancer, a lung adenocarcinoma, a small cell lung cancer, a colorectal cancer, an anal cancer, a prostate cancer, a kidney cancer, a bladder cancer, a head and neck cancer, a pharynx cancer, a cancer of the nose, a pancreatic cancer, a skin cancer, an oral cancer, a cancer of the tongue, an esophageal cancer, a vaginal cancer, a cervical cancer, a cancer of the spleen, a testicular cancer, a gastric cancer, a cancer of the thymus, a colon cancer, a thyroid cancer, a liver cancer, a hepatocellular carcinoma (HCC) or sporadic or hereditary papillary renal cell carcinoma (PRCC).

24) The pharmaceutical combination for use of Embodiment 23, wherein the cancer is the NSCLC.

25) The pharmaceutical combination for use of any one of Embodiments 1 to 23, wherein the bispecific anti-EGFR/c-Met antibody is administered at a dose of between about 200 mg and about 2000 mg.

26) The pharmaceutical combination for use of Embodiment 25, wherein the bispecific anti-EGFR/c-Met antibody is administered at a dose of between about 350 mg and about 1400 mg.

27) The pharmaceutical combination for use of Embodiment 26, wherein the bispecific anti-EGFR/c-Met antibody is administered at a dose of about 350 mg, about 700 mg, about 1050 mg or about 1400 mg.

28) The pharmaceutical combination for use of any one of Embodiments 1 to 27, wherein the bispecific anti-EGFR/c-Met antibody is administered once a week.

29) The pharmaceutical combination for use of any one of Embodiments 1 to 27, wherein the bispecific anti-EGFR/c-Met antibody is administered once in two weeks.

30) The pharmaceutical combination for use of any one of Embodiments 1 to 29, wherein the compound of formula (I) or solvate, hydrate, tautomer, or a pharmaceutically acceptable salt thereof is administered at a dose of between about 20 mg and about 320 mg.

31) The pharmaceutical combination for use of Embodiment 30, wherein the compound of formula (I) or solvate, hydrate, tautomer, or a pharmaceutically acceptable salt thereof is administered at a dose of about 160 mg or about 240 mg.

32) The pharmaceutical combination for use of any one of Embodiments 1 to 31, wherein the compound of formula (I) or solvate, hydrate, tautomer, or a pharmaceutically acceptable salt thereof is administered once a day.

33) The pharmaceutical combination for use of any one of Embodiments 1 to 24, wherein the bispecific anti-EGFR/c-Met antibody is administered at a dose of between about 350 mg and about 1400 mg weekly for four weeks and once in two weeks thereafter, and the compound of formula (I) or solvate, hydrate, tautomer, or a pharmaceutically acceptable salt thereof is administered at a dose of between about 160 mg and about 240 mg daily.

34) The pharmaceutical combination for use of Embodiment 33, wherein the bispecific anti-EGFR/c-Met antibody is administered at a dose of about 700 mg weekly for four weeks and once in two weeks thereafter, and the compound of formula (I) or solvate, hydrate, tautomer, or a pharmaceutically acceptable salt thereof is administered at a dose of about 160 mg daily.

35) The pharmaceutical combination for use of Embodiment 33, wherein the bispecific anti-EGFR/c-Met antibody is administered at a dose of about 1050 mg weekly for four weeks and once in two weeks thereafter, and the compound of formula (I) or solvate, hydrate, tautomer, or a pharmaceutically acceptable salt thereof is administered at a dose of about 160 mg daily.

36) The pharmaceutical combination for use of Embodiment 33, wherein the bispecific anti-EGFR/c-Met antibody is administered at a dose of about 1400 mg weekly for four weeks and once in two weeks thereafter, and the compound of formula (I) or solvate, hydrate, tautomer, or a pharmaceutically acceptable salt thereof is administered at a dose of about 160 mg daily.

37) The pharmaceutical combination for use of Embodiment 33, wherein the bispecific anti-EGFR/c-Met antibody is administered at a dose of about 700 mg weekly for four weeks and once in two weeks thereafter, and the compound of formula (I) or solvate, hydrate, tautomer, or a pharmaceutically acceptable salt thereof is administered at a dose of about 240 mg daily.

38) The pharmaceutical combination for use of Embodiment 33, wherein the bispecific anti-EGFR/c-Met antibody is administered at a dose of about 1050 mg weekly for four weeks and once in two weeks thereafter, and the compound of formula (I) or solvate, hydrate, tautomer, or a pharmaceutically acceptable salt thereof is administered at a dose of about 240 mg daily.

39) The pharmaceutical combination for use of Embodiment 33, wherein the bispecific anti-EGFR/c-Met antibody is administered at a dose of about 1400 mg weekly for four weeks and once in two weeks thereafter, and the compound of formula (I) or solvate, hydrate, tautomer, or a pharmaceutically acceptable salt thereof is administered at a dose of about 240 mg daily.

40) The pharmaceutical combination for use of any one of Embodiments 1 to 39, wherein the bispecific anti-EGFR/c-Met antibody is administered after administering the compound of formula (I) or solvate, hydrate, tautomer, or a pharmaceutically acceptable salt thereof.

41) The pharmaceutical combination for use of Embodiment 40, wherein the bispecific anti-EGFR/c-Met antibody is administered one or more times after administering the compound of formula (I) or solvate, hydrate, tautomer, or a pharmaceutically acceptable salt thereof.

42) The pharmaceutical combination for use of Embodiment 41, wherein the bispecific anti-EGFR/c-Met antibody is administered two, three, four, five, six, seven, eight, nine, ten or more times after administering the compound of formula (I) or solvate, hydrate, tautomer, or a pharmaceutically acceptable salt thereof.

43) The pharmaceutical combination for use of any one of Embodiments 1 to 42, wherein the subject is homozygous for phenylalanine at position 158 of CD16 or heterozygous for valine and phenylalanine at position 158 of CD16.

44) The pharmaceutical combination for use of any one of Embodiments 1 to 43, comprising further administering a third anti-cancer therapy.

45) The pharmaceutical combination for use of Embodiment 44, wherein the third anti-cancer therapy is chemotherapy, a targeted anti-cancer therapy or a kinase inhibitor.

46) A pharmaceutical combination of a therapeutically effective amount of an isolated bispecific anti-epidermal growth factor receptor (EGFR)/hepatocyte growth factor receptor (c-Met) antibody and a therapeutically effective amount of a compound of formula (I)

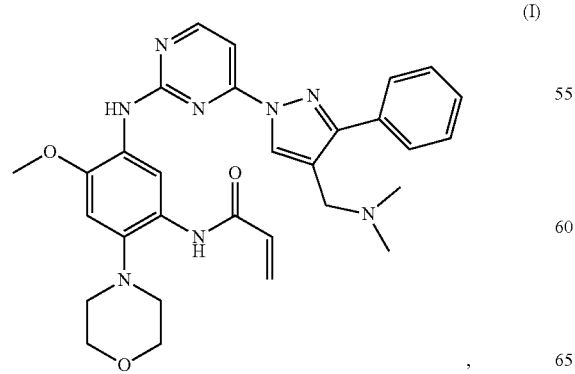

(I)

, or solvate, hydrate, tautomer, or a pharmaceutically acceptable salt thereof.

47) The pharmaceutical combination of Embodiment 46 wherein the isolated bispecific anti-epidermal growth factor receptor (EGFR)/hepatocyte growth factor receptor (c-Met) antibody is a bispecific anti-EGFR/c-Met antibody comprising a first domain that binds EGFR comprising the HCDR1 of SEQ ID NO: 1, the HCDR2 of SEQ ID NO: 2, the HCDR3 of SEQ ID NO: 3, the LCDR1 of SEQ ID NO: 4, the LCDR2 of SEQ ID NO: 5 and the LCDR3 of SEQ ID NO: 6 and a second domain that binds c-Met comprising the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12.

48) The pharmaceutical combination of Embodiment 46 or 47, wherein the compound of formula (I)

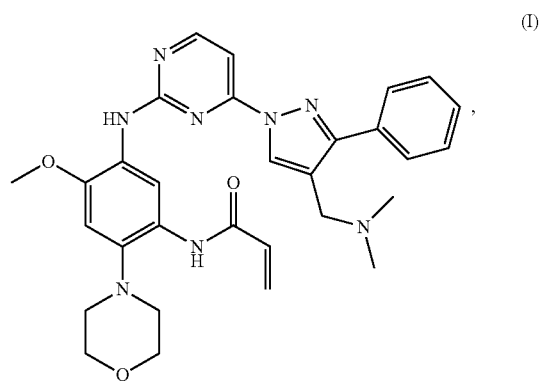 [SMILES: C=CC(=O)Nc1cc(Nc2nccc(-n3cc(CN(C)C)c(-c4ccccc4)n3)n2)c(OC)cc1N1CCOCC1]

(I)

or solvate, hydrate, tautomer, or a pharmaceutically acceptable salt thereof is lazertinib.

49) The pharmaceutical combination of Embodiment 46 or 47, wherein the compound of formula (I)

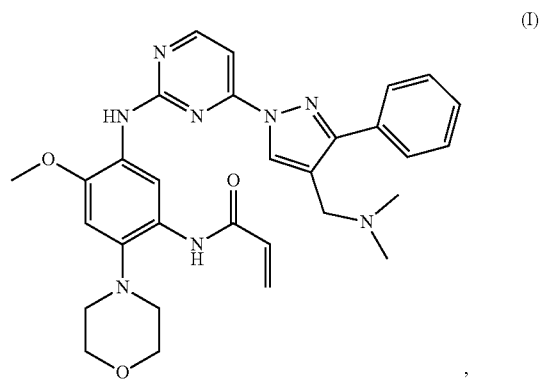 [SMILES: C=CC(=O)Nc1cc(Nc2nccc(-n3cc(CN(C)C)c(-c4ccccc4)n3)n2)c(OC)cc1N1CCOCC1]

(I)

, or solvate, hydrate, tautomer, or a pharmaceutically acceptable salt thereof is lazertinib mesylate.

50) The pharmaceutical combination of any one of Embodiments 46 to 49, comprising between about 350 mg and about 1400 mg of the bispecific EGFR/c-Met antibody and between about 160 mg and about 240 mg the compound of formula (I) or solvate, hydrate, tautomer or a pharmaceutically acceptable salt thereof.

51) The pharmaceutical combination of Embodiment 47, wherein the compound of formula (I) or solvate, hydrate, tautomer, or a pharmaceutically acceptable salt thereof is N-(5-(4-(4-((dimethylamino)methyl)-3-phenyl-1H-pyrazol-1-yl)pyrimidin-2-ylamino)-4-methoxy-2-morpholinophenyl)acrylamide.

52) The pharmaceutical combination of any one of Embodiments 46 to 51, wherein the pharmaceutical combination is a non-fixed combination.

53) The pharmaceutical combination of any one of Embodiments 46 to 52, wherein the first domain that binds EGFR of the bispecific anti-EGFR/c-Met antibody comprises the VH of SEQ ID NO: 13 and the VL of SEQ ID NO: 14; and the second domain that binds c-Met comprises the VH of SEQ ID NO: 15 and the VL of SEQ ID NO: 16.

54) The pharmaceutical combination of any one of Embodiments 46 to 53, wherein the bispecific anti-EGFR/c-Met antibody comprises the HC1 of SEQ ID NO: 17, the LC1 of SEQ ID NO: 18, the HC2 of SEQ ID NO: 19 and the LC2 of SEQ ID NO: 20.

55) An isolated bispecific anti-epidermal growth factor receptor (EGFR)/hepatocyte growth factor receptor (c-Met) antibody for use in combination with a compound of formula (I)

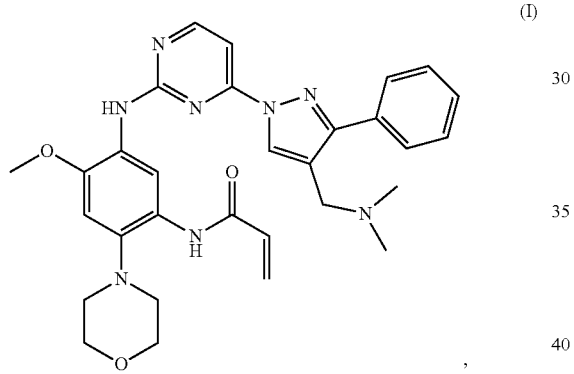

(I)

or solvate, hydrate, tautomer, or a pharmaceutically acceptable salt thereof, in the treatment of EGFR or c-Met expressing cancer, in particular in the treatment of EGFR or c-Met expressing cancer in a subject.

56) The isolated bispecific anti-epidermal growth factor receptor (EGFR)/hepatocyte growth factor receptor (c-Met) antibody for use of Embodiment 55 wherein the isolated bispecific anti-epidermal growth factor receptor (EGFR)/hepatocyte growth factor receptor (c-Met) antibody is a bispecific anti-EGFR/c-Met antibody comprising a first domain that binds EGFR comprising the HCDR1 of SEQ ID NO: 1, the HCDR2 of SEQ ID NO: 2, the HCDR3 of SEQ ID NO: 3, the LCDR1 of SEQ ID NO: 4, the LCDR2 of SEQ ID NO: 5 and the LCDR3 of SEQ ID NO: 6 and a second domain that binds c-Met comprising the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12.

57) The isolated bispecific anti-epidermal growth factor receptor (EGFR)/hepatocyte growth factor receptor (c-Met) antibody for use of Embodiment 55 or 56, wherein the compound of formula (I)

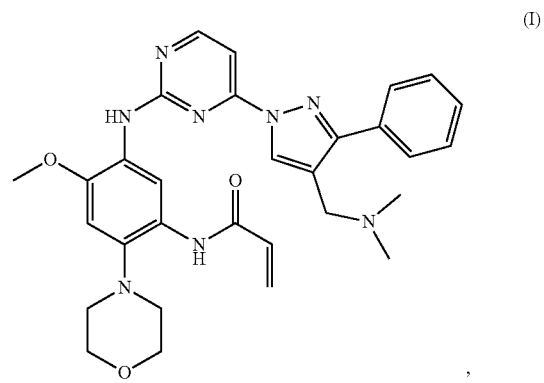 [SMILES: C=CC(=O)Nc1cc(Nc2nccc(-n3cc(CN(C)C)c(-c4ccccc4)n3)n2)c(OC)cc1N1CCOCC1]

(I)

or solvate, hydrate, tautomer, or a pharmaceutically acceptable salt thereof is lazertinib.

58) The isolated bispecific anti-epidermal growth factor receptor (EGFR)/hepatocyte growth factor receptor (c-Met) antibody for use of Embodiment 55 or 56, wherein the compound of formula (I)

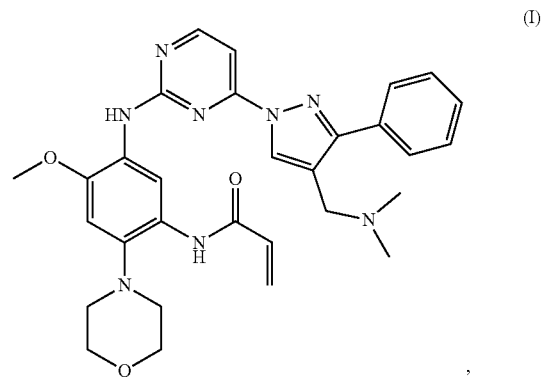 [SMILES: C=CC(=O)Nc1cc(Nc2nccc(-n3cc(CN(C)C)c(-c4ccccc4)n3)n2)c(OC)cc1N1CCOCC1]

(I)

or solvate, hydrate, tautomer, or a pharmaceutically acceptable salt thereof is lazertinib mesylate.

59) The isolated bispecific anti-epidermal growth factor receptor (EGFR)/hepatocyte growth factor receptor (c-Met) antibody for use of any one of Embodiments 55 to 58, comprising between about 350 mg and about 1400 mg of the bispecific EGFR/c-Met antibody and between about 160 mg and about 240 mg the compound of formula (I) or solvate, hydrate, tautomer or a pharmaceutically acceptable salt thereof.

60) The isolated bispecific anti-epidermal growth factor receptor (EGFR)/hepatocyte growth factor receptor (c-Met) antibody for use of any one of Embodiments 55 to 59, wherein the first domain that binds EGFR of the bispecific anti-EGFR/c-Met antibody comprises the VH of SEQ ID NO: 13 and the VL of SEQ ID NO: 14; and the second domain that binds c-Met comprises the VH of SEQ ID NO: 15 and the VL of SEQ ID NO: 16.

61) The isolated bispecific anti-epidermal growth factor receptor (EGFR)/hepatocyte growth factor receptor (c-Met) antibody for use of any one of Embodiments 55 to 60, wherein the bispecific anti-EGFR/c-Met antibody comprises the HC1 of SEQ ID NO: 17, the LC1 of SEQ ID NO: 18, the HC2 of SEQ ID NO: 19 and the LC2 of SEQ ID NO: 2

We claim:

1. A method of treating cancer in a human subject comprising administering lazertinib to the subject in an amount between about 20 mg and about 320 mg once daily, wherein the cancer is EGFR Mutation Positive non-small cell lung cancer (NSCLC).

2. The method of claim 1, wherein the cancer is EGFR T790M+ NSCLC.

3. The method of claim 1, wherein the subject exhibits brain metastasis.

4. The method of claim 1 comprising administering the lazertinib to the subject in an amount between about 40 mg and about 240 mg once daily.

5. The method of claim 1 comprising administering the lazertinib to the subject in an amount of about 240 mg once daily.

6. The method of claim 1 comprising administering the lazertinib to the subject once daily over a period of at least 3 weeks.

7. The method of claim 1 comprising administering the lazertinib to the subject once daily over a period of at least 6 weeks.

* * * * *

SEQUENCE LISTING

<160> NUMBER OF SEQ ID NOS: 21

<210> SEQ ID NO 1
<211> LENGTH: 5
<212> TYPE: PRT
<213> ORGANISM: Artificial Sequence
<220> FEATURE:
<223> OTHER INFORMATION: HCDR1, EGFR binding arm

<400> SEQUENCE: 1

Thr Tyr Gly Met His
1               5

<210> SEQ ID NO 2
<211> LENGTH: 17
<212> TYPE: PRT
<213> ORGANISM: Artificial Sequence
<220> FEATURE:
<223> OTHER INFORMATION: HCDR2, EGFR binding arm

<400> SEQUENCE: 2

Val Ile Trp Asp Asp Gly Ser Tyr Lys Tyr Tyr Gly Asp Ser Val Lys
1               5                   10                  15

Gly

<210> SEQ ID NO 3
<211> LENGTH: 16
<212> TYPE: PRT
<213> ORGANISM: Artificial Sequence
<220> FEATURE:
<223> OTHER INFORMATION: HCDR3, EGFR binding arm

<400> SEQUENCE: 3

Asp Gly Ile Thr Met Val Arg Gly Val Met Lys Asp Tyr Phe Asp Tyr
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: LCDR1, EGFR binding arm

<400> SEQUENCE: 4

Arg Ala Ser Gln Asp Ile Ser Ser Ala Leu Val
1               5                   10

<210> SEQ ID NO 5
<211> LENGTH: 7
<212> TYPE: PRT
<213> ORGANISM: Artificial Sequence
<220> FEATURE:
<223> OTHER INFORMATION: LCDR2, EGFR binding arm

<400> SEQUENCE: 5

Asp Ala Ser Ser Leu Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: LCDR3, EGFR binding arm

<400> SEQUENCE: 6

Gln Gln Phe Asn Ser Tyr Pro Leu Thr
1               5

<210> SEQ ID NO 7
<211> LENGTH: 5
<212> TYPE: PRT
<213> ORGANISM: Artificial Sequence
<220> FEATURE:
<223> OTHER INFORMATION: HCDR1, c-Met binding arm

<400> SEQUENCE: 7

Ser Tyr Gly Ile Ser
1               5

<210> SEQ ID NO 8
<211> LENGTH: 17
<212> TYPE: PRT
<213> ORGANISM: Artificial Sequence
<220> FEATURE:
<223> OTHER INFORMATION: HCDR2, c-Met binding arm

<400> SEQUENCE: 8

Trp Ile Ser Ala Tyr Asn Gly Tyr Thr Asn Tyr Ala Gln Lys Leu Gln
1               5                   10                  15

Gly

<210> SEQ ID NO 9
<211> LENGTH: 10
<212> TYPE: PRT
<213> ORGANISM: Artificial Sequence
<220> FEATURE:
<223> OTHER INFORMATION: HCDR3, c-Met binding arm

<400> SEQUENCE: 9

Asp Leu Arg Gly Thr Asn Tyr Phe Asp Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: LCDR1, c-Met binding arm

<400> SEQUENCE: 10

Arg Ala Ser Gln Gly Ile Ser Asn Trp Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: LCDR2, c-Met binding arm

<400> SEQUENCE: 11

Ala Ala Ser Ser Leu Leu Ser
1               5

<210> SEQ ID NO 12
<211> LENGTH: 9
<212> TYPE: PRT
<213> ORGANISM: Artificial Sequence
<220> FEATURE:
<223> OTHER INFORMATION: LCDR3, c-Met binding arm

<400> SEQUENCE: 12

```
Gln Gln Ala Asn Ser Phe Pro Ile Thr
1               5
```

<210> SEQ ID NO 13
<211> LENGTH: 125
<212> TYPE: PRT
<213> ORGANISM: Artificial Sequence
<220> FEATURE:
<223> OTHER INFORMATION: VH, EGFR binding arm

<400> SEQUENCE: 13

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Tyr Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser
        115                 120                 125
```

<210> SEQ ID NO 14
<211> LENGTH: 107
<212> TYPE: PRT
<213> ORGANISM: Artificial Sequence
<220> FEATURE:
<223> OTHER INFORMATION: VL, EGFR binding arm

<400> SEQUENCE: 14

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105
```

<210> SEQ ID NO 15
<211> LENGTH: 119
<212> TYPE: PRT
<213> ORGANISM: Artificial Sequence
<220> FEATURE:
<223> OTHER INFORMATION: VH, c-Met binding arm

<400> SEQUENCE: 15

Gln Val Gln Leu Val Gln Ser Gly Ala Glu Val Lys Lys Pro Gly Ala
1               5                   10                  15

Ser Val Lys Val Ser Cys Glu Thr Ser Gly Tyr Thr Phe Thr Ser Tyr
            20                  25                  30

Gly Ile Ser Trp Val Arg Gln Ala Pro Gly His Gly Leu Glu Trp Met
        35                  40                  45

Gly Trp Ile Ser Ala Tyr Asn Gly Tyr Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Arg Gly Thr Asn Tyr Phe Asp Tyr Trp Gly Gln Gly
            100                 105                 110

Thr Leu Val Thr Val Ser Ser
            115

<210> SEQ ID NO 16
<211> LENGTH: 107
<212> TYPE: PRT
<213> ORGANISM: Artificial Sequence
<220> FEATURE:
<223> OTHER INFORMATION: VL, c-Met binding arm

<400> SEQUENCE: 16

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Phe Gln His Lys Pro Gly Lys Ala Pro Lys Leu Leu Ile
        35                  40                  45

Tyr Ala Ala Ser Ser Leu Leu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 17
<211> LENGTH: 455
<212> TYPE: PRT
<213> ORGANISM: Artificial Sequence
<220> FEATURE:
<223> OTHER INFORMATION: Heavy chain 1

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Tyr Lys Tyr Tyr Gly Asp Ser Val
50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Leu Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 18
<211> LENGTH: 214
<212> TYPE: PRT
<213> ORGANISM: Artificial Sequence
<220> FEATURE:
```

<223> OTHER INFORMATION: Light chain 1

<400> SEQUENCE: 18

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 19
<211> LENGTH: 449
<212> TYPE: PRT
<213> ORGANISM: Artificial Sequence
<220> FEATURE:
<223> OTHER INFORMATION: Heavy chain 2

<400> SEQUENCE: 19

Gln Val Gln Leu Val Gln Ser Gly Ala Glu Val Lys Lys Pro Gly Ala
1               5                   10                  15

Ser Val Lys Val Ser Cys Glu Thr Ser Gly Tyr Thr Phe Thr Ser Tyr
            20                  25                  30

Gly Ile Ser Trp Val Arg Gln Ala Pro Gly His Gly Leu Glu Trp Met
        35                  40                  45

Gly Trp Ile Ser Ala Tyr Asn Gly Tyr Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Arg Gly Thr Asn Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 20
<211> LENGTH: 214
<212> TYPE: PRT
<213> ORGANISM: Artificial Sequence
<220> FEATURE:
<223> OTHER INFORMATION: Light chain 2

<400> SEQUENCE: 20

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30
```

```
Leu Ala Trp Phe Gln His Lys Pro Gly Lys Ala Pro Lys Leu Leu Ile
            35                  40                  45

Tyr Ala Ala Ser Ser Leu Leu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Ile
                 85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 21
<211> LENGTH: 330
<212> TYPE: PRT
<213> ORGANISM: Homo sapiens

<400> SEQUENCE: 21

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

-continued

```
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```